US012631620B2

(12) United States Patent
Nahmias et al.

(10) Patent No.: US 12,631,620 B2
(45) Date of Patent: May 19, 2026

(54) METHODS OF GENERATING ORGANOIDS FOR HIGH THROUGHPUT SCREENING OF DRUGS

(71) Applicant: Yissum Research Development Company of the Hebrew University of Jerusalem Ltd., Jerusalem (IL)

(72) Inventors: Yaakov Nahmias, Mevaseret Zion (IL); Avner Ehrlich, Jerusalem (IL); Muneef Ayyash, Jerusalem (IL)

(73) Assignee: Yissum Research Development Company of the Hebrew University of Jerusalem Ltd., Jerusalem (IL)

( * ) Notice: Subject to any disclaimer, the term of this patent is extended or adjusted under 35 U.S.C. 154(b) by 1175 days.

(21) Appl. No.: 17/408,427

(22) Filed: Aug. 22, 2021

(65) Prior Publication Data

US 2022/0042975 A1     Feb. 10, 2022

Related U.S. Application Data

(63) Continuation of application No. PCT/IL2020/050172, filed on Feb. 16, 2020.

(60) Provisional application No. 62/808,373, filed on Feb. 21, 2019.

(51) Int. Cl.
*G01N 33/50* (2006.01)
*G01N 33/15* (2006.01)

(52) U.S. Cl.
CPC ......... *G01N 33/5014* (2013.01); *G01N 33/15* (2013.01)

(58) Field of Classification Search
CPC ........................... G01N 33/5014; G01N 33/15
See application file for complete search history.

(56) References Cited

FOREIGN PATENT DOCUMENTS

| WO | WO 2017/153992 | 9/2017 |
| WO | WO 2018/027023 | 2/2018 |
| WO | WO 2020/170239 | 8/2020 |

OTHER PUBLICATIONS

Communication Pursuant to Article 94(3) EPC Dated Nov. 29, 2022 From the European Patent Office Re. Application No. 20708680.2. (7 pages).
International Preliminary Report on Patentability Dated Sep. 2, 2021 From the International Bureau of WIPO Re. Application No. PCT/IL2020/050172. (9 Pages).
International Search Report and the Written Opinion Dated Apr. 2, 2020 From the International Searching Authority Re. Application No. PCT/IL2020/050172. (13 Pages).
Bavli et al. "Real-Time Monitoring of Metabolic Function in Liver-on-Chip Microdevices Tracks the Dynamics of Mitochondrial Dysfunction", Proc. Natl. Acad. Sci. USA, PNAS, XP055375339, 113(16): E2231-E2240, Published Online Apr. 4, 2016.
Caragher et al. "Glioblastoma's Next Top Model: Novel Culture System for Brain Cancer Radiotherapy Research", Cancers, XP055678501, 11(1): 44-1-44-23, Jan. 4, 2019.
Czerniecki et al. "High-Throughput Screening Enhances Kidney Organoid Differentiation From Human Pluripotent Stem Cells and Enables Automated Multidimensional Phenotyping", Cell Stem Cell, 22(6): 929-940, Jun. 1, 2018.
Ehrlich et al. "Microphysiological Flux Balance Platform Unravels the Dynamics of Drug Induced Steatosis", Lap on A Chip, XP055678966, 18(17): 2510-2522, Published Online Jul. 2, 2018.
Leung et al. "Microscale 3D Collagen Cell Culture Assays in Conventional Flat-Bottom 384-Well Plates", Journal of Laboratory Automation, XP055678923, 20(2): 138-145, Published Online Dec. 15, 2014.
Karsten Boehnke et al, "Assay Establishment and Validation of a High-Throughput Screening Platform for Three-Dimensional Patient-Derived Colon Cancer Organoid Cultures", Journal of Biomolecular Screening, vol. 21, No. 9, Jan. 1, 2016 (Jan. 1, 2016), pp. 931-941.

*Primary Examiner* — Gregory S Emch
*Assistant Examiner* — Mckenzie A Dunn
(74) *Attorney, Agent, or Firm* — The Roy Gross Law Firm, LLC; Roy D. Gross

(57) ABSTRACT

Methods of generating organoids on multi-well plates are provided by depositing a polymeric solution comprising cells under conditions which result in a homogenous population of organoids, which can be used for high throughput analysis for drug screening and for determining treatment regimens of a drug.

10 Claims, 22 Drawing Sheets
(19 of 22 Drawing Sheet(s) Filed in Color)
Specification includes a Sequence Listing.

Greiner Bio-One Non Treated 60-781186
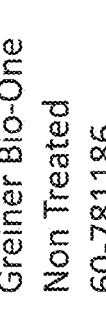
Fig. 1A
Greiner Bio-One TC Treated 60-781182
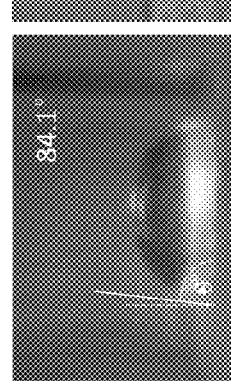
Fig. 1B
Corning Non Treated 3680
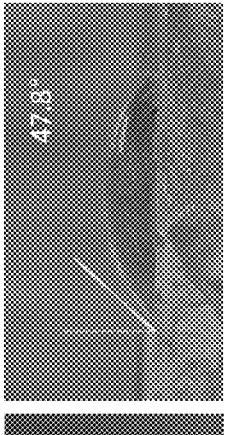
Fig. 1C
Corning TC Treated 3701
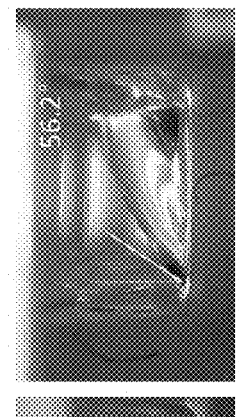
Fig. 1D
Corning Glass 2845-18
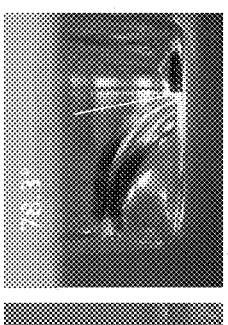
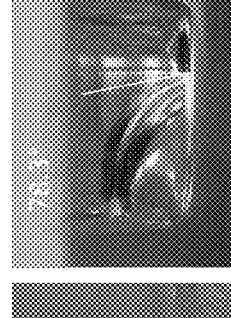
Fig. 1E Human Liver Liver Cancer Human Brain Glioblastoma Neurons / CD31

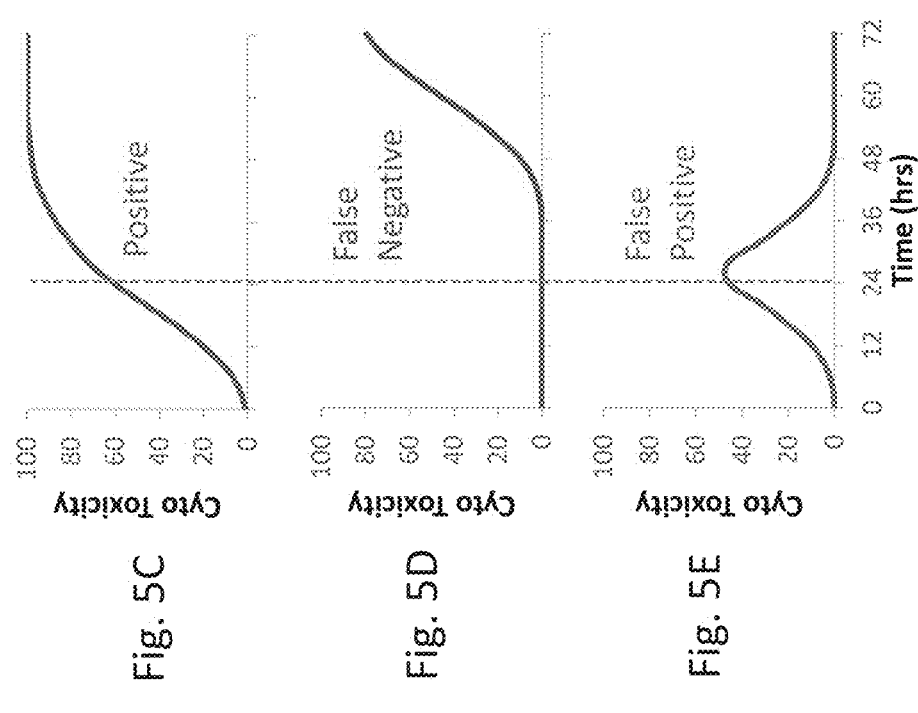
Fig. 5C
Fig. 5D
Fig. 5E
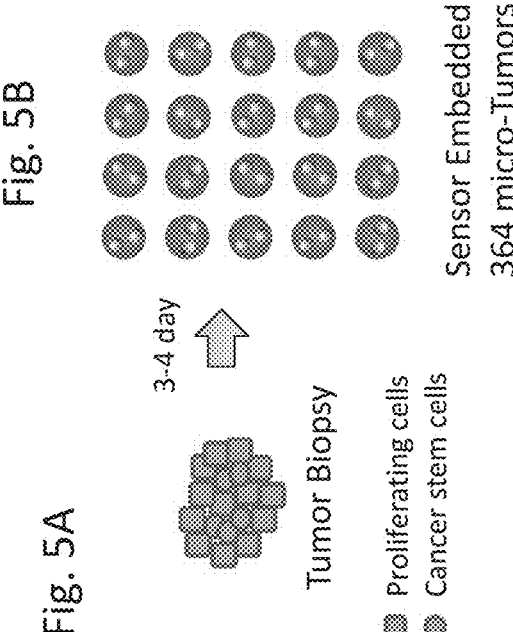
Fig. 5B
Fig. 5A
Tumor Biopsy
3-4 day
Sensor Embedded
364 micro-Tumors
Proliferating cells
Cancer stem cells

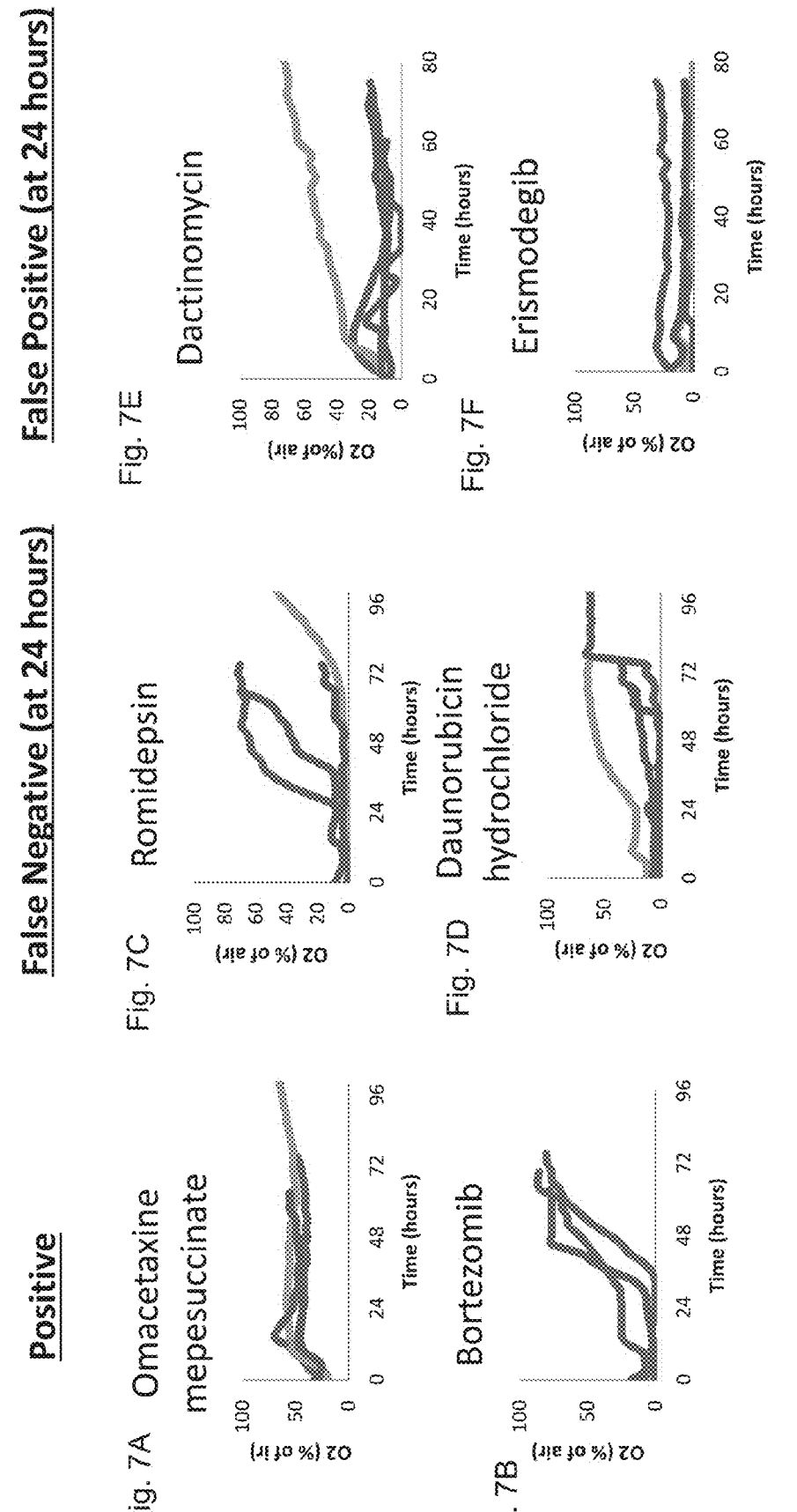
Fig. 7A  Omacetaxine mepesuccinate
Fig. 7B  Bortezomib
Fig. 7C  Romidepsin
Fig. 7D  Daunorubicin hydrochloride
Fig. 7E  Dactinomycin
Fig. 7F  Erismodegib
Positive
False Negative (at 24 hours)
False Positive (at 24 hours)
Cells: U87-MG    Drug Conc.=5μM

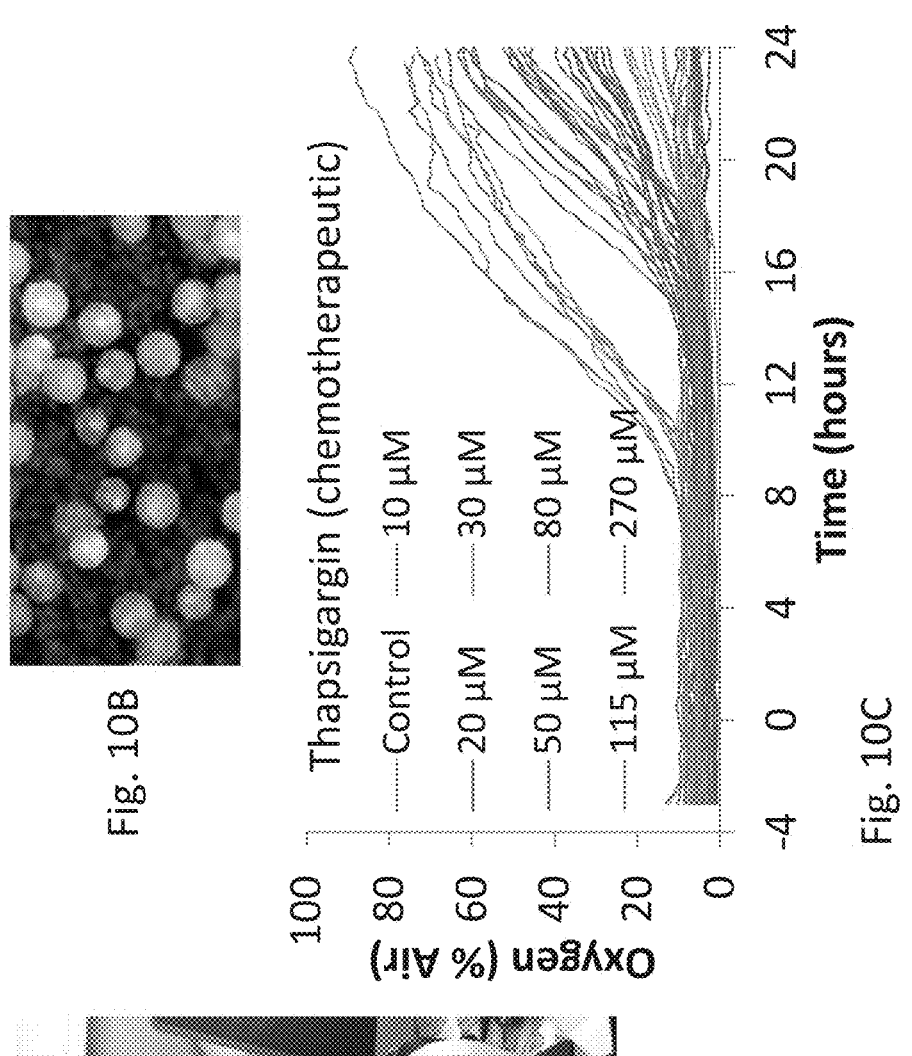
Fig. 10B
Fig. 10C
Thapsigargin (chemotherapeutic)
- Control
- 10 μM
- 20 μM
- 30 μM
- 50 μM
- 80 μM
- 115 μM
- 270 μM
Oxygen (% Air)
Time (hours)
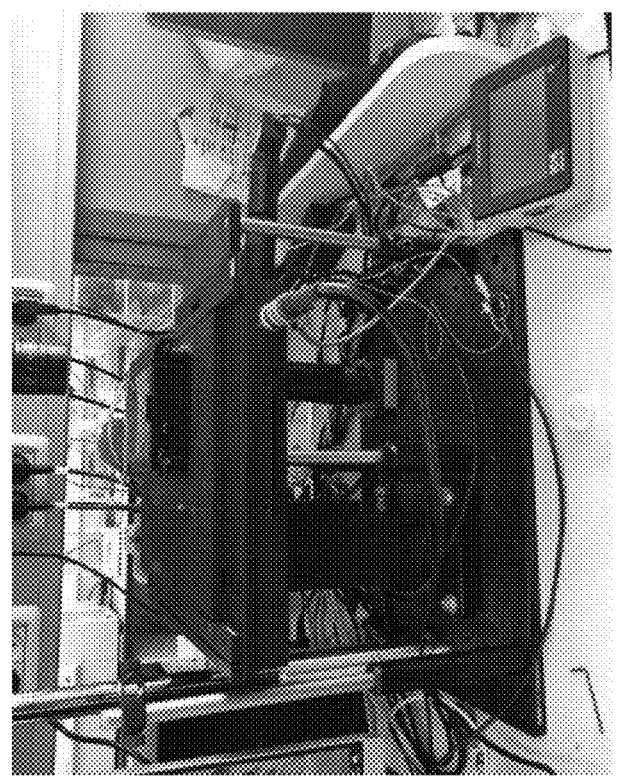
Fig. 10A

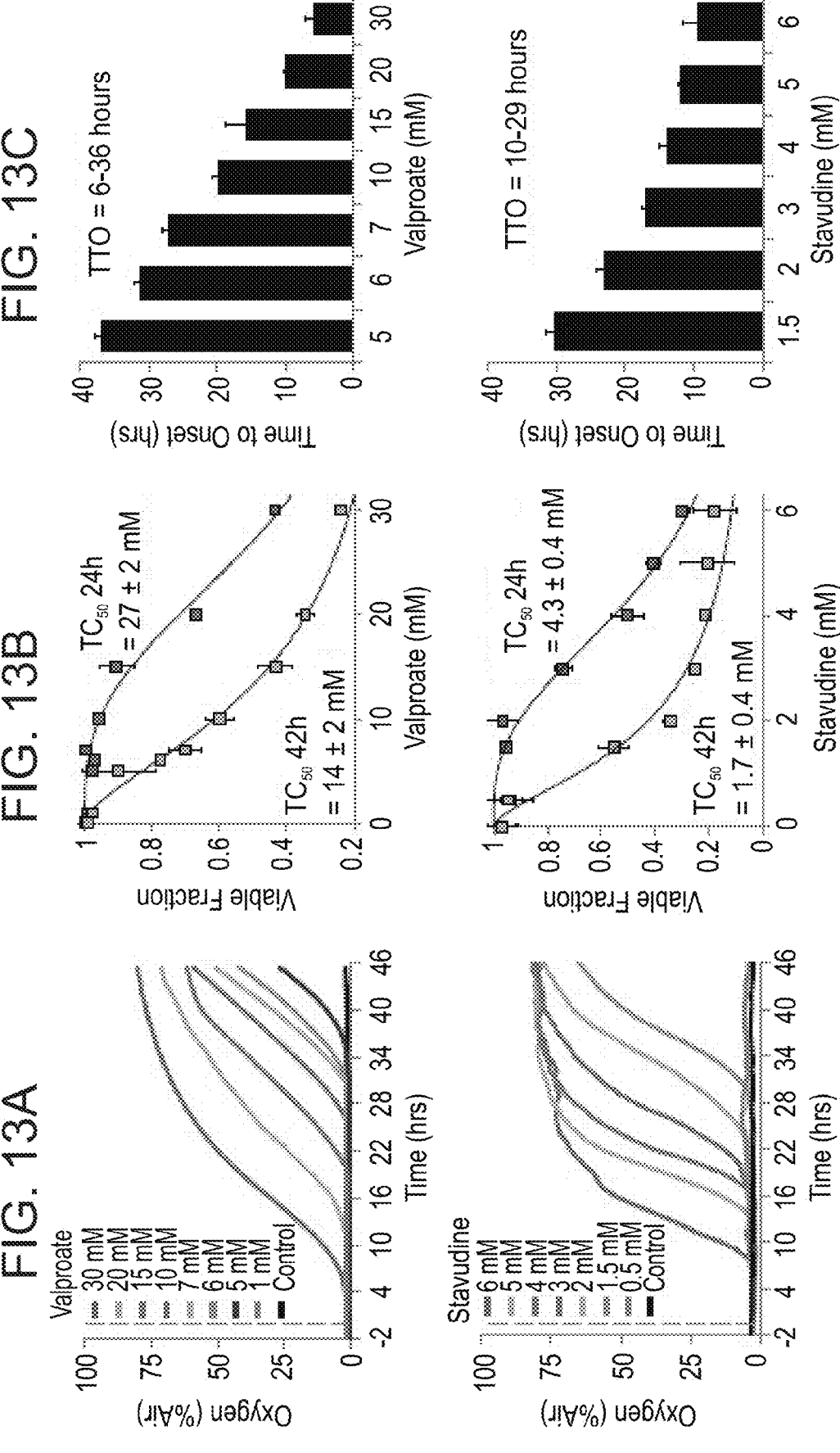

FIG. 14A

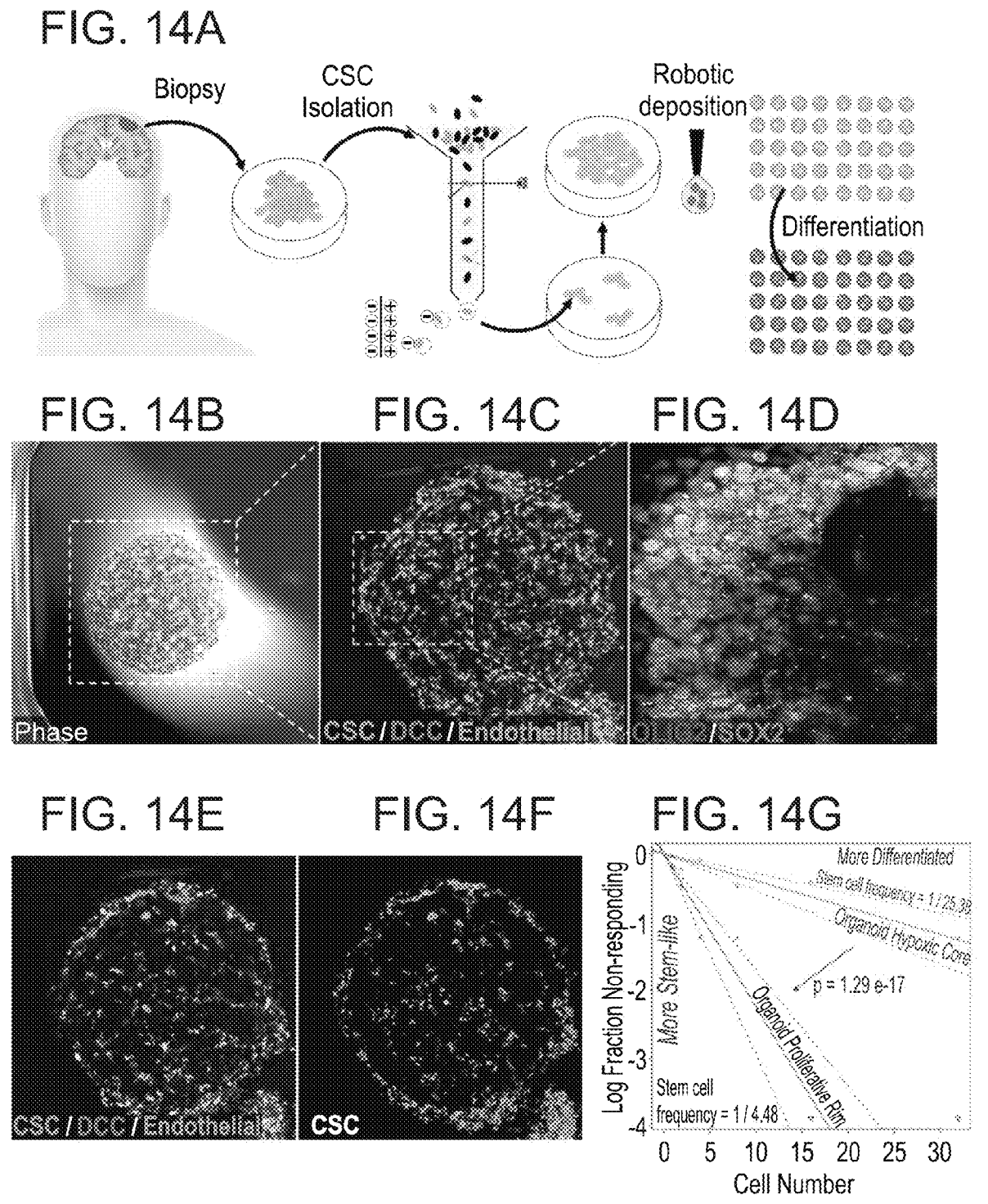

Biopsy

CSC Isolation

Robotic deposition

Differentiation

FIG. 14B

Phase

FIG. 14C

CSC/DCC/Endothelial

CSC/DCC/Endothelial

FIG. 14F

CSC

FIG. 14G

More Differentiated

Stem cell frequency = 1 / 25.38

Organoid Hypoxic Core p = 1.29 e-17

More Stem-like

Organoid Proliferative Rim

Stem cell frequency = 1 / 4.48

Log Fraction Non-responding

Cell Number

7x10⁶ cells 3-4 day

Ascites Fluid

Poliferating cells
Cancer stem cells

Abdominal
Ascites Fluid

Sensor Imbedded
384 micro-Tumors

*Random deposition*    Random Organoids

Aggregation

*Robotic deposition*

Formation

Precise Organoid Deposition

Culture

Cells     Polymer / Gel
Organoid    Liquid / Medium

Day 1   Live / Dead

Day 4

Oxygen (% of Air)

Time (Hours)

FIG. 16G
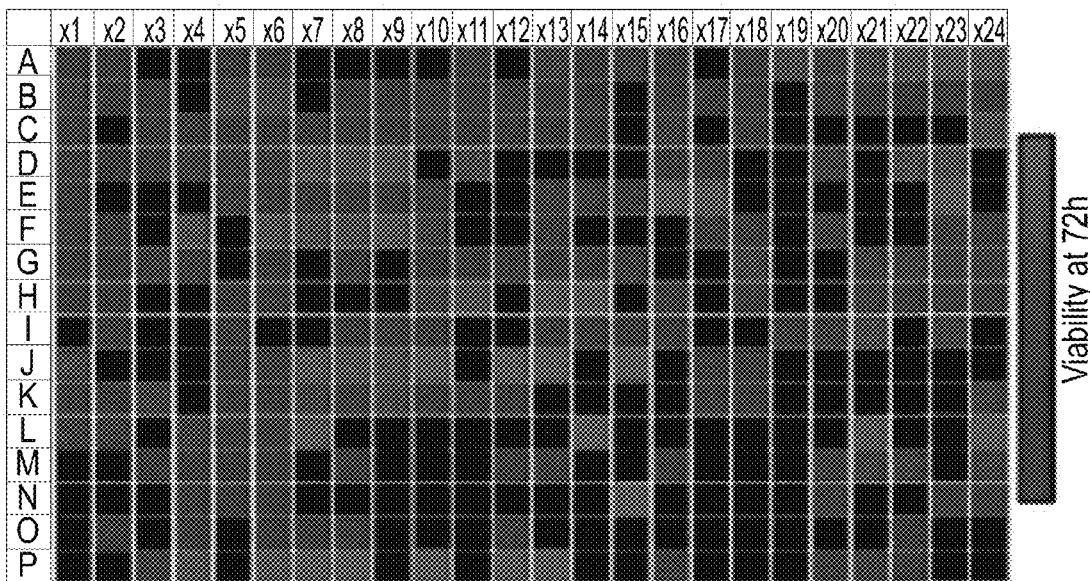
Viability at 72h
FIG. 16H
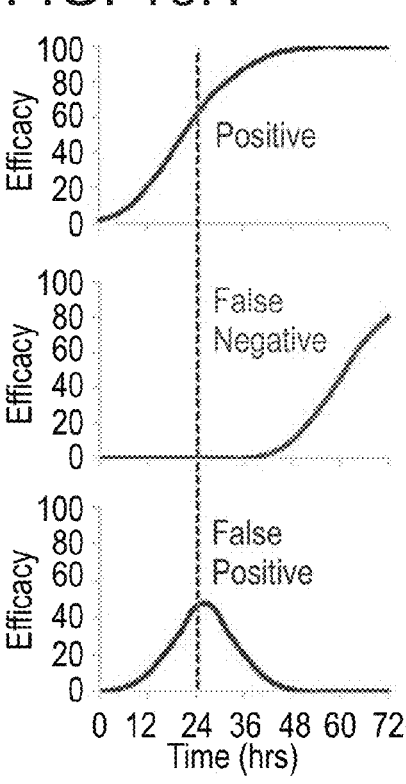
Positive
False Negative
False Positive
FIG. 16I
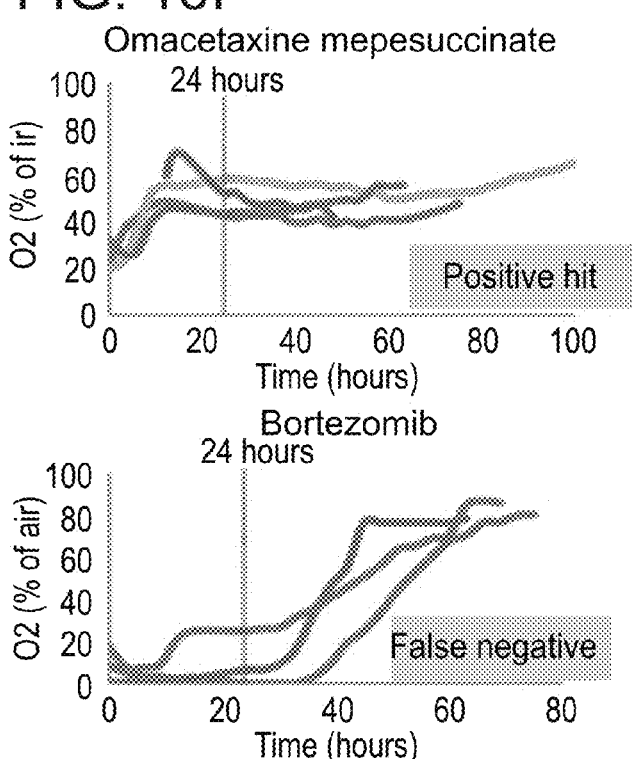
Omacetaxine mepesuccinate
24 hours
Positive hit
Bortezomib
24 hours
False negative
FIG. 16J
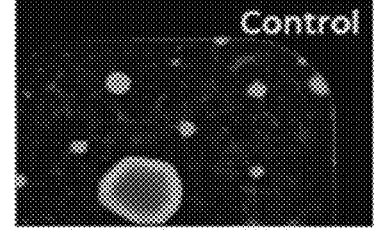

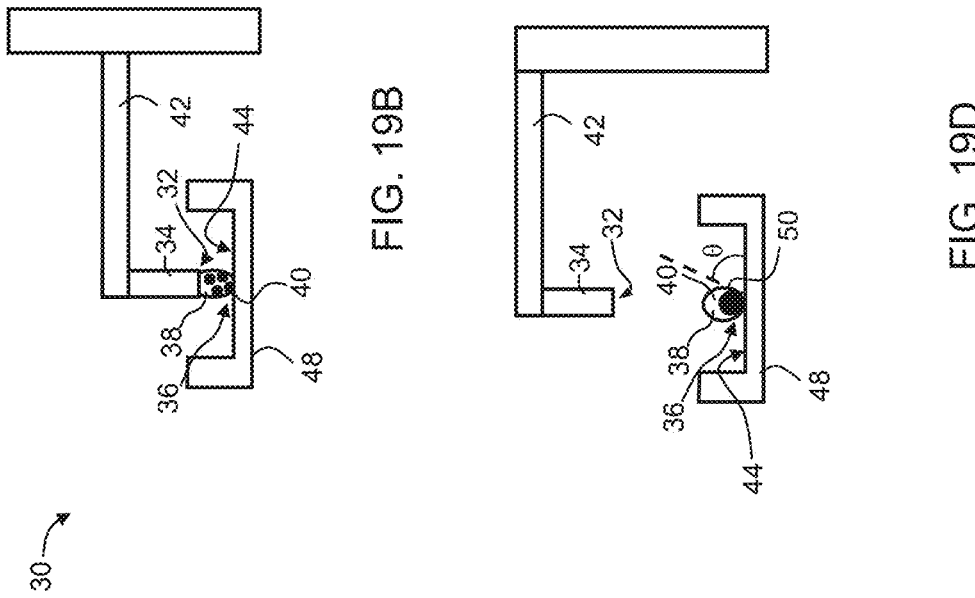
FIG. 19A
FIG. 19B
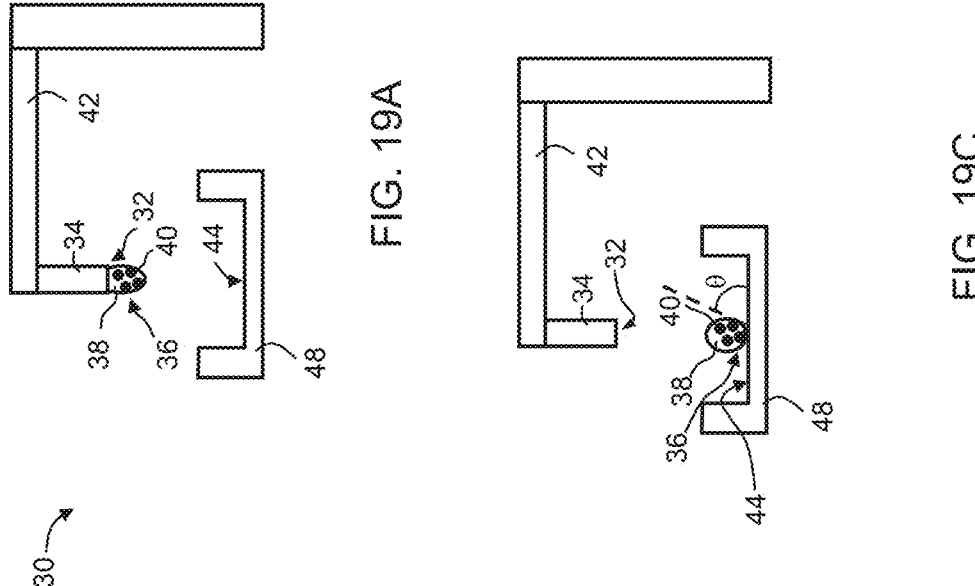
FIG. 19C
FIG. 19D

SEQUENCE LISTING

<160> NUMBER OF SEQ ID NOS: 18

<210> SEQ ID NO 1
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 1
tagacagcgt aaactgcgcc t                                          21

<210> SEQ ID NO 2
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 2
gaagaagaaa atcttatgca gccttg                                     26

<210> SEQ ID NO 3
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 3
tttgggtcag gattgaaagc                                            20

<210> SEQ ID NO 4
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 4
gaacgggaca cctttagaga ag                                         22

<210> SEQ ID NO 5
<211> LENGTH: 21
<212> TYPE: DNA
<213> ORGANISM: Artificial sequence
<220> FEATURE:
<223> OTHER INFORMATION: Single strand DNA oligonucleotide -continued

```
<400> SEQUENCE: 5
cccagtggta atgctcgtcc c                                        21

<210> SEQ ID NO 6
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 6
gatgggaggc cacaaagag                                          19

<210> SEQ ID NO 7
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 7
gctgtccaca aaagcaaatc t                                       21

<210> SEQ ID NO 8
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 8
ctgaccaccc tccggaacta                                         20

<210> SEQ ID NO 9
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 9
tgcagaagat gtagattgtg tgatga                                  26

<210> SEQ ID NO 10
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 10
tgccccacag caaaccgtag                                         20

<210> SEQ ID NO 11
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 11
cttggcttac gtcgtagaca ggtc                                    24

<210> SEQ ID NO 12
```

-continued

```
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 12
tggttgctct ggacaaacag                                              20

<210> SEQ ID NO 13
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 13
cagcaacaag acgacataga gg                                           22

<210> SEQ ID NO 14
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 14
tgggtactcc gaggccaaat                                              20

<210> SEQ ID NO 15
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 15
ttcggtggcc tctagtgaga                                              20

<210> SEQ ID NO 16
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 16
gtcagtgtgt cctccacctc a                                            21

<210> SEQ ID NO 17
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 17
atgtaggcta tgacgttgca                                              20

<210> SEQ ID NO 18
<211> LENGTH: 20
<212> TYPE: DNA
<213> ORGANISM: Artificial sequence
<220> FEATURE:
<223> OTHER INFORMATION: Single strand DNA oligonucleotide
```

-continued

<400> SEQUENCE: 18
gggtccgggt gcagtttatt                                        20

METHODS OF GENERATING ORGANOIDS FOR HIGH THROUGHPUT SCREENING OF DRUGS

RELATED APPLICATIONS

This application is a Continuation of PCT Patent Application No. PCT/IL2020/050172 having International filing date of Feb. 16, 2020, which claims the benefit of priority under 35 USC § 119(e) of U.S. Provisional Patent Application No. 62/808,373 filed on Feb. 21, 2019. The contents of the above applications are all incorporated by reference as if fully set forth herein in their entirety.

The project leading to this application has received funding from the European Research Council (ERC) under the European Union's Horizon 2020 Research and Innovation Programme (Grant Agreement No. [681870]).

SEQUENCE LISTING STATEMENT

The ASCII file, entitled 89126SequenceListing.txt, created on Aug. 22, 2021, comprising 4,101 bytes, submitted concurrently with the filing of this application is incorporated herein by reference.

FIELD AND BACKGROUND OF THE INVENTION

The present invention, in some embodiments thereof, relates to methods of generating organoids on a multi-well plate, methods of drug screening using said organoids and methods of determining treatment regimens for various drugs using organoids.

Three-dimensional culture of spheroids or organoids is rapidly becoming the preferred culture and screening methodology in research labs and the pharmaceutical industry. Organoids show physiological gene expression, support stem cell maintenance and tissue-level function. Current methods of producing three-dimensional spheroids rely on cells randomly coalescing from two-dimensional culture on ultra-low attachment (ULA) surfaces available from Corning, ThermoFisher, S-Bio or others, or gravity-assisted concentration of a cell aggregates. However, ULA surfaces create spheroids of variable size and it is impossible to control the ratio of multiple cell types in each aggregate as different cell types naturally migrate and separate from each other. Due to these limitations, gravity-assisted concentration of aggregates has become more popular. The hanging-drop method is routinely used to form embryoid bodies from stem cells by depositing droplet of cell suspension on a surface and turning it up-side-down. Organoids are formed at the bottom of each drop but are difficult to transfer to multi-well plates for screening purposes. One technology to create hundreds of three-dimensional organoids in one well is using an array of invested pyramids or microwells like in an AggreWell™ plate (STEMCELL Technologies). However, this technique does not support high-throughput screening as each well contains hundreds of organoids. Recently, InSphero developed a multi-well plate and plastics that permit the formation of hanging drops in a 96 or 384-well plate format, termed Akura™ plates. Cells are pipetted to an overhanding chamber and form a hanging drop through a small pore. Once the organoid forms it can be transferred to a well.

Cancer is one of the leading causes of death with global medical costs totalling over $1.2 trillion/year. In spite of significant advances in the molecular understanding, diagnosis, and treatment over the last decade, complete tumor eradication is seldom achieved primarily due to the persistence of stem cell-like cells in the tumor's vascular niche, termed cancer stem cells (CSCs).

One example is glioblastoma, a prevalent neurological tumor that is universally lethal despite conventional therapy. Glioblastoma ranks as one of the most lethal of all human cancers, with 23,000 cases of glioblastoma diagnosed in the United States each year. Patients diagnosed with glioblastoma have a median survival of less than one year. Current therapeutics includes bevacizumab (Avastin®) an angiogenesis inhibitor and temozolomide (Temodar®) a chemotherapy agent with over $1 billion/year in global sales. While the introduction of temozolomide chemotherapy improved the overall survival of patients with a favourable performance status from 12.1 months to 14.6 months, chemotherapy remains palliative at best. Interestingly, most clinical trials show cohorts of glioblastoma patients who respond well to therapy, but clinicians lack the tools to predict which patients will benefit from a given treatment. Therefore, many patients are exposed to ineffective treatments that cause cytotoxic side effects or, even more worrisome, delay the implementation of more effective therapies. This problem is compounded by the rapid growth in available therapeutic options, with over 356 compounds currently in the pipeline and treatment market growing by 17% annually to $900 million in 2016. Glioblastoma was the first cancer that underwent genetic characterization by the Cancer Genome Atlas. Despite its extensive molecular characterization, glioblastoma remains essentially universally lethal. While a few patients benefitted from molecularly targeted therapies, these molecular predictions have yet to translate into clinical practice.

It is important to note that while genetic and transcriptional screening (i.e. sequencing) permitted the development of molecularly targeted therapies for cancers with a clear driving mutation (e.g. BCR-ABL fusion, or C-KIT activation) such markers haven't been identified for glioblastoma. One alternative to genetic testing is the diagnostic of Circulating Tumor Cell (CTC) in blood samples by Cell-Search® and others. However, while the CTC technology can effectively identify treatment efficacy in breast, colorectal or prostate cancer, it is unable to identify cells in glioblastoma. Therefore, any diagnostic technology that can match patients with beneficial therapeutics would have a tremendous impact on the field and a significant market potential.

Tumors are characterized by a persistent stem cell-like population that does not respond to chemotherapy and can reconstitute the entire tumor population. Therefore, standard of care relies on multiple chemotherapy courses, separated by periods of patient recovery, limiting the number of drugs that can be tested on a given patient. Recent discovery of genetic markers of resistance allows industry to select patient-specific therapies in some clinical situations such as breast, lung and colon cancer. However, many patients don't have specific markers, or have types of cancer (e.g. brain, liver) for which markers have not been identified.

Currently, most in vitro drug screening studies are still performed under conventional two-dimensional (2D) cell culture systems, which are often far from physiological environment of the tumor. Such drug screenings methods may therefore not produce accurate or realistic readouts. Although in vivo experiments are mimicking the real tumor physiological environment, it is time consuming and very expensive to use for high-throughput drug screening, besides that in vivo experiments are hard to use for patient-specific tumor response high-throughput assays. Thus, three-dimensional (3D) in vitro models of human tumors are needed to emulate the tumor physiology and can be used for personalized drug screening assays.

One approach is to isolate patient tumor cells from biopsies or ascites fluid, and screen chemotherapy drugs against the patient own cells. There are dozens of advanced companies that use genetic markers to screen for patient-specific therapies. There are a few companies like CHEMO^{FX} and CureResponse that isolate patient cells from biopsies and screen drugs against them in end-point assays that can't distinguish between Type I (false positive) and Type II (false negative) errors. A false positive result is when drugs appear to respond against the tumor cells but fail to engage its stem cells, and a false negative result is when drugs appear to not have an effect due to the longer time of response by targeting the stem cell population directly.

Prescription drugs and cosmetic ingredients are used over prolong periods of time, ranging from months to decades. This chronic exposure could lead to accumulative toxicity, even in the case of cosmetic ingredients, as molecules or their damage slowly collects over time. Currently, companies identify a no observed effect level (NOEL) in acute exposure models and confirm this lack of effect in an expensive multi-dose response in which animals are exposed to the repeated "safe" dose over 30 to 60-day period. At the end of this evaluation, compounds are considered safe at concentration 10 to 100-fold lower than those assessed. However, as small animal models seldom predict human response, drug safety is still a major concern. In addition, cosmetic ingredient testing in animal has been banned in Europe.

Drug development is currently hampered by the inability of animal experiments to predict human response (Olson 2000; O'Brien 2006), leading to clinical failures and post-market withdrawals costing the industry an estimated $2B annually. In addition, animal testing for cosmetics is no longer possible in Europe (EC no. 1223/2009) limiting development. While emerging organ on chip technology offers to reduce risk using microfluidic models of human tissues, the technology still mostly relies on end-point assays and biomarker measurements to assess tissue damage resulting in limited mechanistic information and difficulties to detect adverse effects occurring at sub-toxic drug exposure, and thus it has thus far failed to show concrete advantages over traditional methods. One of the main challenges lies in detecting idiosyncratic or "unexplained" toxicity occurring due to physiological stress developing below the threshold of cellular damage (Bhatia and Ingber 2014).

Fatty liver disease, steatosis, is a medical condition affecting over 25% of the global population and a common adverse event reported in drug induced liver injury and during prescription drug use. While fatty liver disease can range from simple steatosis to nonalcoholic steatohepatitis (NASH), cirrhosis, and hepatocellular carcinoma, one of the early and more severe forms of the disease is microvesicular steatosis. Microvesicular steatosis is often associated with mitochondrial dysfunction and can be life threatening when long lasting. Drugs associated with microvesicular steatosis include Valproate, Aspirin, glucocorticoids, anti-retroviral drugs (e.g. Stavudine), nonsteroidal anti-inflammatory drugs (e.g. Bromfenac) and cocaine.

Valproate (2-n-propylpentanoic acid) is a widely used antiepileptic drug. Over 40% of the patients on Valproate therapy show elevated liver enzymes, with 61% showing evidence of steatosis based on abdominal ultrasound. Idiosyncratic injury was reported in about 1/20,000 patients and is characterized by microvesicular steatosis developing over weeks of continuous use (Scheffner 1988; Silva 2008; Zimmerman and Ishak, 1982). Valproate toxicity was primarily studied in rodents, showing suppression of β-oxidation and mitochondrial dysfunction as mechanism of action (Zhang 2014), at least in high doses (Tong 2005; Eyer, 2005). Stavudine (d4T) is a nucleoside reverse transcriptase inhibitor used in the treatment of HIV/AIDS. Elevation of liver enzymes was reported in 30% of the patients, with a similar number showing steatosis in ultrasound (Guaraldi 2008; Crum-Cianflone 2009). Stavudine toxicity was similarly studied in rodents and is thought to similarly suppress β-oxidation and induce mitochondrial dysfunction, possibly due to inhibition of mitochondrial mDNA synthesis (Sundar 1997; Akhtar 2008).

Recently, the present inventors demonstrated the real-time measurement of oxygen, glucose and lactate in 3D liver organoids maintained under physiological conditions using tissue-embedded microsensors (Bavli, et al., 2016). Oxygen was measured under flow by phase shift that is independent of signal intensity, and thus unaffected by tissue growth, compaction or death (Schmalzlin 2005; Papkovsky 2004), but amperometric sensors for glucose and lactate had to be microfluidically addressed in a sequential manner, limiting dynamic resolution to once every 80 minutes and overall measurement to 24 hours (Bavli, et al., 2016). The metabolic steady state of this microfluidic design allows to detect small changes and relatively rapid changes in mitochondrial function showing the effect of sub-toxic concentration of troglitazone (Rezulin™) However, this approach come at the price of low throughput, as each microchip can only study a single drug concentration increasing cost and complexity of such dynamic evaluation of function. Other microphysiological platforms also fall short in similar manners when it comes to sampling sensitivity, total period and frequency (Zhang 2017; Weltin 2014), limiting measurement resolution needed to examine sub-toxic drug induced toxicity.

Additional background art includes, but is not limited to A. Ehrlich, M. Ayyash, M. Cohen, S. Tsytkin-Kirschenzweig, K. Ioannidis, A. Riu, R. Note, G. Ouedraogo, G. Vanfleteren, Y. Nahmias. "Microphysiological flux balance platform unravels the dynamics of drug induced steatosis". Lab Chip. 18(17):2510-2522 (2018); Czerniecki S M., et al., 2018. "High-Throughput Screening Enhances Kidney Organoid Differentiation from Human Pluripotent Stem Cells and Enables Automated Multidimensional Phenotyping". Cell Stem Cell 22 (6): P929-940.E4.

SUMMARY OF THE INVENTION

According to an aspect of some embodiments of the present invention there is provided a method of generating an organoid, the method comprising:

forming at an end of a liquid channel a drop of a polymeric solution comprising cells;

while the drop is connected to the end, operating a robotic arm to establish a contact between a surface of the drop and a surface which is characterized by a water contact angle of at least 70 degrees;

releasing the drop from the end; and incubating the drop under conditions that promote formation of the organoid.

According to an aspect of some embodiments of the present invention there is provided a system for generating an organoid, the system comprising:

a surface which is characterized by a water contact angle of at least 70 degrees;

a controllable liquid channel mounted on a robotic arm, and being configured for forming a drop of a polymeric solution comprising cells;

a computerized control system programed to move the robotic arm toward the surface such as to establish a contact between a surface of the drop and the surface, and to control the controllable liquid channel to release the drop once the contact is established.

According to an aspect of some embodiments of the present invention there is provided a multi-well plate comprising an array of wells each containing a distinct organoid therein, wherein a size of each organoid is within less than 20% or less than 15% or less than 10% from an average size of all organoids occupying the multi-well plate.

According to an aspect of some embodiments of the present invention there is provided an in vitro method of screening an agent for treating cancer, comprising:

generating multiple tumor organoids from a tumor biopsy of a subject on at least a few wells of a multi-well plate, wherein each well of the at least a few wells comprises at least one tumor organoid, and wherein each of the tumor organoids comprises at least one oxygen sensor, contacting at least one of the tumor organoids with the agent, and measuring percentage of oxygen in each of the tumor organoids following the contacting, wherein an increase in the percentage of oxygen following the contacting as compared to prior to the contacting is indicative that the agent is suitable for treating the cancer, thereby screening the agent suitable for treating the cancer of the subject.

According to an aspect of some embodiments of the present invention there is provided a method of determining a dose range of a pharmaceutically active agent to be administered for treating a disease or condition, the method comprising:

incubating a plurality of organoids with a respective plurality of different concentrations of the agent;

monitoring function of the organoids over a time period to determine, for each organoid, a time-to-onset (TTO) of a response of the organoid to the agent, thereby providing a plurality of TTO values, one for each of the concentrations;

fitting the plurality of TTO values to an asymptotic function;

extracting an asymptotic value from the asymptotic function; and determining a range of a dose amount based on the extracted asymptotic value.

According to an aspect of some embodiments of the present invention there is provided a method of determining a toxicity of a pharmaceutically active agent to be administered for treating a disease or condition, the method comprising:

incubating a plurality of organoids with a respective plurality of different concentrations of the agent;

measuring function of the organoids at a time point, thereby providing a plurality of organoid-function values, one for each of the concentrations, wherein a time-period from a beginning of the incubation to the time point corresponds to a pre-selected exposure time of a subject to the agent;

fitting the plurality of organoid-function values to an S-shaped curve; and extracting from the S-shaped curve a predicted toxicity value of the agent for the pre-selected exposure time.

According to some embodiments of the invention, the surface is a hydrophobic surface.

According to some embodiments of the invention, the surface is a base of a well.

According to some embodiments of the invention, the surface is a hydrogel coating a base of a well, preferably a hydrophobic hydrogel.

According to some embodiments of the invention, the well is one of a multi-well plate, and the method is repeated for each of at least a few wells of the plate.

According to some embodiments of the invention, the drop is from about 0.2 to about 5 microliters in volume.

According to some embodiments of the invention, the drop is from about 0.8 to about 1.4 microliters in volume.

According to some embodiments of the invention, forming the drop is at a rate of from about 1 to about 100 microliters per second.

According to some embodiments of the invention, releasing the drop is executed when a distance between the end and the surface is less than a diameter of the drop.

According to some embodiments of the invention, releasing the drop is executed when a distance between the end and the surface is from about 0.16 to about 0.2 mm less than a diameter of the drop.

According to some embodiments of the invention, releasing the drop is executed when a distance between the end and the surface is about 0.18 mm less than a diameter of the drop.

According to some embodiments of the invention, the polymer of the polymeric solution is a natural polymer.

According to some embodiments of the invention, the polymer of the polymeric solution is a synthetic polymer.

According to some embodiments of the invention, the cells contained in the polymeric solution are provided at a concentration of $1 \times 10^5$ to $1 \times 10^9$ cells/mL (milliliter).

According to some embodiments of the invention, the polymeric solution further comprises an oxygen sensor.

According to some embodiments of the invention, the oxygen sensor is provided at a concentration of 0.1-10 mg (milligram) per milliliter of the polymeric solution.

According to some embodiments of the invention, releasing the drop from the end is performed once per each well such that a single organoid is generated in each well.

According to some embodiments of the invention, controlling the robotic arm is by a computerized control system pre-programed to ensure that the contact is established.

According to some embodiments of the invention, the computerized control system is configured to receive position data pertaining to a height of the robotic arm above the surface, and to move the robotic arm responsively to the position data.

According to some embodiments of the invention, the method further comprising applying a culture medium to the organoid generated on the well.

According to some embodiments of the invention, the organoid comprises at least one oxygen sensor.

According to some embodiments of the invention, the at least one oxygen sensor is embedded within each of the organoids.

According to some embodiments of the invention, the oxygen sensor comprises an optical sensor patch.

According to some embodiments of the invention, the oxygen sensor comprises an optical sensor probe.

According to some embodiments of the invention, each well of the at least a few wells comprises a single organoid.

According to some embodiments of the invention, presence of an oxygen plateau of about 21% oxygen over a predetermined time period in the tumor organoids is indicative that the agent is a suitable drug for killing of proliferating cancer cells and cancer stem cells comprised in the tumor organoid.

According to some embodiments of the invention, the predetermined time period is at least 48 hours.

According to some embodiments of the invention, the predetermined time period is at least 72 hours.

According to some embodiments of the invention, the predetermined time period is at least 96 hours.

According to some embodiments of the invention, the measuring is continuous.

According to some embodiments of the invention, the drug is a chemotherapeutic drug.

According to some embodiments of the invention, the drug is an immunotherapy drug.

According to some embodiments of the invention, the drug is a small molecule.

According to some embodiments of the invention, the cancer is selected from the group consisting of: glioblastoma, liver cancer, lung cancer, breast cancer, brain cancer, colorectal cancer, and prostate cancer.

According to some embodiments of the invention, the cancer is glioblastoma.

According to some embodiments of the invention, the drug is selected from the group consisting of omacetaxine mepesuccinate and bortezomib.

According to some embodiments of the invention, generating multiple tumor organoids is performed by a method comprising:

forming at an end of a liquid channel a drop of a polymeric solution comprising tumor cells and oxygen sensors;

while the drop is connected to the end, establishing a contact between a surface of the drop and a surface which is characterized by a water contact angle of at least 70 degrees, wherein the surface is a base of the multi-well plate or a hydrogel coating a base of the multi-well plate, preferably a hydrophobic hydrogel;

releasing the drop from the end; and incubating the drop conditions that promote formation of the tumor organoid.

According to some embodiments of the invention, establishing is operated by a robotic arm.

According to some embodiments of the invention, repeating the method for each of at least a few wells of the multi-well plate.

According to some embodiments of the invention, monitoring is in the absence of flow of the agent to and from the organoids.

According to some embodiments of the invention, incubation is simultaneous for all organoids.

According to some embodiments of the invention, incubating is within bioreactors under condition of a steady flow of the agent to the organoids.

According to some embodiments of the invention, monitoring the function, comprises monitoring oxygen levels.

According to some embodiments of the invention, monitoring the viability, comprises monitoring cellular metabolic levels.

According to some embodiments of the invention, the organoids are embedded with oxygen sensors, and wherein the monitoring the oxygen levels comprises monitoring signals emitted by the oxygen sensors.

According to some embodiments of the invention, the time period is at least 10 hours.

According to some embodiments of the invention, the time period is at least 24 hours.

According to some embodiments of the invention, the asymptotic function, is an asymptotically decaying function.

According to some embodiments of the invention, the asymptotic function, is an exponential function.

According to some embodiments of the invention, the asymptotic function, is a non-exponential function.

According to some embodiments of the invention, determining the dose range comprises selecting a dose range such that a peak plasma concentration of the agent in a blood sample of a test subject administered with the agent is less than the asymptotic value.

According to some embodiments of the invention, incubating the organoids is executed in a multi-well plate.

According to some embodiments of the invention, the method comprising receiving a value describing a dose amount, and using the asymptotic function for determining an exposure time to the agent, the exposure time being a TTO of a response of an organoid to the agent, had the organoid been incubated with a concentrations of the agent that correspond to the dose amount.

According to some embodiments of the invention, the method comprising repeating the measuring, the fitting, and the extracting at least once, at a different time point corresponding to a different expected exposure time, thereby providing a plurality of toxicity values, one for each expected exposure time.

According to some embodiments of the invention, the method identifying a plateau over the toxicity values, as a function of time, and extrapolating the plateau to determine a toxicity value for an exposure time that is longer than each of the exposure times.

According to some embodiments of the invention, measuring is in the absence of flow of the agent to and from the organoids.

According to some embodiments of the invention, the measuring is simultaneous for all organoids.

According to some embodiments of the invention, incubating is within bioreactors under condition of a steady flow of the agent to the organoids.

According to some embodiments of the invention, measuring the function comprises measuring oxygen levels.

According to some embodiments of the invention, measuring the viability comprises measuring oxygen levels.

According to some embodiments of the invention, the organoids are embedded with oxygen sensors, and wherein the measuring the oxygen levels comprises measuring signals emitted by the oxygen sensors.

According to some embodiments of the invention, the asymptotic function, is an asymptotically decaying function.

According to some embodiments of the invention, the S-shaped curve is a sigmoid.

According to some embodiments of the invention, the sigmoid is $a_1 + a_2/[1 + (c/a_3)^h]$, where $a_1$, $a_2$, $a_3$ and h are sigmoid parameters, and c represents the different concentrations, and wherein $a_3$ represents the toxicity of the agent.

According to some embodiments of the invention, the $a_1$ and $a_2$ are predetermined and wherein the fitting comprises applying a two-parameter fit to provide a value for the $a_3$ and the h.

According to some embodiments of the invention, the $a_1 = 0$.

According to some embodiments of the invention, the $a_2 = 1$.

According to some embodiments of the invention, the toxicity is $TC_{50}$.

According to some embodiments of the invention, the incubating the organoids is executed in a multi-well plate.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWING(S)

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-E depict a water drop placed on various commercial surfaces with the indicated contact angels between the liquid-vapor interface and the solid surface. Contact angle quantifies the wettability of a solid surface by a liquid via the Young-Dupré equation. A summary of some experiments is provided in Table 4 (Example 1 of the Examples section which follows).

FIGS. 2A-H depict a high throughput generation of 3D micro-tumors of the glioblastoma cell line U87. Proprietary robotic liquid handling technology permits the rapid formation of 3D micro-tissues in standard 384-well plates. The micro-Tissues form in hours and stabilize in 3-4 days. FIGS.

2A-B shows a fully formed glioblastoma micro-tumor after 24 hours of culture. FIGS. 2C-H are fluorescent microscopy images showing oxygen micro-sensors (red dots) embedded in Calcein-AM-stained tissue (green staining). Calcein-AM is a non-fluorescent dye that is hydrolyzed in living cells by intracellular esterase to green-fluorescent calcein. Thus, the staining shows oxygen sensors embedded in living tissues.

FIGS. 3A-F depict complex sensor-embedded micro-tissues. Organoids were generated on a multi-well plate according to the method of some embodiments of the invention and the organoids were further subjected to immuno-staining analysis. FIG. 3A—liver micro-tumor composed of HepG2/C3A hepatocellular carcinoma cells (green=Calcein-AM live cells; red=oxygen micro-sensors); FIG. 3B—Human liver organoid composed of albumin positive $E6/E7^{LOW}$ hepatocytes and CD31 positive endothelial cells (blue=albumin; red=CD31); FIG. 3C—human liver organoid as in FIG. 3B (blue=Hoechst stain; orange=oxygen microsensors); FIG. 3D—Patient-derived glioblastoma micro-tumor mixed with CD31 positive endothelial cells (Red=OLIG2; Green=CD31; Pink=SOX2); FIG. 3E—Human mini-brain composed of iPSC-derived neural stem cells mixed with CD31 positive endothelial cells (Green=Cell Tracker dye labeling iPSC-derived neuronal stem cells; red=CD31); FIG. 3F—Human mini-brain (phase microscopy).

FIG. 4 schematically depicts various methods of generating organoids. (1) The hanging drop method; (2) Random deposition of cells on ultra-low attachment (ULA) surface resulting in random organoids of various sizes; (3) Random deposition of cells in a polymer hydrogel resulting in random organoids of various sizes; and (4) The method of some embodiments of the invention distinct organoids are formed, having a homogenous size and cell number.

FIGS. 5A-E depict a personalized micro-tumor screening. Patient-derived sensor-embedded tumors are screened using high throughput kinetics against FDA-approved oncology drugs. FIGS. 5A-B show a schematics of tumor biopsy (FIG. 5A) comprising proliferating cells (marked in orange) and cancer stem cells (marked in green) seeded in a multi-well plate with oxygen sensors embedded therein (FIG. 5B) and cultured for 3-4 days in the presence of multiple FDA-approved oncology drugs. FIGS. 5C-E show cyto toxicity in percentages of the cells within the micro-tumor tissue over time in the presence of the drugs. Cytotoxicity is calculated from the percentage of oxygen out of air as measured by the oxygen sensors within the micro-tumor tissue, wherein 100% of oxygen is equal to 21% oxygen in air. When the percentage of oxygen is 100% it means that all cells in the microtumor cease to consume oxygen, thus they are dead. FIG. 5C shows a positive response of the tumor cells to the drug, as manifested by a stable cell death over time. FIG. 5D shows a false negative response to a drug as manifested by the late response to the drug, which begins after 48 hours, probably due to damage to the cancer stem cell population. FIG. 5E shows a false positive response to a drug as manifested by the positive response to the drug (cell death) following 12 hours, with a peak at 24 hours, and then a recovery of the tumor cells, probably due to the survival cancer stem cells, which results in continued proliferation of the tumor cells. Thus, the screening method of some embodiments of the invention can distingue between a true positive response and a false negative or a false positive response, thus, eliminating type I/II error in drug-screening for treatment of cancer.

FIG. 6 is a graph depicting effects of NIH FDA approved Drugs (at a concentration of 5 µM) on U87-MG spheroids.

Each line represents the presence of oxygen in the micro-tumor tissue demonstrating toxicity as a function of time in response to the different drugs.

FIGS. 7A-F are graphs depicting positive (FIGS. 7A-B), false negative (FIGS. 7C-D) and false positive (FIGS. 7E-F) effects of various drugs on U87-MG cells embedded in collagen gel (red and blue lines) or basement membrane gel (purple and green lines). Each line represents a different experimental repeat. Each drug was used at a concentration of 5 µM. The tumor cells were grown on multi-well plate with oxygen sensors embedded therein according to the method of some embodiments of the invention. FIG. 7A—Omacetaxine mepesuccinate; FIG. 7B—Bortezomib; FIG. 7C—Romidepsin; FIG. 7D—Daunorubicin hydrochloride; FIG. 7E-Dactinomycin; FIG. 7F—Erismodegib.

FIGS. 8A-D are images depicting a live/dead assay of U87-MG cells following 2 days of treatment with the indicated drugs. Live cells are shown in green; dead cells are shown in red. Note that the positive drugs primarily affect the micro-tumor interface between the hypoxic and proliferative regions where cancer stem cells are thought to persist.

FIGS. 9A-B depict a patient-derived glioblastoma micro-tumor formed by a mixture of proliferating patient-derived cancer stem cells expanded under serum free conditions and CD31 positive endothelial cells. Micro-tumors stabilize in 4 days and show strong staining for both SOX2 and OLIG2 putative cancer stem cells markers.

FIGS. 10A-C depict real time oxygen flux analyzer. Tissue embedded micro-sensors permit continuous, focus-independent, high sensitivity, real time monitoring of oxygen consumption. FIG. 10A is a prototype desktop device capable of identifying and reading organoids oxygen concentration in real time according to some embodiments of the invention. FIG. 10B is an image of sensors embedded in a liver organoid (Orange=oxygen micro-sensors; blue=Hoechst). FIG. 10C is a graph depicting the levels of oxygen (% of air) in human liver organoid composed of E6/E7$^{LOW}$ hepatocytes and endothelial cells in the presence of increasing concentrations of a chemotherapeutic drug (Thapsigargin) over time. Note that the onset of damage starts 8 to 24 hours after exposure suggesting indirect damage due to a slow accumulation of metabolites rather than a direct toxic effect of the molecule or its derivatives.

FIGS. 11A-C depict a time-dependent view of toxicity to Valproate measured using oxygen micro-sensors. FIG. 11A—The graph shows the time dependent response of liver organoid composed HepG2/C3A cells to various concentrations of Valproate as indicated by a color index. Each line represents the presence of oxygen in the liver micro-tissue demonstrating toxicity. FIG. 11B—Vertical cross-sections of the data in FIG. 11A showing liver organoid toxicity at 24 hours (red circles) and 42 hours (green cubes). Note that accumulative toxicity caused by valproate shows that the TC$_{50}$ value marking 50% death decreases from 27 to 14 mM over the span of those 18 hours. FIG. 11C—The kinetic measurements of toxicity in FIG. 11A allow to present a graph of TC$_{50}$ value marking 50% death as a function of time. Thus it is noted that the TC$_{50}$ value plateau out at a value of around 5 mM, which is a five-fold lower concentration than the standard value measured as 24 hours.

FIGS. 12A-C depict a time-dependent view of toxicity to Valproate measured using oxygen micro-sensors. Horizontal sections segregate direct from indirect effects, and analytically derive the lowest exposure level (LEL). FIG. 12A—same as FIG. 11A. FIG. 12B—Time to onset (TTO) of response of differentiated HepG2/C3A organoids to valproate showing a dose-dependent decrease in TTO ranging from 6-36 hours suggesting slowly accumulative steatotic damage. FIG. 12C—Analytical derivation of lowest exposure level (LEL) using the time to onset-dependent flux accumulation equation. LEL was defined as the horizontal asymptote, concentration for which onset of damage is at infinite time. Valproate shows LEL of 280±97 micromolar close to clinically reported Cmax. All error bars indicate ±standard error.

FIGS. 13A-F. Tissue-embedded microsensors show prolonged accumulative damage and analytical derivation of no observed effect levels in steatosis-inducing drugs. FIG. 13A—Representative oxygen uptake over time response of differentiated HepG2/C3A organoids exposed to increasing concentrations of Valproate and Stavudine. Dotted line notes exposure onset. FIG. 13B—Dose-dependent toxicity curves of differentiated HepG2/C3A organoids treated with Valproate and Stavudine. TC$_{50}$ for Valproate ranged from 27 mM at 24 hours to 14 mM at 42 hours. TC$_{50}$ for Stavudine ranged from 4.3 mM at 24 hours to 1.7 mM at 42 hours. FIG. 13C—Time to onset (TTO) of response of differentiated HepG2/C3A organoids to Valproate and Stavudine. Both drugs showed a dose-dependent decrease in TTO ranging from 6-36 hours in Valproate to 10-29 hours for Stavudine suggesting slowly accumulative steatotic damage. FIG. 13D—Fluorescence micrographs and FIG. 13E—Quantification of steatosis and phospholipidosis in differentiated HepG2/C3A organoids as a result of exposure to different drugs. (***P<0.001; n=9). n represent the number of experimental repeats. Scale bar=200 µm. FIG. 13F—Analytical derivation of lowest exposure level (LEL) using the time to onset-dependent flux accumulation equation. LEL was defined as the horizontal asymptote, concentration for which onset of damage is at infinite time. Valproate and Stavudine showed LEL of 280±97 and 4±1 µM, respectively, close to clinically reported C$_{max}$. All error bars indicate ±standard error. TC$_{50}$ and LEL error calculated by curve fitting.

FIGS. 14A-G depict formation and characterization of patient-derived glioblastoma microtumors. FIG. 14A—Schematic depiction of the generation of GBM microtumors from patient-derived cancer stem-cells (CSCs). FIG. 14B—Representative phase and FIG. 14C—immunofluorescent depictions of patient-derived glioblastoma microtumors created from isolated cancer stem cells and endothelial cells seeded in precise microenvironments. Endothelial cells form vascular networks throughout the microtumor, with higher representation in the tumor's periphery, similar to the in vivo morphology of GBM tumors. Cancer stem cells differentiate to form heterogeneous complex micro-tumor recapitulating GBM tumors cancer stem cells and differentiated cancer cells (DCC) microstructures seen in biopsies. FIG. 14D—immunofluorescence of cancer stem cell functional markers OLIG2 and SOX2 showing heterogeneous population and differentiative state among the micro-tumors cancer stem cells, recapitulating characteristics and expression patterns seen in GBM tumors biopsies. FIG. 14E—Confocal immunofluorescent image and FIG. 14F—heatmap representing cancer stem-cells distribution along the tumor. FIG. 14G—Limiting dilution assay to quantify functional stem cell frequency within separated micro tumor niche populations.

FIG. 15 depicts the effects of 129 FDA-approved drugs, used at a concentration of 5 µM on two different patient-derived GBM cell populations (lines 1914 and 1919). Cancer stem cells were isolated from GBP biopsies obtained for pathological evaluation under informed consent. Samples were deidentified and expanded in serum free media maintaining the SOX2 and OLIG2 stem cell phenotype. Cells were deposited as GBP cancer organoids in Matrigel with embedded with oxygen sensing beads on 384-well plates using method depicted above. Each line represents the presence of oxygen in the micro-tumor tissue demonstrating toxicity as a function of time in response to a different drug. Data shows 4 and 6 drugs producing a positive response in patients 1919 and 1914, respectively. Positive response was manifested by stable cell death overtime as schematically depicted in FIG. 5C. Both populations also show false negative response to drug manifested by late response to the drug, beginning after 30 to 48 hours from exposure as schematically depicted by FIG. 5D. Both populations also show false positive response manifested by cell death, followed by recovery of the tumor cells, probably due to the survival of cancer stem cells as schematically depicted in FIG. 5E.

FIGS. 16A-J depicts kinetic assessment of micro-tumors in a precise, high-content manner. FIG. 16A—Schematic depiction of the generation of glioblastoma (GBM) micro-tumors. FIG. 16B—Scheme explaining the novel approach developed in order to seed and from precise, repeatable and high-content formation of microtumors. Matrix drops are distributed with precise volume to create identical half-sphere microenvironments to allow uniform formation of micro-tumors. Cells are seeded in a precise microenvironment form micro-tumors serially with minimal variability to create uniform micro-tumors while regular seeding methods create random structures limiting the cells ability to self-organize into a tumor-like tissue. FIG. 16C—Representative images depicting the automated process conducted by a Biomek 5 liquid handler to create uniform microenvironments to allow consistent formation of micro-tumors. FIG. 16D—Representative phase and FIG. 16E—Live/Dead images of the development of GBM microtumors in defined microenvironments in 384 well plate. Cells form dense micro-tumors, metastasizing across the well. FIG. 16F—Dynamic oxygen uptake response of U87 GBM micro-tumors exposed to 126 different FDA approved cancer drugs. FIG. 16G—Heat map of 72 hours post-exposure viability of U87 GBM micro-tumors expose exposed to 126 different FDA approved cancer drugs. FIG. 16H—Schematic depiction of assessment of toxicity results in kinetic measurement in comparison to end point viability assessment. Drugs with high time to onset (duration until effect takes place) and drugs with adaptive response will provide false results (false negative and false positive, in respect), creating bias assessment of drug effectivity. FIG. 16I—Representative Dynamic oxygen uptake response in two drugs, each line represent the mean of oxygen in a separate experiment, and FIG. 16J—Live/Dead micrographs of U87 GBM micro-tumors exposed to different FDA approved cancer drugs. Response indicates that early response drugs damage the main tumor, however, the tumor remains malignant, able to metastasize across the well. Late reposing drugs, that would have been missed in standard screens, eradicate both the main tumor and the metastases.

Figures 2A, 2B, 2C, 2D, 2E, 2F, 2G, 2H:
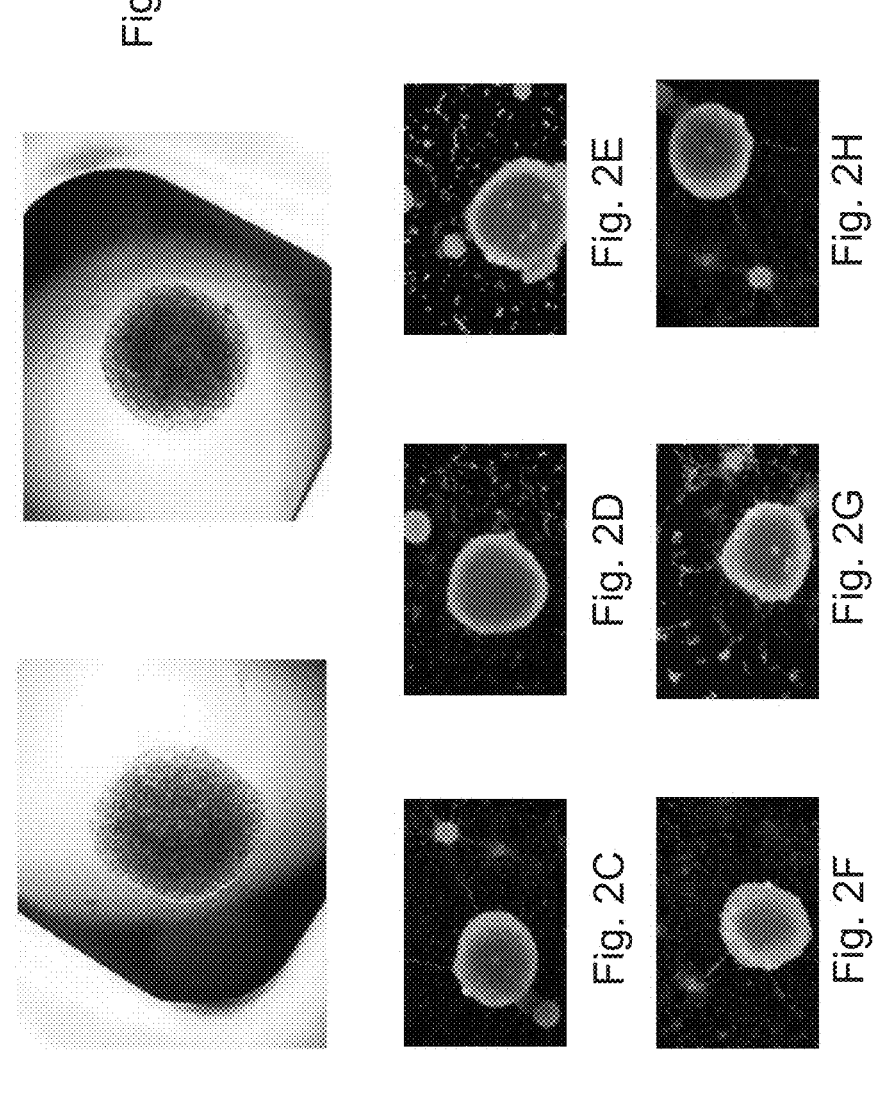
Figures 3A, 3B, 3C, 3D, 3E, 3F:
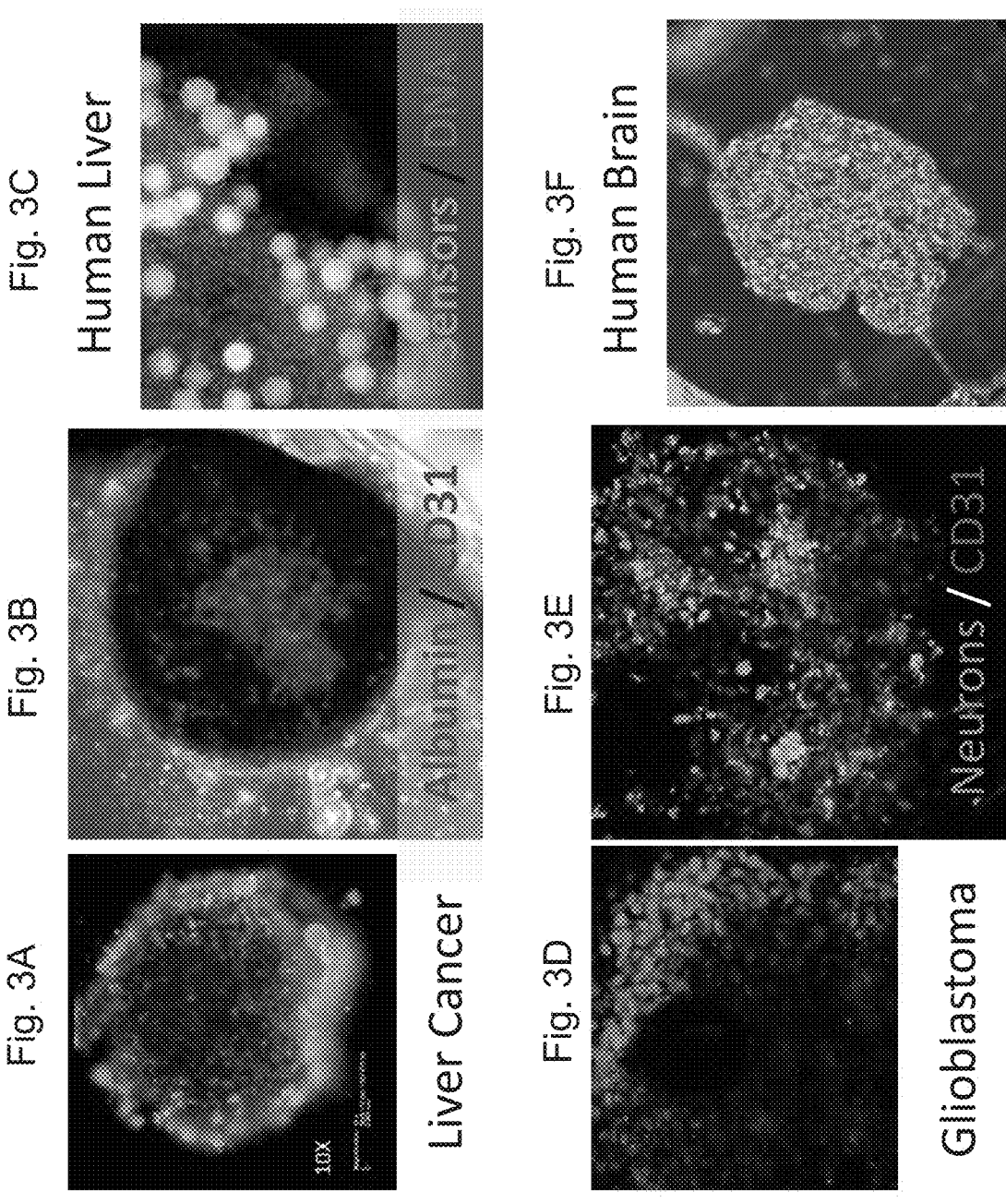
Figure 4:
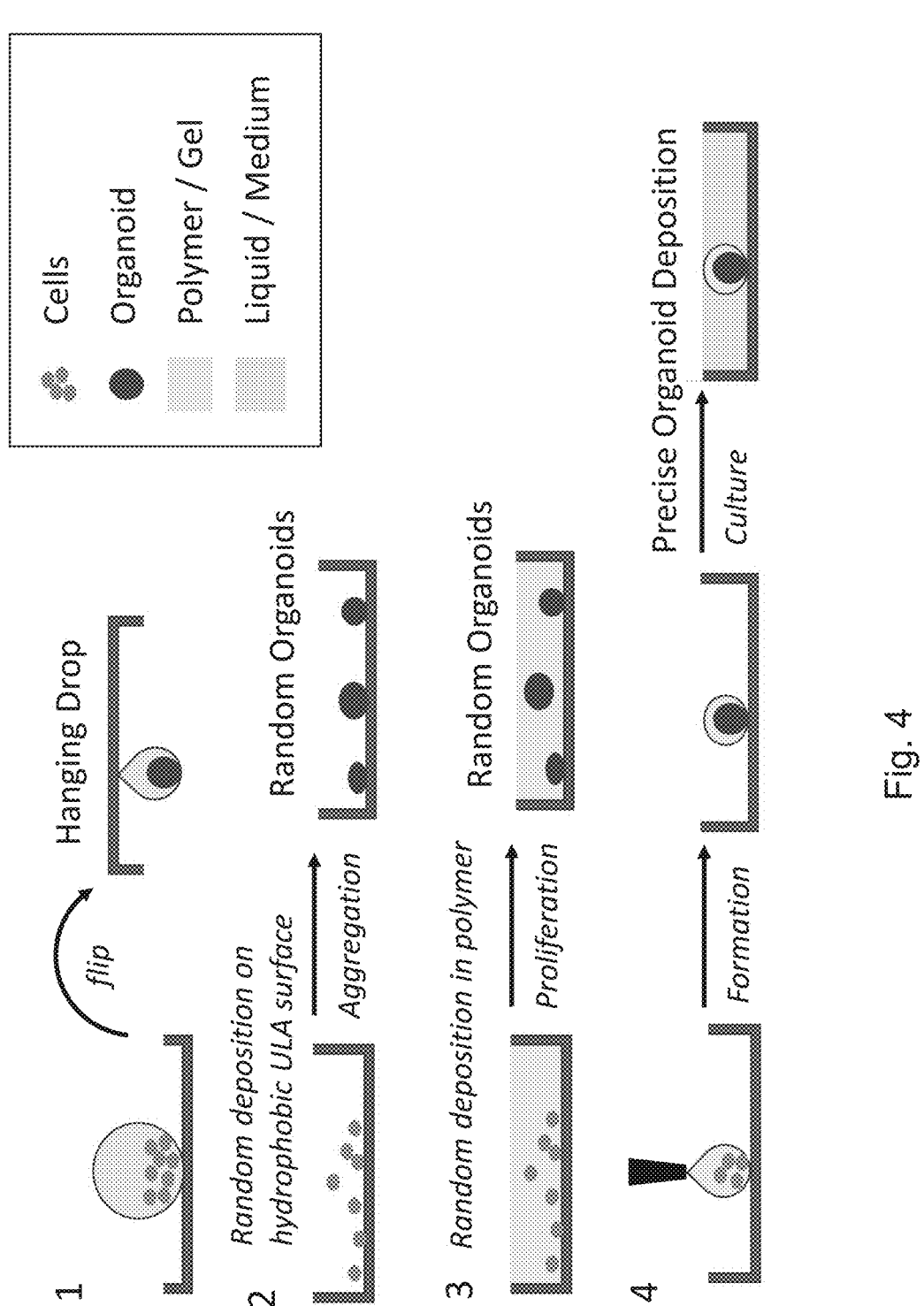
Figure 6:
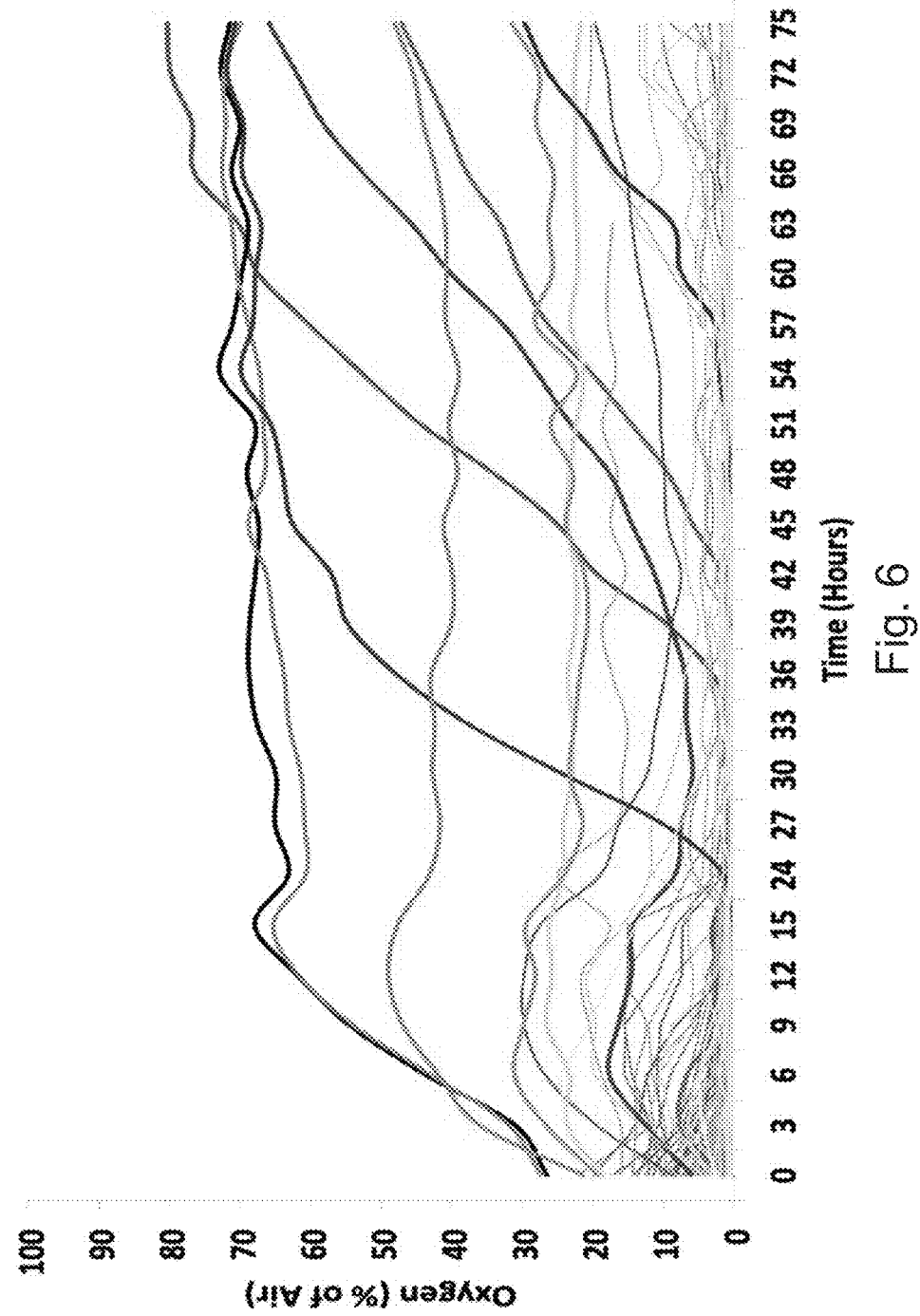
Figures 8A, 8B, 8C, 8D:
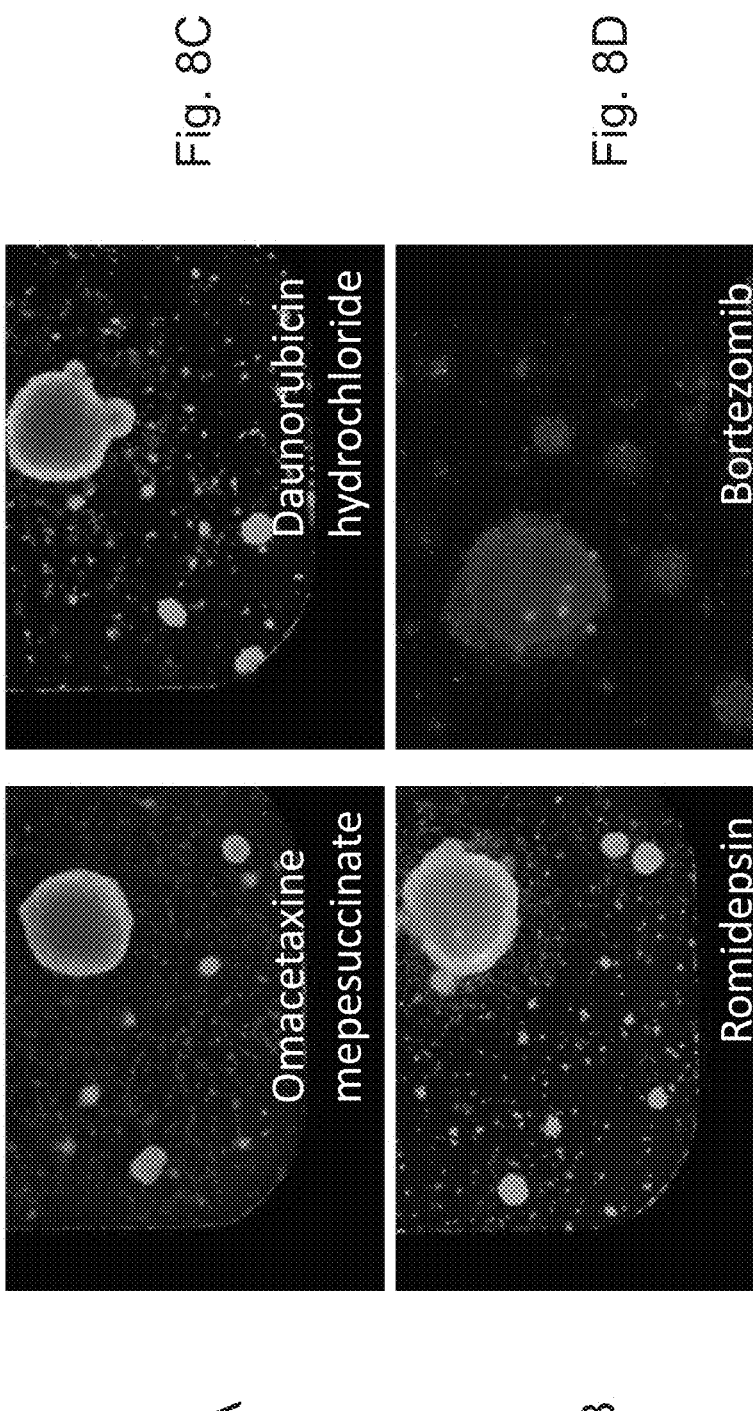
Figure 9B:
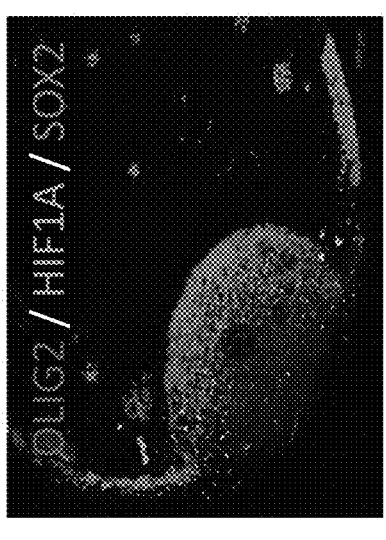
Figure 9A:
Figures 11A, 11B, 11C:
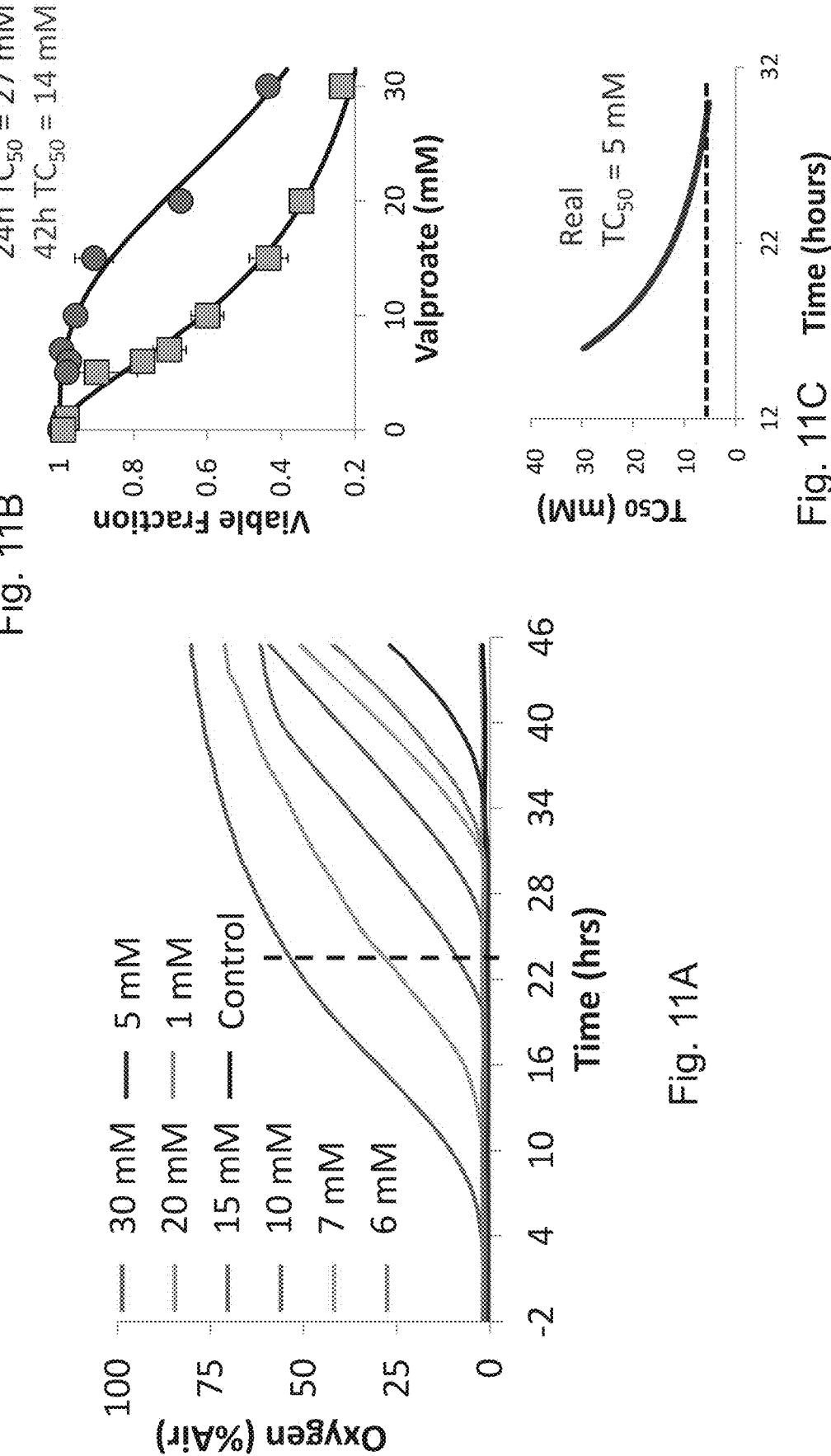
Figures 12A, 12B, 12C:
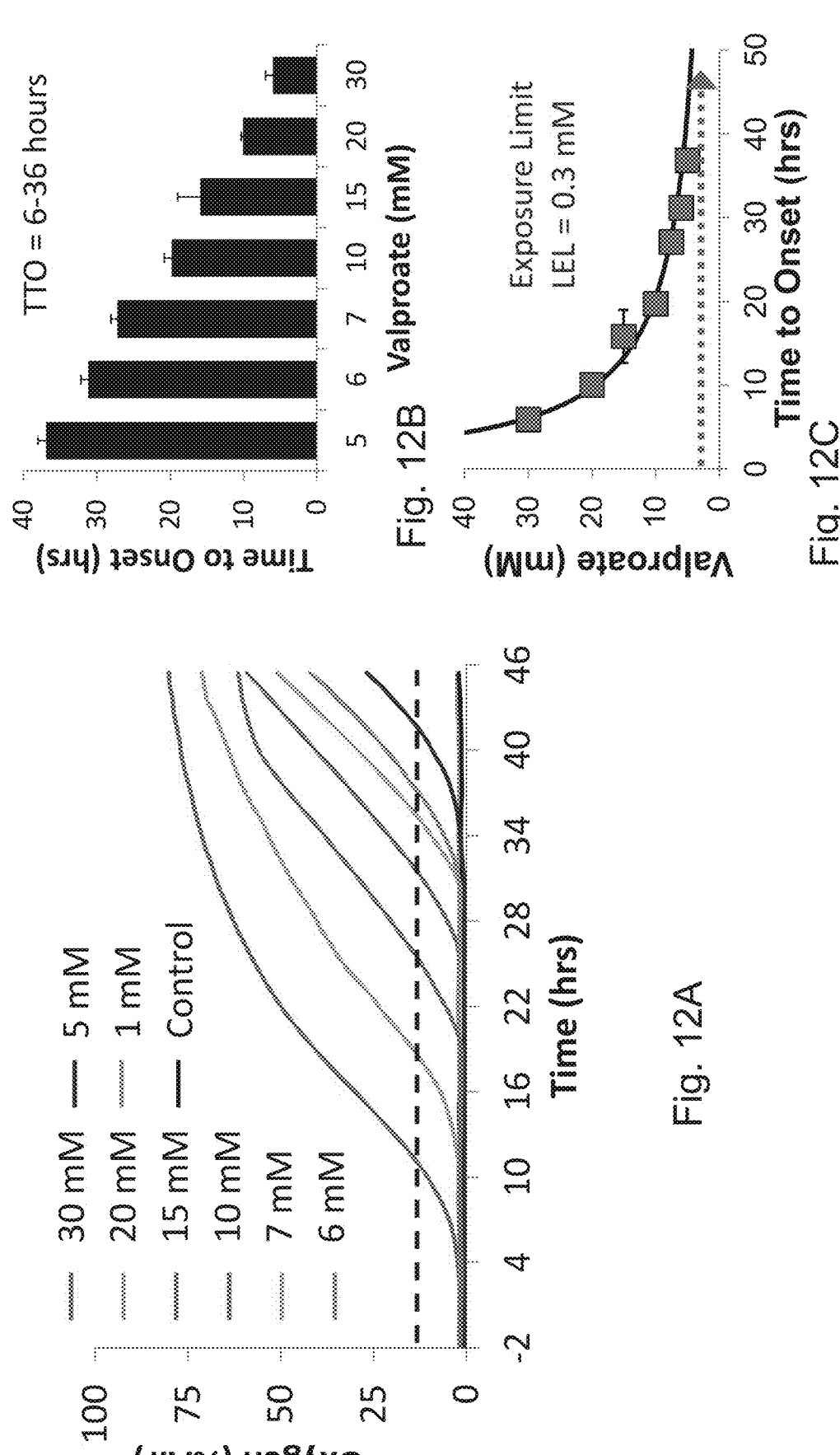

FIGS. 19A-D are schematic illustrations of a system suitable for generating an organoid, according to some embodiments of the present invention.

DESCRIPTION OF SPECIFIC EMBODIMENTS OF THE INVENTION

The present invention, in some embodiments thereof, relates to methods of generating organoids on a multi-well plate, methods of drug screening using said organoids and methods of determining treatment regimens for various drugs using organoids.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The approach according to some embodiments of the invention, which was uncovered by the present inventors for generation of organoids, relies on the careful deposition of a droplet of cells in polymerizing gel such as collagen or Matrigel on a surface having a contact angle $\theta > 70°$, e.g., a contact angle $\theta > 80°$. Under these conditions the droplet polymerizes in place in 15 to 60 minutes and does not get smeared out. Cellular contractility then takes over and the organoid contracts over 12 to 72 hours. In this way, the present inventors are able to control the exact number and type of cells in each organoid, and to obtain highly repeatable organoid size and functional behavior.

This is in contrast to ULA surfaces where organoids vary in size and mixture. It is also much easier to carry out and automate than the hanging drop transfer method produced by InSphero as it does not require multiple plastic parts.

According to an aspect of some embodiments of the invention there is provided a method of generating an organoid. The method can be executed, at least in part, by a system 30 schematic illustrated in FIGS. 19A-D. The method comprises forming at an end 32 of a liquid channel 34 a drop 36 of a polymeric solution 38 comprising cells 40;

while drop 36 is connected to end 32, operating a robotic arm 42 to establish a contact between a surface of drop 36 and a surface 44 which is characterized by a water contact angle $\theta$ of at least 70 degrees, and releasing drop 36 from end 32.

According to some embodiments of the invention, drop 36 is released when a distance between end 32 and surface 44 is less than a diameter of drop 36 (FIG. 19B). For example, drop 36 can be released when the distance between end 32 and surface 44 is from about 0.16 to about 0.2 mm less than the diameter of drop 36, or from about 0.17 to about 0.19 mm less than the diameter of drop 36, e.g., about 0.18 mm less than the diameter of drop 36.

The advantage of releasing drop 36 when the distance between end 32 and surface 44 is less than the diameter of drop 36, is that it allows controlling the geometry of the microtissues that are created on the surface 44. For example, releasing drop 36 when the distance between end 32 and surface 44 is lightly less than the diameter of drop 36 (e.g., from about 0.17 to about 0.19 mm, less than the diameter of drop 36), can ensure that geometrically even microtissues are created.

The method further comprises incubating drop 36 under conditions that promote formation of an organoid 50.

As used herein the term "organoid" refers to an artificial organ model (generated in vitro) comprising an aggregate of live cells in a three-dimensional or multi layered configuration manufactured by culturing cells in a three-dimensional form.

The organoid may have a suffix of "organ" and the meaning of 'similar to organ'. Organoids may comprise one differentiated cell type, or two or more differentiated cell types, depending upon the particular tissue or organ being modeled or emulated.

According to some embodiments of the invention, the organoid can carry out at least one function of the organ.

According to some embodiments of the invention, the organoid is an organ model of a tissue such as liver, heart, brain, gut, kidney, or bone.

According to some embodiments of the invention, the organoid is an organ model of a cancer tumor, such as glioblastoma, or hepatocellular carcinoma.

According to some embodiments of the invention, the organoid comprises hepatic cells.

According to some embodiments of the invention, the organoid comprises hepatic cells and endothelial cells.

According to some embodiments of the invention, the organoid further comprises fibroblasts.

According to some embodiments of the invention, the organoid comprises enterocytes.

According to some embodiments of the invention, the organoid further comprises endothelial cells.

According to some embodiments of the invention, the organoid comprises enterocytes and endothelial cells.

According to some embodiments of the invention, the organoid comprises cardiomyocytes and endothelial cells (e.g., capable of beating).

According to some embodiments of the invention, the organoid comprises pancreatic (beta cells) (e.g. can secrete insulin).

According to some embodiments of the invention, the organoid comprises pancreatic (beta cells), and endothelial cells.

According to some embodiments of the invention, the organoid comprises pancreatic (beta cells), endothelial cells and fibroblasts.

According to some embodiments of the invention, the organoid comprises neural cells (e.g. neural progenitors).

According to some embodiments of the invention, the organoid comprises neural cells (e.g. neural progenitors) and endothelial cells.

The water contact angle θ is defined as the angle between an horizontal solid surface and an inner surface of a liquid water drop at the three phase boundary where the liquid water, gas and solid intersect. A higher hydrophobicity of a solid leads to a higher water contact angle with a liquid droplet sitting up with a more spherical shape.

The contact angle can be measured, for example, using a Contact Angle Goniometer.

In some embodiments of the present invention the surface is characterized by a water contact angle of at least 70°, in some embodiments of the present invention the surface is characterized by a water contact angle of at least 80°, in some embodiments of the present invention the surface is hydrophobic, and in some embodiments of the present invention the surface is super-hydrophobic.

As used herein, a "hydrophobic surface" refers to a surface that is characterized by a water contact angle of at least 90 degrees.

As used herein, a "super-hydrophobic surface" refers to a surface that is characterized by a water contact angle of at least 130 degrees.

Thus, embodiments of the present invention also contemplate a surface that is characterized by a water contact angle greater than 80 degrees, or greater than 90 degrees, or greater than 100 degrees, or greater than 110 degrees, or greater than 120 degrees, or greater than 130 degrees, or greater than 140 degrees.

High water contact angle, e.g., hydrophobicity, can be achieved through various materials and material configurations for the substrate. In some embodiments, the substrate can be formed from a chemically hydrophic material or can comprise a surface layer formed from a chemically hydrophobic material. Chemically hydrophobic materials typically comprise nonpolar molecular structures that are incapable of forming hydrogen bonds with water. Introduction of such a non-hydrogen bonding surface to water causes disruption of the hydrogen bonding network between water molecules. The hydrogen bonds are reoriented tangentially to such surface to minimize disruption of the hydrogen bonded 3D network of water molecules and minimize the water-hydrophobe interfacial surface area. Examples of chemically hydrophobic materials include but are not limited to polyethylene, polypropylene, or polytetrafluoroethylene (PTFE). Hydrophobicity can also be provided through surface coating such as polyurethane or other hydrophobic coatings or by micro- or nano-sized features on the substrate surface. In some embodiments, the surface has hierarchical surface roughness with nanoscale or microscale structural or roughness features imparting a hydrophobic or superhydrophobic property to the surface. In some non-limiting examples, the microscale roughness may have Ra surface roughness values ranging from approximately 5 microns to approximately 100 microns and the nanoscale roughness may have an Ra value ranging from approximately 250 nanometers to approximately 750 nanometers. Surface roughness can be provided by chemical etching, spray coating, or sintering.

According to some embodiments of the invention, surface 44 is a hydrophobic surface.

According to some embodiments of the invention, surface 44 is a base of a well 48.

According to some embodiments of the invention, the surface 44 is a hydrogel coating a base of well, 48 preferably a hydrophobic hydrogel.

According to some embodiments of the invention, well 48 is one of a multi-well plate, and the method is repeated for each of at least a few wells of said plate.

As used herein and in the claims section which follows the term "few" refers to more than one well, e.g., at least 2 wells, e.g., at least 3, at least 4, at least 5, at least 6, at least 7, at least 8, at least 9, at least 10, at least 15, at least 20, at least 30, at least 40, at least 50, at least 60, at least 70, at least 80, at least 90, at least 100, at least 150, at least 200, at least 250, at least 300, at least 350, at least 380 wells, e.g., 384 or more.

According to some embodiments of the invention, drop 36 is from about 0.2 to about 5 microliters in volume.

According to some embodiments of the invention, drop 36 is from about 0.8 to about 1.4 microliters in volume.

According to some embodiments of the invention, drop 36 is about 0.8 microliters in volume, about 0.9, about 1.0, about 1.1, about 1.2, about 1.3, about 1.4 microliters in volume.

According to some embodiments of the invention, forming drop 36 is at a rate of from about 1 to about 100 microliters per second.

According to some embodiments of the invention, forming drop 36 is at a rate of from about 5 to about 95 microliters per second, from about 10 to about 90 microliters per second, from about 15 to about 85 microliters per second, from about 20 to about 80 microliters per second, from about 30 to about 70 microliters per second, e.g., at a rate of about 40 microliters per second, about 50 microliters per second or about 60 microliters per second.

As used herein the phrase "polymeric solution" refers to a soluble polymer, i.e., a liquid medium containing one or more polymers, co-polymers or blends of polymers dissolved in a solvent. The polymer according to some embodiments of the invention can be a natural, synthetic, biocompatible and/or biodegradable polymer.

According to some embodiments of the invention, the polymer of said polymeric solution is a natural polymer.

According to some embodiments of the invention, the polymer of said polymeric solution is a synthetic polymer.

The phrase "synthetic polymer" refers to polymers that are not found in nature, even if the polymers are made from naturally occurring biomaterials. Examples include, but are not limited to, aliphatic polyesters, poly(amino acids), copoly(ether-esters), polyalkylenes oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, and combinations thereof.

Suitable synthetic polymers for use by the invention can also include biosynthetic polymers based on sequences found in naturally occurring proteins such as those of collagen, elastin, thrombin, fibronectin, or derivatives thereof or, starches, poly(amino acids), poly(propylene fumarate), gelatin, alginate, pectin, fibrin, oxidized cellulose, chitin, chitosan, tropoelastin, hyaluronic acid, polyethylene, polyethylene terephthalate, poly(tetrafluoroethylene), polycarbonate, polypropylene and poly(vinyl alcohol), ribonucleic acids, deoxyribonucleic acids, polypeptides, proteins, polysaccharides, polynucleotides and combinations thereof.

The phrase "natural polymer" refers to polymers that are naturally occurring. Non-limiting examples of such polymers include, silk, collagen-based materials, chitosan, hyaluronic acid, albumin, fibrinogen, and alginate.

As used herein, the phrase "co-polymer" refers to a polymer of at least two chemically distinct monomers. Non-limiting examples of co-polymers include, polylactic acid (PLA)-polyethyleneglycol (PEG), polyethylene glycol terephthalate (PEGT)/polybutylene terephthalate (PBT), PLA-polyglycolic acid (PGA), PEG-polycaprolactone (PCL) and PCL-PLA.

As used herein, the phrase "blends of polymers" refers to the result of mixing two or more polymers together to create a new material with different physical properties.

The phrase "biocompatible polymer" refers to any polymer (synthetic or natural) which when in contact with cells, tissues or body fluid of an organism does not induce adverse effects such as immunological reactions and/or rejections, cellular death and the like. It will be appreciated that a biocompatible polymer can also be a biodegradable polymer.

Non-limiting examples of biocompatible polymers include polyesters (PE), PCL, Calcium sulfate, PLA, PGA, PEG, polyvinyl alcohol, polyvinyl pyrrolidone, Polytetrafluoroethylene (PTFE, teflon), polypropylene (PP), polyvinylchloride (PVC), Polymethylmethacrylate (PMMA), polyamides, segmented polyurethane, polycarbonate-urethane and thermoplastic polyether urethane, silicone-polyether-urethane, silicone-polycarbonate-urethane collagen, PEG-DMA, alginate, hydroxyapatite and chitosan, blends and copolymers thereof.

The phrase "biodegradable polymer" refers to a synthetic or natural polymer which can be degraded (i.e., broken down) in the physiological environment such as by proteases or other enzymes produced by living organisms such as bacteria, fungi, plants and animals. Biodegradability depends on the availability of degradation substrates (i.e., biological materials or portion thereof which are part of the polymer), the presence of biodegrading materials (e.g., microorganisms, enzymes, proteins) and the availability of oxygen (for aerobic organisms, microorganisms or portions thereof), lack of oxygen (for anaerobic organisms, microorganisms or portions thereof) and/or other nutrients. Examples of biodegradable polymers/materials include, but are not limited to, collagen (e.g., Collagen I or IV), fibrin, hyaluronic acid, polylactic acid (PLA), polyglycolic acid (PGA), polycaprolactone (PCL), polydioxanone (PDO), trimethylene carbonate (TMC), polyethyleneglycol (PEG), collagen, PEG-DMA, alginate, chitosan copolymers or mixtures thereof.

According to some embodiments of the invention, the cells contained in said polymeric solution are provided at a concentration of $1\times10^5$ to $1\times10^9$ cells/mL (milliliter).

According to some embodiments of the invention, the cells contained in said polymeric solution are provided at a concentration of $1\times10^6$ to $1\times10^8$ cells/mL.

According to some embodiments of the invention, the cells contained in said polymeric solution are provided at a concentration of $1\times10^7$ to $1\times10^8$ cells/mL.

According to some embodiments of the invention, the cells contained in said polymeric solution are provided at a concentration of about $1\times10^6$, about $3\times10^6$, about $5\times10^6$, about $7\times10^6$, about $1\times10^7$, about $3\times10^7$, about $5\times10^7$, about $7\times10^7$, about $1\times10^8$, about $3\times10^8$, about $5\times10^8$, about $7\times10^8$, or about $1\times10^9$ cells/mL.

According to some embodiments of the invention, the polymeric solution further comprises an oxygen sensor.

Oxygen Sensors

Real-time oxygen measurements can be performed optically using tissue embedded lifetime-based luminescence quenching (LBLQ) (oxygen sensor) (Schmalzlin E., et al., 2005. Biophysical journal, 89: 1339-1345; Papkovsky, D. B. et al., 2004. Methods in enzymology, 381, 715-735; Ast, C., et al., 2012, 12: 7015-7032).

For example, suitable oxygen sensors can be the CPOx-50-RuP oxygen-sensing beads (Colibri Photonics). RuP phosphorescence signal shows a characteristic delay given by the lifetime of its excited triplet state. Oxygen acts as a quencher, leading to a decrease in decay time and signal intensity with increasing concentration.

Following is a non-limiting example of using oxygen sensors. Twenty nanometer (20 nm) to 200 μm in diameter polymeric microbeads, such as polystyrene or PEG microbeads, can be loaded with ruthenium-phenanthroline-based phosphorescence dye such as CPOx-50-RuP (Colibri Photonics) or OXNANO (Pyro Science). These sensors range in mean diameter from 50 μm (CPOx-50-RuP) to 200 nm (OXNANO) but have a batch size-dependent diameter range of less than 4-folds, yielding similar excitation-signal behavior.

The oxygen sensors can be embedded micro- or nano-sized sensors which permit precise measurement of oxygen uptake rate in real-time.

According to some embodiments of the invention, the oxygen sensor comprises an optical sensor patch.

According to some embodiments of the invention, the oxygen sensor comprises an optical sensor probe.

According to some embodiments of the invention, the oxygen sensor is provided at a concentration of 0.1-10 mg (milligram) per milliliter of said polymeric solution. e.g., at a concentration of 0.2-9 mg/ml, 0.3-8 mg/ml, 0.4-7 mg/ml, 0.4-6 mg/ml, 0.5-5 mg/ml of the polymeric solution.

According to some embodiments of the invention, the oxygen sensor is provided at a concentration of 0.5-4 mg (milligram) per milliliter of said polymeric solution.

According to some embodiments of the invention, the oxygen sensor is provided at a concentration of 1-4 mg per ml of the polymeric solution, e.g., at a concentration of 2-4 mg per ml of the polymeric solution, e.g., at a concentration of 3-3.5 mg per ml of the polymeric solution, e.g., at a concentration of 3-5 mg per ml of the polymeric solution.

According to some embodiments of the invention, releasing said drop from said end is performed once per each well such that a single organoid is generated in each well.

According to some embodiments of the invention, the organoid is distinct.

As used herein the term "distinct" with respect to organoid refers to being separated from another organoid present in the same environment, e.g., in the same well.

According to some embodiments of the invention, the multi-well plate is a 384 well plate.

According to some embodiments of the invention, the controlling said robotic arm is by a computerized control system pre-programed to ensure that said contact is established.

According to some embodiments of the invention, the computerized control system is configured to receive position data pertaining to a height of said robotic arm above said surface, and to move said robotic arm responsively to said position data.

According to some embodiments of the invention, the method further comprising applying a culture medium to said organoid generated on said well.

As used herein the phrase "culture medium" refers to a solid or a liquid substance used to support the growth of cells (isolated cells or cells or within a tissue or an organoid). Preferably, the phrase "culture medium" as used herein refers to a liquid substance capable of maintaining the cells in a metabolically active state. The culture medium used by the present invention can be a water-based medium which includes a combination of substances such as salts, nutrients, minerals, vitamins, amino acids, nucleic acids, proteins such as cytokines, growth factors and hormones, all of which are needed for cell growth and maintenance of cells metabolically active. For example, a culture medium can be a synthetic tissue culture medium such as mTESR, E8, NutriStem, PluriSTEM, William's E, RPMI 1640, DMEM (Dulbecco's Modified Eagle Medium), MEM (Minimum Essential Medium Eagle), KO-DMEM (Knockout Dulbecco's Modified Eagle Medium), IMDM (Iscove's Modified Dulbecco's Medium), Neurobasal medium, EGM-2 (Endothelial growth medium), EMV-2 (Endothelial microvascular medium), HMM (Hepatocytes Maintenance Medium), Medium 199 or MCDB105/153/131/170 supplemented with the necessary additives as is further described hereinunder.

As used herein the term "defined culture medium" refers to a culture medium which is man-made and all its components are known.

According to some embodiments of the invention, applying said culture medium is performed following gelation of a polymer matrix from the polymeric solution within the drop.

According to some embodiments of the invention, the culture medium is applied within 5 minutes after the completion of the gelation of the polymer matrix from the polymeric solution within the drop.

The time required for gelation of the polymer matrix may vary depending on the polymeric solution. For example, when using 50% Matrigel polymeric solution the average gelation time of the polymeric matrix is between 25-35 minutes; when using 90% Matrigel polymeric solution the average gelation time of the polymeric matrix is between 15-25 minutes; when using 50% Collagen-Type 1 polymeric solution the average gelation time of the polymeric matrix is between 40-50 minutes; when using Alginate polymeric solution the average gelation time of the polymeric matrix is between 50-110 minutes; when using 50% Gelatin polymeric solution the average gelation time of the polymeric matrix is between 40-50 minutes; when using a Laminin/ Fibronectin polymeric solution the average gelation time of the polymeric matrix is between 15-25 minutes.

According to some embodiments of the invention, the gelation occurs within about 30 minutes of releasing said drop on the surface.

Once the organoid is completely formed and stabilized the method further comprises adding a drug to the culture medium.

It should be noted that an organoid is completely formed when the 3D structure is visible, and the organoid is considered stabilized when the oxygen consumption is stable over a period of about one hour. For determining the stability of the organoid, the oxygen levels are measured continuously for about one hour.

According to some embodiments of the invention, when the organoid is a tumor organoid, the organoid is completely formed and stabilized within about 24 hours.

According to some embodiments of the invention, when the organoid is a liver organoid, the organoid is completely formed and stabilized within about 4 days.

According to some embodiments of the invention, when the organoid is a heart organoid, the organoid is completely formed, beating and stabilized within about 8 hours.

According to some embodiments of the invention, the medium comprises a drug.

According to an aspect of some embodiments of the invention there is provided a system for generating an organoid, the system comprising:

a surface which is characterized by a water contact angle of at least 70 degrees;

a controllable liquid channel mounted on a robotic arm, and being configured for forming a drop of a polymeric solution comprising cells;

a computerized control system programed to move said robotic arm toward said surface such as to establish a contact between a surface of said drop and said surface, and to control said controllable liquid channel to release said drop once said contact is established.

According to an aspect of some embodiments of the invention there is provided a multi-well plate comprising an array of wells each containing a distinct organoid therein, wherein a size of each organoid is within less than 20% or less than 15% or less than 10% from an average size of all organoids occupying said multi-well plate.

According to some embodiments of the invention, the organoids present in the wells of the multi-well plate are homogenous in terms of size and/or cell number.

According to some embodiments of the invention, each well has a single (distinct organoid), wherein all organoids are homogenous.

According to some embodiments of the invention, the homogenous population of organoids have less than 20% variability, less than 19%, less than 18%, less than 17%, less than 16%, less than 15%, less than 14%, less than 13%, less than 12%, less than 11%, less than 10% variability in size and/or in the number of cells contained in each organoid, and/or type of cells contained in each organoid and/or in shape of each organoid.

According to some embodiments of the invention, the homogenous population of organoids is characterized by at least 50%, at least 55%, at least 60%, at least 65%, at least 70%, at least 75%, at least 80%, at least 85%, at least 90%, at least 95% of the organoids are 0.5% standard deviation from the average size of the organoids.

According to some embodiments of the invention, the organoid comprises at least one oxygen sensor.

According to some embodiments of the invention, each oxygen sensor is a particle.

According to some embodiments of the invention, the oxygen sensor comprises an optical sensor patch.

According to some embodiments of the invention, the oxygen sensor comprises an optical sensor probe.

According to some embodiments of the invention, the at least one oxygen sensor is embedded within each of said organoids.

In spite of significant advances in understanding, diagnosis, and treatment over the last decade, cancer is still one of the leading causes of death with global medical costs totaling over $1.2 trillion/year.

All cancer types are caused by gene mutations. Thus, recent technological advancements in next-generation sequencing (NGS), together with the steep decrease in their costs lead to widespread use of these methods to create molecularly targeted therapies based on tumor molecular profiling.

However, in numerous cancer patients the interpretation of test results is challenging due to multiple gene mutations in various pathways, previously undescribed alterations (with unknown effect on protein function) and non-targetable alterations (without a potent inhibitor in the market). As a result, for various reasons, most clinical trials molecularly targeted therapy based on tumor molecular profiling failed to improve progression-free-survival.

Recently, it was shown some of the resistance to treatment and the inability to reach complete tumor eradication is due to tumor heterogeneity, the persistence of cancer stem cells (CSCs), senescent- or hypoxic-tumor cores and complex interactions between different tumor components (Hubert et al. 2016, Wang et al. 2018). Thus, severely limiting the potency and effectivity of targeted therapies and bulk molecular profiling. Single cell analysis, on the other hand, fail to show clinically relevant solutions to provide actionable information to improve the targeted approach.

To tackle these complexities, the present inventors developed a proprietary screening platform that allows to maintain tissues for several days under physiological conditions, tracking its metabolic function and viability in real-time using the tissue-embedded microsensors. Thus, this platform is uniquely capable of distinguishing between drugs that only damage part of the tumor or has a transient effect (False Positive) or to slow working drugs that are missed in most screens (False Negative) but that specifically damage the root cause of the cancer, its cancer stem cells (CSCs).

The present inventors have further applied this platform on patient derived glioblastoma cells and found novel FDA approved chemotherapeutic drugs that specifically targeted the CSC population.

The present inventors have uncovered a novel way to monitor and measure in a real-time resolution the anti-proliferative effect of drugs and anti-cancer agents on patient-derived tumor cells and tumor models cultured in physiological environment using automated multi-well plates (e.g., 384-well plate) assays.

The method according to some embodiments of this aspect of the invention involves a continuous monitoring of the metabolic phenotype of cancer stem cells (CSC) in their native microenvironment, elucidating strategies to eradicate the disease at its root.

The present inventors have developed a method in which oxygen microsensors are embedded in patient-derived three-dimensional micro-tumor organoids. According to some embodiments of the invention tumors are formed in 384 well plate format and screened against FDA-approved chemotherapy drugs for 60 to 72 hours. This high throughput kinetic screen can separate between true positive, when respiration stops, false positive, where the drug appears to work but the tumor recovers over time, and false negative, where the tumor simply takes longer to die. The chemotherapeutic drug candidates include, without limitation, NIH plate assays of FDA-approved anti-cancer drugs, kinase inhibitors, and other small molecule or biological drugs. While the Examples section which follows shows the effect of several chemotherapy on glioblastoma cancer cells, the screening platform is readily extendible to other types of cancer that can be similarly modeled (e.g., liver, pancreas, lung). In addition, the platform can include immune cells, allowing to exclusively screen immunotherapy therapeutics, one of the fastest growing sectors in oncology.

There are multiple unique advantages of the tumor profiling method of some embodiments of the invention as compared to available services. First, molecular profiling approaches require a priori knowledge of biomarkers that are associated with beneficial therapeutic outcome. While such biomarkers are known for breast cancer, lung cancer, and several type of gastrointestinal cancers, this isn't the case for glioblastoma. Unbiased clustering approaches, attempting to associate patients with those that responded to a specific therapy have had limited prognostic value. The method of some embodiments of the invention does not require a priori knowledge as carries out an unbiased screen of the patient-own cells against all available therapeutic options. While this technique could be compared to CTC (circulating tumor cell) profiling, those need to be measured at multiple time points during treatment to evaluate whether the therapy is effective. The method of some embodiments of the invention provides this type of information without exposing the patient to cytotoxic agents, more accurately choosing the correct therapeutic against for each patient.

In addition, while emerging technology could offer to screen FDA-approved drug against living cells, these isolated cells do not constitute the unique tumor environment and persistent cancer stem cells (CSCs) that are the root of the disease. The method of some embodiments of the invention mimics the tumor environment and can directly reconstitute the tumor persistent cell population allowing to directly monitor and target these cells for treatment (Hubert et al. 2016).

Furthermore, while current cell viability is monitored using end-point assays, the method of some embodiments of the invention uses oxygen sensors (e.g., about 50 micrometer in size), which offer a non-destructive continuous measurement of cell function, allowing to detect both response, persistent and recovery during a wash out step using a single living sample.

According to some embodiments of an aspect of the invention, micro-tissues are embedded with oxygen sensors permitting non-invasive monitoring of metabolic activity.

According to some embodiments of an aspect of the invention, micro-tissues embedded with oxygen micro-sensors are used for tracking the dynamics of micro-tissue viability and damage in response to various drugs, such as those listed in Tables 1 and 2 below, and those exemplified in some drawings of the invention, like acetaminophen, rotenone, amiodarone and troglitazone exposure. This strategy both reduces the cost and labor required to assess the toxicity of these agents.

TABLE 1

FDA-approved anticancer drugs that were tested in high content screening in the method of some embodiments of the invention both in micro-tumors and patient-derived micro-tumors

| | |
|---|---|
| Dasatinib | Alectinib |
| Everolimus | Binimetinib |
| Pazopanib hydrochloride | Dabrafenib mesylate |
| Imatinib | Bosutinib |
| Lapatinib | Dacomitinib |
| Nilotinib | Venetoclax |
| Sorafenib | Talazoparib |
| Lenalidomide | Cobimetinib |
| Ixabepilone | Abemaciclib |
| Raloxifene | Apalutamide |
| Abiraterone | Duvelisib |
| Sunitinib | Pomalidomide |
| Afatinib | Ceritinib |
| Olaparib | Encorafenib |
| Romidepsin | Ribociclib |
| Pralatrexate | Osimertinib |
| Niraparib hydrochloride | Larotrectinib |
| Pemetrexed, Disodium salt, Heptahydrate | Brigatinib |
| Enzalutamide | Enasidenib |
| Lenvatinib | Uridine triacetate |
| Nelarabine | Ivosidenib |
| Vismodegib | Acalabrutinib |
| Rucaparib phosphate | Copanlisib |
| Crizotinib | Methotrexate |
| Bortezomib | Busulfan |
| Neratinib | Thioguanine |
| Axitinib | Mercaptopurine |
| Trametinib | Mechlorethamine hydrochloride |
| Palbociclib | Allopurinol |
| Carfilzomib | Dactinomycin |
| Omacetaxine mepesuccinate | Chlorambucil |
| Ixazomib citrate | Thiotepa |
| Ponatinib | Melphalan hydrochloride |
| Belinostat | Triethylenemelamine |
| Idelalisib | Altretamine |
| Vandetanib | Aminolevulinic acid hydrochloride |
| Cabozantinib | Fluorouracil |
| Panobinostat | Plicamycin |
| Erismodegib | Pipobroman |
| Plerixafor | Cyclophosphamide |
| Vemurafenib | Mitomycin |
| Cabazitaxel | Floxuridine |
| Ibrutinib | Hydroxyurea |
| Regorafenib | Uracil mustard |
| Mitotane | Gemcitabine hydrochloride |
| Dacarbazine | Irinotecan hydrochloride |
| Methoxsalen | Docetaxel |
| Vinblastine sulfate | Temsirolimus |
| Cytarabine hydrochloride | Vorinostat |
| Thalidomide | Estramustine phosphate sodium |
| Vincristine sulfate | Capecitabine |
| Megestrol acetate | Exemestane |
| Trifluridine | Gefitinib |
| Procarbazine hydrochloride | Erlotinib hydrochloride |
| Lomustine | Fulvestrant |
| Daunorubicin hydrochloride | Anastrozole |
| Streptozocin | Letrozole |
| Arsenic trioxide | Celecoxib |
| Azacitidine | Zoledronic acid |
| Cladribine | Epirubicin hydrochloride |
| Ifosfamide | Oxaliplatin |
| Cisplatin | Mitoxantrone |
| Tretinoin | Amifostine |
| Teniposide | Fludarabine phosphate |
| Doxorubicin hydrochloride | Temozolomide |
| Bleomycin sulfate | Imiquimod |
| Paclitaxel | Carmustine |
| Decitabine | Clofarabine |
| Bendamustine hydrochloride | Vinorelbine tartrate |
| Etoposide | Topotecan hydrochloride |

TABLE 1-continued

FDA-approved anticancer drugs that were tested in high content screening in the method of some embodiments of the invention both in micro-tumors and patient-derived micro-tumors

| | |
|---|---|
| Dexrazoxane | Carboplatin |
| Tamoxifen citrate | Valrubicin |
| Pentostatin | Idarubicin hydrochloride |
| Sirolimus | |

Table 1. Set containing 147 current FDA-approved anticancer drugs tested in high content screening in the methods of some embodiments of the invention, both in micro-tumors and patient-derived micro-tumors.

TABLE 2

Drugs that have been shown acute or chronic toxicity tested in high content screening in the method of some embodiments of the invention in micro-tissues

| | |
|---|---|
| Acetaminophen | Stavudine |
| Thapsigargin | Troglitazone |
| Valproic Acid | Rosiglitazone |
| Tunicamycin | Amiodarone |
| Rotenone | Gentamycin |
| DDT | Melatonin |
| Cyclosporin A | Cisplatin |

Table 2. Set containing drugs that has shown acute or chronic toxicity tested in high content screening in the method of some embodiments of the invention, in micro-tissues.

According to some embodiments of an aspect of the invention, tracking the dynamics of micro-tissue and damage in response to drug exposure viability in many concentrations simultaneously within a single experiment allows to calculate toxicity levels in different exposure durations (TC over time) and the safety margins for the use of the drug by linking time to onset (TTO) and drug concentration mathematically and calculating the lower drug exposure (LEL).

According to some embodiments of an aspect of the invention, micro-tumors and patient derived micro-tumors embedded with oxygen micro-sensors are used for tracking the dynamics of treatment effectivity, pharmacokinetic analysis and tracking the effects of drug removal (i.e. wash out) on the CSC component itself.

The phrase "micro-tumor" refers to a vascularized heterogeneous cancer organoid recapitulating tumor characteristics. The heterogeneous cancer organoid comprises a mixed population of cancer cells and different tumor zones. Non-limiting examples of populations of cancer cells include, but are not limited to cancer stem cells, hypoxic core cells, partly differentiated peripheral cells and tumor-mass differentiated cells.

The phrase "Patient-derived micro-tumor" refers to a micro-tumor derived from a tumor directly isolated from a patient or from cells of the tumor isolated from the patient and expanded under conditions which preserve the characteristics and genetic identity. For example, patient's derived cancer stem cells are treated with EGF and FGF2 to maintain SOX2 and OLIG1 expression that resemble the patient's tumor cancer stem cells.

Patient's tumor is the original tumor in the patient or a biopsy of thereof.

Uniquely, this model mimics the complex microenvironment and vascular niche developing in tissue niches or tumors, permitting the screening of not only small molecular therapeutics, but also nanoparticles and their ability to target specific components such as CSCs in the tumor itself or sub populations within the tissue.

According to some embodiments of an aspect of the invention, the platform also includes adverse outcome controls such as normal human brain (mini-brains) and liver tissue (mini-livers) to evaluate the safety-effectivity range.

According to some embodiments of an aspect of the invention, this method is used for the rapid commercialization of a diagnostics service for cancer patients that will offer the ability to precisely predict which therapeutic formation would be most beneficial in eradicating the tumor, extending lives and lowering the medical costs associated with repeated treatments.

According to some embodiments of an aspect of the invention, the cell preparation step includes isolating living cells from patient biopsies and mimicking the in vivo microenvironment in a cost-efficient manner that permits high-throughput screening of precision-therapeutics.

According to an aspect of some embodiments of the invention, there is provided an in vitro method of screening an agent for treating cancer, comprising:

generating multiple tumor organoids from a tumor biopsy of a subject on at least a few wells of a multi-well plate, wherein each well of said at least a few wells comprises at least one tumor organoid, and wherein each of said tumor organoids comprises at least one oxygen sensor, contacting at least one of said tumor organoids with said agent, and measuring percentage of oxygen in each of said tumor organoids following said contacting, wherein an increase in said percentage of oxygen following said contacting as compared to prior to said contacting is indicative that the agent is suitable for treating the cancer, thereby screening the agent suitable for treating the cancer of the subject.

According to some embodiments of the invention, each well of said at least a few wells comprises a single organoid.

According to some embodiments of the invention, wherein presence of an oxygen plateau of about 21% oxygen over a predetermined time period in said tumor organoids is indicative that the agent is a suitable drug for killing of proliferating cancer cells and cancer stem cells comprised in said tumor organoid.

As used herein, the term "cancer stem cell", (also referred to as "CSC"), refers to a cell which has the capacity to regenerate cancers using xenograft (Xn) mouse models. CSCs can reproduce themselves through the process of self-renewal, which can be studied in serial transplantation assays. Additionally, cancers derived from purified CSCs recapitulate the heterogeneous phenotypes of the parental cancer from which they were derived, reflecting the differentiation capacity of CSCs.

According to some embodiments of the invention, the cancer stem cells are multipotent, resistant cancer cells capable of adapting and differentiating into the high-proliferating cancer cells forming the tumor.

It is noted that the cancer stem cells have a slower proliferation rate as compared to the proliferating cancer cells comprised in the cancerous tumor.

According to some embodiments of the invention, the predetermined time period is at least 48 hours.

According to some embodiments of the invention, the predetermined time period is at least 72 hours.

According to some embodiments of the invention, the predetermined time period is at least 96 hours.

According to some embodiments of the invention, the measuring is continuous.

According to some embodiments of the invention, the drug is a chemotherapeutic drug.

According to some embodiments of the invention, the drug is an immunotherapy drug.

According to some embodiments of the invention, the drug is a small molecule.

According to some embodiments of the invention, the cancer is selected from the group consisting of: glioblastoma, liver cancer, lung cancer, breast cancer, brain cancer, colorectal cancer, and prostate cancer.

According to some embodiments of the invention, the cancer is glioblastoma.

According to some embodiments of the invention, the drug is selected from the group consisting of acetaminophen, omacetaxine mepesuccinate, bortezomib, Valproate, Daunorubicin hydrochloride, Romidepsin, Thapsigargin, Stavudine and Melatonin.

Omacetaxine mepesuccinate (INN), also known as homoharringtonine or HHT, is a pharmaceutical drug substance that is indicated for treatment of chronic myeloid leukemia (CML).

Bortezomib (also known as Velcade) is an anti-cancer medication used to treat multiple myeloma and mantle cell lymphoma.

Valproate (VPA), and its valproic acid, sodium valproate, and valproate semisodium forms, are medications primarily used to treat epilepsy and bipolar disorder and to prevent migraine headaches. They are useful for the prevention of seizures in those with absence seizures, partial seizures, and generalized seizures. They can be given intravenously or by mouth. Long and short acting formulations of tablets exist.

Daunorubicin hydrochloride (also known as daunorubicin hydrochloride; daunomycin; rubidomycin hydrochloride) is a drug for the treatment of Treatment of acute myelogenous leukemia (AML), acute lymphoblastic leukemia (ALL) and acute promyelocytic leukemia (APL).

Romidepsin is an anti-cancer ("antineoplastic" or "cytotoxic") chemotherapy drug classified as a "Histone Deacetylase Inhibitor", used to treat cutaneous T-cell lymphoma (CTCL) and peripheral T-cell lymphoma (PTCL).

Thapsigargin is non-competitive inhibitor of the sarco/endoplasmic reticulum Ca2+ ATPase (SERCA), and is classified as a sesquiterpene lactone. Thapsigargin dose-dependently reduced the brain infarct.

Stavudine (also known as d4T) is classified as a Nucleoside Reverse Transcriptase Inhibitor, used for the treatment of HIV infection in adults, children, and infants. Stavudine is always used in combination with other HIV medicines.

Melatonin (also known as 5-Methoxy-N-Acetyltryptamine, MEL, Melatonina, Melatonine, MLT, N-acetyl-5-methoxytryptamine) is used to treat a delayed sleep phase syndrome, and to improve sleep in blind subjects.

According to some embodiments of the invention, the generating multiple tumor organoids is performed by a method comprising:

forming at an end of a liquid channel a drop of a polymeric solution comprising tumor cells and oxygen sensors;

while said drop is connected to said end, establishing a contact between a surface of said drop and a surface which is characterized by a water contact angle of at least 70 degrees, wherein said surface is a base of said multi-well plate or a hydrogel coating a base of said multi-well plate, preferably a hydrophobic hydrogel;

releasing said drop from said end; and incubating said drop conditions that promote formation of the tumor organoid.

According to some embodiments of the invention, the establishing is operated by a robotic arm.

According to some embodiments of the invention, the surface is a hydrophobic surface.

According to some embodiments of the invention, repeating said method for each of at least a few wells of said multi-well plate.

According to some embodiments of the invention, the drop is from about 0.2 to about 5 microliters in volume.

According to some embodiments of the invention, the drop is from about 0.8 to about 1.4 microliters in volume.

According to some embodiments of the invention, forming said drop is at a rate of from about 1 to about 100 microliters per second.

According to some embodiments of the invention, releasing said drop is executed when a distance between said end and said surface is less than a diameter of said drop.

According to some embodiments of the invention, releasing said drop is executed when a distance between said end and said surface is from about 0.16 to about 0.2 mm less than a diameter of said drop.

According to some embodiments of the invention, releasing said drop is executed when a distance between said end and said surface is about 0.18 mm less than a diameter of said drop.

According to some embodiments of the invention, the polymer of said polymeric solution is a natural polymer.

According to some embodiments of the invention, the polymer of said polymeric solution is a synthetic polymer.

According to some embodiments of the invention, the cells contained in said polymeric solution are provided at a concentration of $1 \times 10^5$ to $1 \times 10^9$ cells/mL (milliliter).

According to some embodiments of the invention, the oxygen sensor is provided at a concentration of 0.5-4 mg (milligram) per each milliliter of polymeric solution which comprises said tumor cells.

According to some embodiments of the invention, controlling said robotic arm is by a computerized control system pre-programed to ensure that said contact is established.

According to some embodiments of the invention, the computerized control system is configured to receive position data pertaining to a height of said robotic arm above said surface, and to move said robotic arm responsively to said position data.

Non-limiting examples of cancers for treatment of which the agents (drugs) are screened by the method of some embodiments of the invention include any solid or non-solid cancer and/or cancer metastasis, including, but is not limiting to, tumors of the gastrointestinal tract (colon carcinoma, rectal carcinoma, colorectal carcinoma, colorectal cancer, colorectal adenoma, hereditary nonpolyposis type 1, hereditary nonpolyposis type 2, hereditary nonpolyposis type 3, hereditary nonpolyposis type 6; colorectal cancer, hereditary nonpolyposis type 7, small and/or large bowel carcinoma, esophageal carcinoma, tylosis with esophageal cancer, stomach carcinoma, pancreatic carcinoma, pancreatic endocrine tumors), endometrial carcinoma, dermatofibrosarcoma protuberans, gallbladder carcinoma, Biliary tract tumors, prostate cancer, prostate adenocarcinoma, renal cancer (e.g., Wilms' tumor type 2 or type 1), liver cancer (e.g., hepatoblastoma, hepatocellular carcinoma, hepatocellular cancer), bladder cancer, embryonal rhabdomyosarcoma, germ cell tumor, trophoblastic tumor, testicular germ cells tumor, immature teratoma of ovary, uterine, epithelial ovarian, sacrococcygeal tumor, choriocarcinoma, placental site trophoblastic tumor, epithelial adult tumor, ovarian carcinoma, serous ovarian cancer, ovarian sex cord tumors, cervical carcinoma, uterine cervix carcinoma, small-cell and non-small cell lung carcinoma, nasopharyngeal, breast carcinoma (e.g., ductal breast cancer, invasive intraductal breast cancer, sporadic; breast cancer, susceptibility to breast cancer, type 4 breast cancer, breast cancer-1, breast cancer-3; breast-ovarian cancer), squamous cell carcinoma (e.g., in head and neck), neurogenic tumor, astrocytoma, ganglioblastoma, neuroblastoma, lymphomas (e.g., Hodgkin's disease, non-Hodgkin's lymphoma, B cell, Burkitt, cutaneous T cell, histiocytic, lymphoblastic, T cell, thymic), gliomas, adenocarcinoma, adrenal tumor, hereditary adrenocortical carcinoma, brain malignancy (tumor), various other carcinomas (e.g., bronchogenic large cell, ductal, Ehrlich-Lettre ascites, epidermoid, large cell, Lewis lung, medullary, mucoepidermoid, oat cell, small cell, spindle cell, spinocellular, transitional cell, undifferentiated, carcinosarcoma, choriocarcinoma, cystadenocarcinoma), ependymoblastoma, epithelioma, erythroleukemia (e.g., Friend, lymphoblast), fibrosarcoma, giant cell tumor, glial tumor, glioblastoma (e.g., multiforme, astrocytoma), glioma hepatoma, heterohybridoma, heteromyeloma, histiocytoma, hybridoma (e.g., B cell), hypernephroma, insulinoma, islet tumor, keratoma, leiomyoblastoma, leiomyosarcoma, leukemia (e.g., acute lymphatic, acute lymphoblastic, acute lymphoblastic pre-B cell, acute lymphoblastic T cell leukemia, acute-megakaryoblastic, monocytic, acute myelogenous, acute myeloid, acute myeloid with eosinophilia, B cell, basophilic, chronic myeloid, chronic, B cell, eosinophilic, Friend, granulocytic or myelocytic, hairy cell, lymphocytic, megakaryoblastic, monocytic, monocytic-macrophage, myeloblastic, myeloid, myelomonocytic, plasma cell, pre-B cell, promyelocytic, subacute, T cell, lymphoid neoplasm, predisposition to myeloid malignancy, acute nonlymphocytic leukemia), lymphosarcoma, melanoma, mammary tumor, mastocytoma, medulloblastoma, mesothelioma, metastatic tumor, monocyte tumor, multiple myeloma, myelodysplastic syndrome, myeloma, nephroblastoma, nervous tissue glial tumor, nervous tissue neuronal tumor, neurinoma, neuroblastoma, oligodendroglioma, osteochondroma, osteomyeloma, osteosarcoma (e.g., Ewing's), papilloma, transitional cell, pheochromocytoma, pituitary tumor (invasive), plasmacytoma, retinoblastoma, rhabdomyosarcoma, sarcoma (e.g., Ewing's, histiocytic cell, Jensen, osteogenic, reticulum cell), schwannoma, subcutaneous tumor, teratocarcinoma (e.g., pluripotent), teratoma, testicular tumor, thymoma and trichoepithelioma, gastric cancer, fibrosarcoma, glioblastoma multiforme; multiple glomus tumors, Li-Fraumeni syndrome, liposarcoma, lynch cancer family syndrome II, male germ cell tumor, mast cell leukemia, medullary thyroid, multiple meningioma, endocrine neoplasia myxosarcoma, paraganglioma, familial nonchromaffin, pilomatricoma, papillary, familial and sporadic, rhabdoid predisposition syndrome, familial, rhabdoid tumors, soft tissue sarcoma, and Turcot syndrome with glioblastoma.

Pre-Cancers

Precancers are well characterized and known in the art (refer, for example, to Berman J J. and Henson D E., 2003. Classifying the precancers: a metadata approach. BMC Med Inform Decis Mak. 3:8). Classes of precancers amenable to treatment via the method of the invention include acquired small or microscopic precancers, acquired large lesions with nuclear atypia, precursor lesions occurring with inherited hyperplastic syndromes that progress to cancer, and acquired diffuse hyperplasias and diffuse metaplasias. Examples of small or microscopic precancers include HGSIL (High grade squamous intraepithelial lesion of uterine cervix), AIN (anal intraepithelial neoplasia), dysplasia of vocal cord, aberrant crypts (of colon), PIN (prostatic intraepithelial neoplasia). Examples of acquired large lesions with nuclear atypia include tubular adenoma, AILD (angioimmunoblastic lymphadenopathy with dysproteinemia), atypical meningioma, gastric polyp, large plaque parapsoriasis, myelodysplasia, papillary transitional cell carcinoma in-situ, refractory anemia with excess blasts, and Schneiderian papilloma. Examples of precursor lesions occurring with inherited hyperplastic syndromes that progress to cancer include atypical mole syndrome, C cell adenomatosis and MEA. Examples of acquired diffuse hyperplasias and diffuse metaplasias include AIDS, atypical lymphoid hyperplasia, Paget's disease of bone, post-transplant lymphoproliferative disease and ulcerative colitis.

TABLE 3

| Approved Oncology Drugs with Approved Indications | | | | |
|---|---|---|---|---|
| Aldesleukin | Proleukin | | Chiron Corp | May 5, 1992 |
| Alemtuzumab | Campath | Accel. Approv. (clinical benefit not established) Campath is indicated for the treatment of B-cell chronic lymphocytic leukemia (B-CLL) in patients who have been treated with alkylating agents and who have failed fludarabine therapy. | Millennium and ILEX Partners, LP | May 7, 2001 |
| alitretinoin | Panretin | Topical treatment of cutaneous lesions in patients with AIDS-related Kaposi's sarcoma. | Ligand Pharmaceuticals | Feb. 2, 1999 |
| allopurinol | Zyloprim | Patients with leukemia, lymphoma and solid tumor malignancies who are receiving cancer therapy which causes elevations of serum and urinary uric acid levels and who cannot tolerate oral therapy. | GlaxoSmith Kline | May 17, 1996 |
| altretamine | Hexalen | Single agent palliative treatment of patients with persistent or recurrent ovarian cancer following first-line therapy with a cisplatin and/or alkylating agent based combination. | US Bioscience | Dec. 26, 1990 |

TABLE 3-continued

| Approved Oncology Drugs with Approved Indications | | | | |
|---|---|---|---|---|
| amifostine | Ethyol | To reduce the cumulative renal toxicity associated with repeated administration of cisplatin in patients with advanced ovarian cancer | US Bioscience | Dec. 8, 1995 |
| amifostine | Ethyol | Accel. Approv. (clinical benefit not established) Reduction of platinum toxicity in non-small cell lung cancer | US Bioscience | Mar. 15, 1996 |
| amifostine | Ethyol | To reduce post-radiation xerostomia for head and neck cancer where the radiation port includes a substantial portion of the parotid glands. | US Bioscience | Jun. 24, 1999 |
| anastrozole | Arimidex | Accel. Approv. (clinical benefit not established) for the adjuvant treatment of postmenopausal women with hormone receptor positive early breast cancer | AstraZeneca | Sep. 5, 2002 |
| anastrozole | Arimidex | Treatment of advanced breast cancer in postmenopausal women with disease progression following tamoxifen therapy. | Astrazeneca Pharmaceuticals | Dec. 27, 1995 |
| anastrozole | Arimidex | For first-line treatment of postmenopausal women with hormone receptor positive or hormone receptor unknown locally advanced or metastatic breast cancer. | Astrazeneca Pharmaceuticals | Sep. 1, 2000 |
| arsenic trioxide | Trisenox | Second line treatment of relapsed or refractory APL following ATRA plus an anthracycline. | Cell Therapeutic | Sep. 25, 2000 |
| Asparaginase | Elspar | ELSPAR is indicated in the therapy of patients with acute lymphocytic leukemia. This agent is useful primarily in combination with other chemotherapeutic agents in the induction of remissions of the disease in pediatric patients. | Merck & Co, Inc | Aug. 1, 2002 |
| BCG Live | TICE BCG | | Organon Teknika Corp | Aug. 21, 1998 |
| bexarotene | Targretin | For the treatment by oral capsule of capsules cutaneous manifestations of cutaneous T-cell lymphoma in patients who are refractory to at least one prior systemic therapy. | Ligand Pharmaceuticals | Dec. 29, 1999 |
| bexarotene gel | Targretin | For the topical treatment of cutaneous manifestations of cutaneous T-cell lymphoma in patients who are refractory to at least one prior systemic therapy. | Ligand Pharmaceuticals | Jun. 28, 2000 |
| bleomycin | Blenoxane | | Bristol-Myers Squibb | Jul. 31, 1973 |
| bleomycin | Blenoxane | Sclerosing agent for the treatment of malignant pleural effusion (MPE) and prevention of recurrent pleural effusions. | Bristol-Myers Squibb | Feb. 20, 1996 |
| busulfan intravenous | Busulfex | Use in combination with cyclophoshamide asconditioning regimen prior to allogeneic hematopoietic progenitor cell transplantation for chronic myelogenous leukemia. | Orphan Medical, Inc | Feb. 4, 1999 |
| busulfan oral | Myleran | Chronic Myelogenous Leukemia-palliative therapy | GlaxoSmith Kline | Jun. 26, 1954 |
| calusterone | Methosarb | | Pharmacia & Upjohn Company | Feb. 20, 1973 |
| capecitabine | Xeloda | Accel. Approv. (clinical benefit subsequently established) Treatment of metastatic breast cancer resistant to both paclitaxel and an anthracycline containing chemotherapy regimen or resistant to paclitaxel and for whom further anthracycline therapy may be contraindicated, e.g., patients who | Roche | Apr. 30, 1998 |

TABLE 3-continued

| | | Approved Oncology Drugs with Approved Indications | | |
|---|---|---|---|---|
| | | have received cumulative doses of 400 mg/m2 of doxorubicin or doxorubicin equivalents | | |
| capecitabine | Xeloda | Initial therapy of patients with metastatic colorectal carcinoma when treatment with fluoropyrimidine therapy alone is preferred. Combination chemotherapy has shown a survival benefit compared to 5-FU/LV alone. A survival benefit over 5_FU/LV has not been demonstrated with Xeloda monotherapy. | Roche | Apr. 30, 2001 |
| capecitabine | Xeloda | Treatment in combination with docetaxel of patients with metastatic breast cancer after failure of prior anthracycline containing chemotherapy | Roche | Sep. 7, 2001 |
| carboplatin | Paraplatin | Palliative treatment of patients with ovarian carcinoma recurrent after prior chemotherapy, including patients who have been previously treated with cisplatin. | Bristol-Myers Squibb | Mar. 3, 1989 |
| carboplatin | Paraplatin | Initial chemotherapy of advanced ovarian carcinoma in combination with other approved chemotherapeutic agents. | Bristol-Myers Squibb | Jul. 5, 1991 |
| carmustine | BCNU, BiCNU | | Bristol-Myers Squibb | Mar. 7, 1977 |
| carmustine with Polifeprosan 20 Implant | Gliadel Wafer | For use in addition to surgery to prolong survival in patients with recurrent glioblastoma multiforme who qualify for surgery. | Guilford Pharmaceuticals Inc. | Sep. 23, 1996 |
| celecoxib | Celebrex | Accel. Approv. (clinical benefit not established) Reduction of polyp number in patients with the rare genetic disorder of familial adenomatous polyposis. | Searle | Dec. 23, 1999 |
| chlorambucil | Leukeran | Chronic Lymphocytic Leukemia-palliative therapy | GlaxoSmith Kline | |
| chlorambucil | Leukeran | | GlaxoSmith Kline | Mar. 18, 1957 |
| cisplatin | Platinol | Metastatic testicular-in established combination therapy with other approved chemotherapeutic agents in patients with metastatic testicular tumors which have already received appropriate surgical and/or radiotherapeutic procedures. An established combination therapy consists of Platinol, Blenoxane and Velbam. | Bristol-Myers Squibb | Dec. 19, 1978 |
| cisplatin | Platinol | Metastatic ovarian tumors-in established combination therapy with other approved chemotherapeutic agents: Ovarian-in established combination therapy with other approved chemotherapeutic agents in patients with metastatic ovarian tumors who have already received appropriate surgical and/or radiotherapeutic procedures. An established combination consists of Platinol and Adriamycin. Platinol, as a single agent, is indicated as secondary therapy in patients with metastatic ovarian tumors refractory to standard chemotherapy who have not previously received Platinol therapy. | Bristol-Myers Squibb | Dec. 19, 1978 |
| cisplatin | Platinol | as a single agent for patients with transitional cell bladder cancer which is no longer amenable to local treatments such as surgery and/or radiotherapy. | Bristol-Myers Squibb | Apr. 22, 1993 |
| cladribine | Leustatin, 2-CdA | Treatment of active hairy cell leukemia. | R.W. Johnson | Feb. 26, 1993 |

TABLE 3-continued

| Approved Oncology Drugs with Approved Indications | | | | |
|---|---|---|---|---|
| | | | Pharmaceutical Research Institute | |
| cyclophosphamide | Cytoxan, Neosar | | Bristol-Myers Squibb | Nov. 16, 1959 |
| cyclophosphamide | Cytoxan Injection | | Bristol-Myers Squibb | Nov. 16, 1959 |
| cyclophosphamide | Cytoxan Injection | | Bristol-Myers Squibb | Apr. 29, 1987 |
| cyclophosphamide | Cytoxan Tablet | | Bristol-Myers Squibb | Apr. 29, 1987 |
| cytarabine | Cytosar-U | | Pharmacia & Upjohn Company | Jun. 17, 1969 |
| cytarabine liposomal | DepoCyt | Accel. Approv. (clinical benefit not established) Intrathecal therapy of lymphomatous meningitis | Skye Pharmaceuticals | Apr. 1, 1999 |
| dacarbazine | DTIC-Dome | | Bayer | May 27, 1975 |
| dactinomycin, actinomycin D | Cosmegen | | Merck | Feb. 4, 1964 |
| dactinomycin, actinomycin D | Cosmegan | | Merck | Dec. 10, 1964 |
| Darbepoetin alfa | Aranesp | Treatment of anemia associated with chronic renal failure. | Amgen, Inc | Sep. 17, 2001 |
| Darbepoetin alfa | Aranesp | Aranesp is indicated for the treatment of anemia in patients with non-myeloid malignancies where anemia is due to the effect of concomitantly administered chemotherapy. | Amgen, Inc | Jul. 19, 2002 |
| daunorubicin liposomal | DanuoXome | First line cytotoxic therapy for advanced, HIV related Kaposi's sarcoma. | Nexstar, Inc. | Apr. 8, 1996 |
| daunorubicin, daunomycin | Daunorubicin | Leukemia/myelogenous/monocytic/ erythroid of adults/remission induction in acute lymphocytic leukemia of children and adults. | Bedford Labs | Jan. 30, 1998 |
| daunorubicin, daunomycin | Cerubidine | In combination with approved anticancer drugs for induction of remission in adult ALL. | Wyeth Ayerst | Mar. 11, 1987 |
| Denileukin diftitox | Ontak | Accel. Approv. (clinical benefit not established) treatment of patients with persistent or recurrent cutaneous T-cell lymphoma whose malignant cells express the CD25 component of the IL-2 receptor | Seragen, Inc | Feb. 5, 1999 |
| dexrazoxane | Zinecard | Accel. Approv. (clinical benefit subsequently established) Prevention of cardiomyopathy associated with doxorubicin administration | Pharmacia & Upjohn Company | May 26, 1995 |
| dexrazoxane | Zinecard | Reducing the incidence and severity of cardiomyopathy associated with doxorubicin administration in women with metastatic breast cancer who have received a cumulative doxorubicin dose of 300 mg/m2 and who will continue to receive doxorubicin therapy to maintain tumor control. It is not recommended for use with the initiation of doxorubicin therapy. | Pharmacia & Upjohn Company | Oct. 31, 2002 |
| docetaxel | Taxotere | Accel. Approv. (clinical benefit subsequently established) Treatment of patients with locally advanced or metastatic breast cancer who have progressed during anthracycline-based therapy or have relapsed during anthracycline-based adjuvant therapy. | Aventis Pharmaceutical | May 14, 1996 |
| docetaxel | Taxotere | For the treatment of locally advanced or metastatic breast cancer which has progressed during anthracycline-based treatment or relapsed during anthracycline-based adjuvant therapy. | Aventis Pharmaceutical | Jun. 22, 1998 |
| docetaxel | Taxotere | For locally advanced or metastatic non-small cell lung cancer after | Aventis Pharmaceutical | Dec. 23, 1999 |

| Approved Oncology Drugs with Approved Indications | | | | |
| --- | --- | --- | --- | --- |
| | | failure of prior platinum-based al chemotherapy. | | |
| docetaxel | Taxotere | | Aventis Pharmaceutical | Nov. 27, 2002 |
| docetaxel | Taxotere | in combination with cisplatin for the treatment of patients with unresectable, locally advanced or metastatic non-small cell lung cancer who have not previously received chemotherapy for this condition. | Aventis Pharmaceutical | Nov. 27, 2002 |
| doxorubicin | Adriamycin, Rubex | | Pharmacia & Upjohn Company | Aug. 7, 1974 |
| doxorubicin | Adriamycin PFS Injectionintravenous injection | Antibiotic, antitumor agent. | Pharmacia & Upjohn Company | Dec. 23, 1987 |
| doxorubicin liposomal | Doxil | Accel. Approv. (clinical benefit not established) Treatment of AIDS-related Kaposi's sarcoma in patients with disease that has progressed on prior combination chemotherapy or in patients who are intolerant to such therapy. | Sequus Pharmaceuticals, Inc. | Nov. 17, 1995 |
| doxorubicin liposomal | Doxil | Accel. Approv. (clinical benefit not established) Treatment of metastatic carcinoma of the ovary in patient with disease that is refractory to both paclitaxel and platinum based regimens | Sequus Pharmaceuticals, Inc. | Jun. 28, 1999 |
| DROMOSTANOLONE PROPIONATE | DROMOSTANOLONE | | Eli Lilly | Oct. 26, 1961 |
| DROMOSTANOLONE PROPIONATE | MASTERONE INJECTION | | SYNTEX | Oct. 8, 1964 |
| Elliott's B Solution | Elliott's B Solution | Diluent for the intrathecal administration of methotrexate sodium and cytarabine for the prevention or treatment of meningeal leukemia or lymphocytic lymphoma. | Orphan Medical, Inc | Sep. 27, 1996 |
| epirubicin | Ellence | A component of adjuvant therapy in patients with evidence of axillary node tumor involvement following resection of primary breast cancer. | Pharmacia & Upjohn Company | Sep. 15, 1999 |
| Epoetin alfa | epogen | EPOGENB is indicated for the treatment of anemia related to therapy with zidovudine in HIV-infected patients. EPOGENB is indicated to elevate or maintain the red blood cell level (as manifested b the hematocrit or hemoglobin determinations) and to decrease the need for transfusions in these patients. EPOGEND is not indicated for the treatment of anemia in HIV-infected patients due to other factors such as iron or folate deficiencies, hemolysis or gastrointestinal bleeding, which should be managed appropriately. | Amgen, Inc | Jul. 26, 1999 |
| Epoetin alfa | epogen | EPOGENB is indicated for the treatment of anemic patients (hemoglobin >10 to _<13 g/dL) scheduled to undergo elective, noncardiac, nonvascular surgery to reduce the need for allogeneic blood transfusions. | Amgen, Inc | Jul. 26, 1999 |
| Epoetin alfa | epogen | EPOGENB is indicated for the treatment of anemia in patients with non-myeloid malignancies where anemia is due to the effect of concomitantly administered chemotherapy. EPOGEND is indicated to decrease the need for transfusions in patients who will be receiving concomitant chemotherapy for a minimum of 2 months. EPOGENB is not indicated | Amgen, Inc | Jul. 26, 1999 |

| | | Approved Oncology Drugs with Approved Indications | | |
|---|---|---|---|---|
| | | for the treatment of anemia in cancer patients due to other factors such as iron or folate deficiencies, hemolysis or gastrointestinal bleeding, which should be managed appropriately. | | |
| Epoetin alfa | epogen | EPOGEN is indicated for the treatment of anemia associated with CRF, including patients on dialysis (ESRD) and patients not on dialysis. | Amgen, Inch | Jul. 26, 1999 |
| estramustine | Emcyt | palliation of prostate cancer | Pharmacia & Upjohn Company | Dec. 24, 1981 |
| etoposide phosphate | Etopophos | Management of refractory testicular tumors, in combination with other approved chemotherapeutic agents. | Bristol-Myers Squibb | May 17, 1996 |
| etoposide phosphate | Etopophos | Management of small cell lung cancer, first-line, in combination with other approved chemotherapeutic agents. | Bristol-Myers Squibb | May 17, 1996 |
| etoposide phosphate | Etopophos | Management of refractory testicular tumors and small cell lung cancer. | Bristol-Myers Squibb | Feb. 27, 1998 |
| etoposide, VP-16 | Vepesid | Refractory testicular tumors-in combination therapy with other approved chemotherapeutic agents in patients with refractory testicular tumors who have already received appropriate surgical, chemotherapeutic and radiotherapeutic therapy. | Bristol-Myers Squibb | Nov. 10, 1983 |
| etoposide, VP-16 | VePesid | In combination with other approved chemotherapeutic agents as first line treatment in patients with small cell lung cancer. | Bristol-Myers Squibb | Dec. 30, 1986 |
| etoposide, VP-16 | Vepesid | In combination with other approved chemotherapeutic agents as first line treatment in patients with small cell lung cancer. | Bristol-Myers Squibb | Dec. 30, 1986 |
| exemestane | Aromasin | Treatment of advance breast cancer in postmenopausal women whose disease has progressed following tamoxifen therapy. | Pharmacia & Upjohn Company | Oct. 21, 1999 |
| Filgrastim | Neupogen | | Amgen, Inc | Feb. 20, 1991 |
| Filgrastim | Neupogen | NEUPOGEN is indicated to reduce the duration of neutropenia and neutropenia-related clinical sequelae, e.g., febrile neutropenia, in patients with nonmyeloid malignancies undergoing myeloablative chemotherapy followed by marrow transplantation. | Amgen, Inc | Apr. 2, 1998 |
| Filgrastim | Neupogen | NEUPOGEN is indicated to decrease the incidence of infection, as manifested by febrile neutropenia, in patients with nonmyeloid malignancies receiving myelosuppressive anticancer drugs associated with a significant incidence of severe neutropenia with fever. | Amgen, Inc | Apr. 2, 1998 |
| Filgrastim | Neupogen | NEUPOGEN is indicated for reducing the time to neutrophil recovery and the duration of fever, following induction or consolidation hemotherapy treatment of adults with AML. | Amgen, Inc | Apr. 2, 1998 |
| floxuridine (intraarterial) | FUDR | | Roche | Dec. 18, 1970 |
| fludarabine | Fludara | Palliative treatment of patients with B-cell lymphocytic leukemia (CLL) who have not responded or have progressed during treatment with at least one standard alkylating agent containing regimen. | Berlex Laboratories Inc. | Apr. 18, 1991 |
| fluorouracil, 5-FU | Adrucil | prolong survival in combination with leucovorin | ICN Puerto Rico | Apr. 25, 1962 |
| fulvestrant | Faslodex | the treatment of hormone receptor-positive metastatic breast cancer in | IPR | Apr. 25, 2002 |

TABLE 3-continued

Approved Oncology Drugs with Approved Indications

| | | postmenopausal women with disease progression following antiestrogen therapy | | |
|---|---|---|---|---|
| gemcitabine | Gemzar | Treatment of patients with locally advanced (nonresectable stage II or III) or metastatic (stage IV) adenocarcinoma of the pancreas. Indicated for first-line treatment and for patients previously treated with a 5-fluorouracil-containing regimen. | Eli Lilly | May 15, 1996 |
| gemcitabine | Gemzar | For use in combination with cisplatin for the first-line treatment of patients with inoperable, locally advanced (Stage IIIA or IIIB) or metastatic (Stage IV) non-small cell lung cancer. | Eli Lilly | Aug. 25, 1998 |
| gemtuzumab ozogamicin | Mylotarg | Accel. Approv. (clinical benefit not established) Treatment of CD33 positive acute myeloid leukemia in patients in first relapse who are 60 years of age or older and who are not considered candidates for cytotoxic chemotherapy. | Wyeth Ayerst | May 17, 2000 |
| goserelin acetate | Zoladex Implant | Palliative treatment of advanced breast cancer in pre-and perimenopausal women. | AstraZeneca Pharmaceuticals | Dec. 18, 1995 |
| goserelin acetate | Zoladex | | AstraZeneca Pharmaceuticals | Dec. 18, 1995 |
| hydroxyurea | Hydrea | | Bristol-Myers Squibb | Dec. 7, 1967 |
| hydroxyurea | Hydrea | Decrease need for transfusions in sickle cell anemia | Bristol-Myers Squibb | Feb. 25, 1998 |
| Ibritumomab Tiuxetan | Zevalin | Accel. Approv. (clinical benefit not established) treatment of patients with relapsed or refractory low-grade, follicular, or transformed B-cell non-Hodgkin's lymphoma, including patients with Rituximab refractory follicular non-Hodgkin's lymphoma. | IDEC Pharmaceuticals Corp | Feb. 19, 2002 |
| idarubicin | Idamycin | For use in combination with other approved antileukemic drugs for the treatment of acute myeloid leukemia (AML) in adults. | Adria Laboratories | Sep. 27, 1990 |
| idarubicin | Idamycin | In combination with other approved antileukemic drugs for the treatment of acute non-lymphocytic leukemia in adults. | Pharmacia & Upjohn Company | Feb. 17, 1997 |
| ifosfamide | IFEX | Third line chemotherapy of germ cell testicular cancer when used in combination with certain other approved antineoplastic agents. | Bristol-Myers Squibb | Dec. 30, 1988 |
| imatinib mesylate | Gleevec | Accel. Approv. (clinical benefit not established) Initial therapy of chronic myelogenous leukemia | Novartis | May 10, 2001 |
| imatinib mesylate | Gleevec | Accel. Approv. (clinical benefit not established) metastatic or unresectable malignant gastrointestinal stromal tumors | Novartis | Feb. 1, 2002 |
| imatinib mesylate | Gleevec | Accel. Approv. (clinical benefit not established) Initial treatment of newly diagnosed Ph+ chronic myelogenous leukemia (CML). | Novartis | Dec. 20, 2002 |
| Interferon alfa-2a | Roferon-A | | Hoffmann-La Roche Inc | Nov. 1, 1996 |
| Interferon alfa-2b | Intron A | Interferon alfa-2b, recombinant for injection is indicated as adjuvant to surgical treatment in patients 18 years of age or older with malignant melanoma who are free of disease but at high risk for systemic recurrence within 56 days of surgery. | Schering Corp | Nov. 6, 1997 |
| Interferon alfa-2b | Intron A | Interferon alfa-2b, recombinant for injection is indicated for the initial treatment of clinically aggressive follicular Non-Hodgkin's Lymphoma in conjunction with Corp | Schering | Nov. 6, 1997 |

TABLE 3-continued

| | | Approved Oncology Drugs with Approved Indications | | |
| --- | --- | --- | --- | --- |
| | | anthracycline-containing combination chemotherapy in patients 18 years of age or older. | | |
| Interferon alfa-2b | Intron A | Interferon alfa-2b, recombinant for Injection is indicated for intralesional treatment of selected patients 18 years of age or older with condylomata acuminata involving external surfaces of the genital and perianal areas. | Schering Corp | Nov. 6, 1997 |
| Interferon alfa-2b | Intron A | Interferon alfa-2b, recombinant for Injection is indicated for the treatment of chronic hepatitis C in patients 18 years of age or older with compensated liver disease who have a history of blood or blood-product exposure and/or are HCV antibody positive. | Schering Corp | Nov. 6, 1997 |
| Interferon alfa-2b | Intron A | Interferon alfa-2b, recombinant for Injection is indicated for the treatment of chronic hepatitis B in patients 18 years of age or older with compensated liver disease and HBV replication. | Schering Corp | Nov. 6, 1997 |
| Interferon alfa-2b | Intron A | Interferon alfa-2b, recombinant for Injection is indicated for the treatment of patients 18 years of age or older with hairy cell leukemia. | Schering Corp | Nov. 6, 1997 |
| Interferon alfa-2b | Intron A | Interferon alfa-2b, recombinant for Injection is indicated for the treatment of selected patients 18 years of age or older with AIDS-Related Kaposi's Sarcoma. The likelihood of response to INTRON A therapy is greater in patients who are without systemic symptoms, who have limited lymphadenopathy and who have a relatively intact immune system as indicated by total CD4 count. | Schering Corp | Nov. 6, 1997 |
| Interferon alfa-2b | Intron A | | Schering Corp | Jun. 21, 2002 |
| Interferon alfa-2b | Intron A | | Schering Corp | Jun. 21, 2002 |
| Interferon alfa-2b | Intron A Intron A | | Schering Corp | Jun. 21, 2002 |
| irinotecan | Camptosar | Accel. Approv. (clinical benefit subsequently established) Treatment of patients with metastatic carcinoma of the colon or rectum whose disease has recurred or progressed following 5-FU-based therapy. | Pharmacia & Upjohn Company | Jun. 14, 1996 |
| irinotecan | Camptosar | Follow up of treatment of metastatic carcinoma of the colon or rectum whose disease has recurred or progressed following 5-FU-based therapy. | Pharmacia & Upjohn Company | Oct. 22, 1998 |
| irinotecan | Camptosar | For first line treatment in combination with 5-FU/leucovorin of metastatic carcinoma of the colon or rectum. | Pharmacia & Upjohn Company | Apr. 20, 2000 |
| letrozole | Femara | Treatment of advanced breast cancer in postmenopausal women. | Novartis | Jul. 25, 1997 |
| letrozole | Femara | First-line treatment of postmenopausal women with hormone receptor positive or hormone receptor unknown locally advanced or metastatic breast cancer. | Novartis | Jan. 10, 2001 |
| letrozole | Femara | | Novartis | Jan. 17, 2003 |
| leucovorin | Wellcovorin, Leucovorin | Leucovorin calcium is indicated for use in combination with 5-fluorouracil to prolong survival in the palliative treatment of patients the with advanced colorectal cancer. | Immunex Corporation | Jun. 20, 1952 |
| leucovorin | Leucovorin | | Immunex Corporation | Jan. 30, 1987 |

TABLE 3-continued

| | | Approved Oncology Drugs with Approved Indications | | |
|---|---|---|---|---|
| leucovorin | Leucovorin | | Immunex Corporation | Jan. 30, 1987 |
| leucovorin | Leucovorin | | Immunex Corporation | Aug. 31, 1988 |
| leucovorin | Leucovorin | In combination with fluorouracil to prolong survival in the palliative treatment of patients with advanced colorectal cancer. | Lederle Laboratories | Dec. 12, 1991 |
| levamisole | Ergamisol | Adjuvant treatment in combination with 5-fluorouracil after surgical resection in patients with Dukes' Stage C colon cancer. | Janssen Research Foundation | Jun. 18, 1990 |
| lomustine, CCNU | CeeBU | | Bristol-Myers Squibb | Aug. 4, 1976 |
| meclorethamine, nitrogen mustard | Mustargen | | Merck | Mar. 15, 1949 |
| megestrol acetate | Megace | | Bristol-Myers Squibb | Aug. 18, 1971 |
| melphalan, L-PAM | Alkeran | | GlaxoSmith Kline | Jan. 17, 1964 |
| melphalan, L-PAM | Alkeran | Systemic administration for palliative treatment of patients with multiple myeloma for whom oral therapy is not appropriate. | GlaxoSmith Kline | Nov. 18, 1992 |
| mercaptopurine, 6-MP | Purinethol | | GlaxoSmith Kline | Sep. 11, 1953 |
| mesna | Mesnex | Prevention of ifosfamide-induced hemorrhagic cystitis | Asta Medica | Dec. 30, 1988 |
| methotrexate | Methotrexate | | Lederle Laboratories | Dec. 7, 1953 |
| methotrexate | Methotrexate | | Lederle Laboratories | Aug. 10, 1959 |
| methotrexate | Methotrexate | | Lederle Laboratories | Nov. 1, 1971 |
| methotrexate | Methotrexate | | Lederle Laboratories | Nov. 1, 1971 |
| methotrexate | Methotrexate | osteosarcoma | Lederle Laboratories | Apr. 7, 1988 |
| methotrexate | Methotrexate | | Lederle Laboratories | Oct. 31, 1988 |
| methoxsalen | Uvadex | For the use of UVADEX with the UVAR Photopheresis System in the palliative treatment of the skin manifestations of cutaneous T-cell lymphoma (CTCL) that is unresponsive to other forms of treatment. | Therakos | Feb. 25, 1999 |
| mitomycin C | Mutamycin | | Bristol-Myers Squibb | May 28, 1974 |
| mitomycin C | Mitozytrex | Therapy of disseminated adenocarcinoma of the stomach or pancreas in proven combinations with other approved chemotherapeutic agents and as palliative treatment when other modalities have failed. | Supergen | Nov. 14, 2002 |
| mitotane | Lysodren | | Bristol-Myers Squibb | Jul. 8, 1970 |
| mitoxantrone | Novantrone | For use in combination with corticosteroids as initial chemotherapy for the treatment of patients with pain related to Corporation advanced hormone-refractory prostate cancer. | Immunex | Nov. 13, 1996 |
| mitoxantrone | Novantrone | For use with other approved drugs in the initial therapy for acute nonlymphocytic leukemia (ANLL) in adults. | Lederle Laboratories | Dec. 23, 1987 |
| nandrolone phenpropionate | Durabolin-50 | | Organon | Oct. 30, 1959 |
| Nofetumomab | Verluma | | Boehringer Ingelheim Pharma KG (formerly Dr. Karl Thomae GmbH) | Aug. 20, 1996 |
| Oprelvekin | Neumega | | Genetics Institute, Inc | Nov. 25, 1997 |

TABLE 3-continued

| Approved Oncology Drugs with Approved Indications | | | | |
|---|---|---|---|---|
| Oprelvekin | Neumega | | Genetics Institute, Inc | Sep. 18, 2002 |
| Oprelvekin | Neumega | Neumega is indicated for the prevention of severe thrombocytopenia and the reduction of the need for platelet transfusions following myelosuppressive chemotherapy in adult patients with nonmyeloid malignancies who are at high risk of severe thrombocytopenia. | Genetics Institute, Inc | Sep. 18, 2002 |
| oxaliplatin | Eloxatin | Accel. Approv. (clinical benefit not established) in combination with infusional 5-FU/LV, is indicated for the treatment of patients with metastatic carcinoma of the colon or rectum whose disease has recurred or progressed during or within 6 months of completion of first line therapy with the combination of bolus 5-FU/LV and irinotecan. | Sanofi Synthelabo | Aug. 9, 2002 |
| paclitaxel | Paxene | treatment of advanced AIDS-related Kaposi's sarcoma after failure of first line or subsequent systemic chemotherapy | Baker Norton Pharmaceuticals, Inc | Dec. 24, 1997 |
| paclitaxel | Taxol | Treatment of patients with metastatic carcinoma of the ovary after failure of first-line or subsequent chemotherapy. | Bristol-Myers Squibb | Dec. 29, 1992 |
| paclitaxel | Taxol | Treatment of breast cancer after failure of combination chemotherapy for metastatic disease or relapse within 6 months of adjuvant chemotherapy. Prior therapy should have included an anthracycline unless clinically contraindicated. | Bristol-Myers Squibb | Apr. 13, 1994 |
| paclitaxel | Taxol | New dosing regimen for patients who have failed initial or subsequent chemotherapy for metastatic carcinoma of the ovary | Bristol-Myers Squibb | Jun. 22, 1994 |
| paclitaxel | Taxol | Second line therapy for AIDS related Kaposi's sarcoma. | Bristol-Myers Squibb | Aug. 4, 1997 |
| paclitaxel | Taxol | For first-line therapy for the treatment of advanced carcinoma of the ovary in combination with cisplatin. | Bristol-Myers Squibb | Apr. 9, 1998 |
| paclitaxel | Taxol | For use in combination with cisplatin, for the first-line treatment of non-small cell lung cancer in patients who are not candidates for potentially curative surgery and/or radiation therapy. | Bristol-Myers Squibb | Jun. 30, 1998 |
| paclitaxel | Taxol | For the adjuvant treatment of node-positive breast cancer administered sequentially to standard doxorubicin-containing combination therapy. | Bristol-Myers Squibb | Oct. 25, 1999 |
| paclitaxel | Taxol | First line ovarian cancer with 3 hour infusion. | Bristol-Myers Squibb | Jun. 20, 2000 |
| pamidronate | Aredia | Treatment of osteolytic bone metastases of breast cancer in conjunction with standard antineoplastic therapy. | Novartis | Sep. 22, 1998 |
| pegademase | Adagen (Pegademase Bovine) | Enzyme replacement therapy for patients with severe combined immunodeficiency as a result of adenosine deaminase deficiency. | Enzon | Mar. 21, 1990 |
| Pegaspargase | Oncaspar | | Enzon, Inc | Feb. 1, 1994 |
| Pegfilgrastim | Neulasta | Neulasta is indicated to decrease the incidence of infection, as manifested by febrile neutropenia, in patients with non-myeloid malignancies receiving myelosuppressive anti-cancer drugs associated with a clinically significant incidence of febrile neutropenia. | Amgen, Inc | Jan. 31, 2002 |

TABLE 3-continued

| | | Approved Oncology Drugs with Approved Indications | | |
|---|---|---|---|---|
| pentostatin | Nipent | Single agent treatment for adult patients with alpha interferon refractory hairy cell leukemia. | Parke-Davis Pharmaceutical Co. | Oct. 11, 1991 |
| pentostatin | Nipent | Single-agent treatment for untreated hairy cell leukemia patients with active disease as defined by clinically significant anemia, neutropenia, thrombocytopenia, or disease-related symptoms. (Supplement for front-line therapy.) | Parke-Davis Pharmaceutical Co. | Sep. 29, 1993 |
| pipobroman | Vercyte | | Abbott Labs | Jul. 1, 1966 |
| plicamycin, mithramycin | Mithracin | | Pfizer Labs | May 5, 1970 |
| porfimer sodium | Photofrin | For use in photodynamic therapy (PDT) for palliation of patients with completely obstructing esophageal cancer, or patients with partially obstructing esophageal cancer who cannot be satisfactorily treated with ND-YAG laser therapy. | QLT Phototherapeutics Inc. | Dec. 27, 1995 |
| porfimer sodium | Photofrin | For use in photodynamic therapy for treatment of microinvasive endobronchial nonsmall cell lung cancer in patients for whom surgery and radiotherapy are not indicated. | QLT Phototherapeutics Inc. | Jan. 9, 1998 |
| porfimer sodium | Photofrin | For use in photodynamic therapy (PDT) for reduction of obstruction and palliation of symptoms in patients with completely or partially obstructing endobroncial nonsmall cell lung cancer (NSCLC). | QLT Phototherapeutics Inc. | Dec. 22, 1998 |
| procarbazine | Matulane | | Sigma Tau Pharms | Jul. 22, 1969 |
| quinacrine | Atabrine | | Abbott Labs | Dec. 7, 1964 |
| Rasburicase | Elitek | ELITEK is indicated for the initial management of plasma uric acid levels in pediatric patients with leukemia, lymphoma, and solid tumor malignancies who are receiving anti-cancer therapy expected to result in tumor lysis and subsequent elevation of plasma uric acid. | Sanofi-Synthelabo, Inc | Jul. 12, 2002 |
| Rituximab | Rituxan | | Genentech, Inc | Nov. 26, 1997 |
| Sargramostim | Prokine | | Immunex Corp | Nov. 7, 1996 |
| streptozocin | Zanosar | Antineoplastic agent. | Pharmacia & Upjohn Company | May 7, 1982 |
| talc | Sclerosol | For the prevention of the recurrence of malignant pleural effusion in symptomatic patients. | Bryan | Dec. 24, 1997 |
| tamoxifen | Nolvadex | | AstraZeneca Pharmaceuticals | Dec. 30, 1977 |
| tamoxifen | Nolvadex | As a single agent to delay breast cancer recurrence following total mastectomy and axillary dissection in postmenopausal women with breast cancer (T1-3, N1, M0) | AstraZeneca Pharmaceuticals | Dec. 3, 1986 |
| tamoxifen | Nolvadex | For use in premenopausal women with metastatic breast cancer as an alternative to oophorectomy or ovarian irradiation | AstraZeneca Pharmaceuticals | Mar. 16, 1989 |
| tamoxifen | Nolvadex | For use in women with axillary node-negative breast cancer adjuvant therapy. | AstraZeneca Pharmaceuticals | Jun. 21, 1990 |
| tamoxifen | Nolvadex | Metastatic breast cancer in men. | AstraZeneca Pharmaceuticals | Apr. 1, 1993 |
| tamoxifen | Nolvadex | Equal bioavailability of a 20 mg Nolvadex tablet taken once a day to a 10 mg Nolvadex tablet taken twice a day. | AstraZeneca Pharmaceuticals | Mar. 21, 1994 |
| tamoxifen | Nolvadex | to reduce the incidence of breast cancer in women at high risk for breast cancer | AstraZeneca Pharmaceuticals | Oct. 29, 1998 |
| tamoxifen | Nolvadex | In women with DCIS, following breast surgery and radiation, | AstraZeneca Pharmaceuticals | Jun. 29, 2000 |

TABLE 3-continued

| | | Approved Oncology Drugs with Approved Indications | | |
|---|---|---|---|---|
| | | Nolvadex is indicated to reduce the risk of invasive breast cancer. | | |
| temozolomide | Temodar | Accel. Approv. (clinical benefit not established) Treatment of adult patients with refractory anaplastic astrocytoma, i.e., patients at first relapse with disease progression on a nitrosourea and procarbazine containing regimen | Schering | Aug. 11, 1999 |
| teniposide, VM-26 | Vumon | In combination with other approved anticancer agents for induction therapy in patients with refractory childhood acute lymphoblastic leukemia (all). | Bristol-Myers Squibb | Jul. 14, 1992 |
| testolactone | Teslac | | Bristol-Myers Squibb | Jun. 3, 1969 |
| testolactone | Teslac | | Bristol-Myers Squibb | May 27, 1970 |
| thioguanine, 6-TG | Thioguanine | | GlaxoSmith Kline | Jan. 18, 1966 |
| thiotepa | Thioplex | | Immunex Corporation | Mar. 9, 1959 |
| thiotepa | Thioplex | | Immunex Corporation | Dec. 22, 1994 |
| thiotepa | Thioplex | | Lederle Laboratories | Aug. 15, 1990 |
| topotecan | Hycamtin | Treatment of patients with metastatic carcinoma of the ovary after failure of initial or subsequent chemotherapy. | GlaxoSmith Kline | May 28, 1996 |
| topotecan | Hycamtin | Treatment of small cell lung cancer sensitive disease after failure of first-line chemotherapy. In clinical studies submitted to support approval, sensitive disease was defined as disease responding to chemotherapy but subsequently progressing at least 60 days (in the phase 3 study) or at least 90 days (in the phase 2 studies) after chemotherapy | GlaxoSmith Kline | Nov. 30, 1998 |
| toremifene | Fareston | Treatment of advanced breast cancer in postmenopausal women. | Orion Corp. | May 29, 1997 |
| Tositumomab | Bexxar | Accel. Approv. (clinical benefit not established) Treatment of patients with CD20 positive, follicular, non-Hodgkin's lymphoma, with and without transformation, whose disease is refractory to Rituximab and has relapsed following chemotherapy | Corixa Corporation | Jun. 27, 2003 |
| Trastuzumab | Herceptin | HERCEPTIN as a single agent is indicated for the treatment of patients with metastatic breast cancer whose tumors overexpress the HER2 protein and who have received one or more chemotherapy regimens for their metastatic disease. | Genentech, Inc | Sep. 25, 1998 |
| Trastuzumab | Herceptin | Herceptin in combination with paclitaxel is indicated for treatment of patients with metastatic breast cancer whose tumors overexpress the HER-2 protein and had not received chemotherapy for their metastatic disease | Genentech, Inc | Feb. 9, 2000 |
| Trastuzumab | Herceptin | | Genentech, Inc | Dec. 11, 2001 |
| Trastuzumab | Herceptin | | Genentech, Inc | Aug. 28, 2002 |
| Trastuzumab | Herceptin | | Genentech, Inc | Aug. 28, 2002 |
| tretinoin, ATRA | Vesanoid | Induction of remission in patients with acute promyelocytic leukemia (APL) who are refractory to or unable to tolerate anthracycline based cytotoxic chemotherapeutic regimens. | Roche | Nov. 22, 1995 |

TABLE 3-continued

| Approved Oncology Drugs with Approved Indications | | | | |
|---|---|---|---|---|
| Uracil Mustard | Uracil Mustard Capsules | | Roberts Labs | Sep. 13, 1962 |
| valrubicin | Valstar | For intravesical therapy of BCG-refractory carcinoma in situ (CIS) of the urinary bladder in patients for whom immediate cystectomy would be associated with unacceptable morbidity or mortality. | Anthra --> Medeva | Sep. 25, 1998 |
| vinblastine | Velban | | Eli Lilly | Nov. 5 1965 |
| vincristine | Oncovin | | Eli Lilly | Jul. 10, 1963 |
| vincristine | Oncovin | | Eli Lilly | Jul. 10, 1963 |
| vincristine | Oncovin | | Eli Lilly | Jul. 10, 1963 |
| vincristine | Oncovin | | Eli Lilly | Jul. 10, 1963 |
| vincristine | Oncovin | | Eli Lilly | Jul. 10, 1963 |
| vincristine | Oncovin | | Eli Lilly | Jul. 10, 1963 |
| vincristine | Oncovin | | Eli Lilly | Jul. 10, 1963 |
| vinorelbine | Navelbine | Single agent or in combination with cisplatin for the first-line treatment of ambulatory patients with unresectable, advanced non-small cell lung cancer (NSCLC). | GlaxoSmith Kline | Dec. 23, 1994 |
| vinorelbine | Navelbine | Navelbine is indicated as a single agent or in combination with cisplatin for the first-line treatment of ambulatory patients with unreseactable, advanced non-small cell lung cancer (NSCLC). In patients with Stage IV NSCLC, Navelbine is indicated as a single agent or in combination with cisplatin. In Stage III NSCLC, Navelbine is indicated in combination with cisplatin. | GlaxoSmith Kline | Nov. 5, 2002 |
| zoledronate | Zometa | The treatment of patients with multiple myeloma and patients with documented bone metastases from solid tumors, in conjunction with standard antineoplastic therapy. Prostate cancer should have progressed after treatment with at least one hormonal therapy | Novartis | Feb. 22, 2002 |

Fatty liver disease, steatosis, a medical condition affecting over 25% of the global population and a common adverse event reported in drug induced liver injury and during prescription drug use. While fatty liver disease can range from simple steatosis to nonalcoholic steatohepatitis (NASH), cirrhosis, and hepatocellular carcinoma, one of the early and more severe forms of the disease is microvesicular steatosis. Microvesicular steatosis is often associated with mitochondrial dysfunction and can be life threatening when long lasting. Drugs associated with microvesicular steatosis include Valproate, Aspirin, glucocorticoids, anti-retroviral drugs (e.g. Stavudine), nonsteroidal anti-inflammatory drugs (e.g. Bromfenac) and cocaine.

According to some embodiments of the invention there is a sensor-integrated liver on chip array in which oxygen is monitored using two-frequency phase modulation of tissue-embedded phosphorescent microprobes, while glucose, lactate and temperature are measured in real time using microfluidic electrochemical sensors. Such a microphysiological platform permits the calculation of dynamic changes in metabolic fluxes around central carbon metabolism, producing a unique metabolic fingerprint of the liver's response to stimuli. Using this platform, the present inventors studied the dynamics of human liver response to the epilepsy drug Valproate (Depakine™) and the antiretroviral medication Stavudine (Zerit™). Using E6/E7$^{LOW}$ hepatocytes the present inventors show TC$_{50}$ of 2.5 and 0.8 mM, respectively, coupled with a significant induction of steatosis in 2D and 3D cultures. Time to onset analysis showed slow progressive damage starting only 15-20 hours post-exposure.

However, flux balance analysis showed a rapid disruption of metabolic homeostasis occurring below the threshold of cellular damage. While Valproate exposure led to a sustained 15% increase in lipogenesis followed by mitochondrial stress, Stavudine exposure showed only a transient 5% increase in lipogenesis followed by its inhibition suggesting disruption of β-oxidation. These data demonstrate the importance of tracking metabolic stress as a predictor of clinical outcome.

The method according to some embodiments of an aspect of the invention includes the use of oxygen microsensors embedded in human micro-tissues in a multi-well plate (e.g., 384-well plate) format. The present inventors measure Time to Onset (TTO), the period of time between the exposure to the drug and the measured effect. The present inventors showed that the Time to Onset of all drugs examined to date is dose dependent. Thus, one can extrapolate the data into infinity to analytically determine the dose in which the drug will not be toxic to the human tissue even during infinite prolonged exposure.

In some embodiments, the dose range that is detected by the method using the plurality of TTO values is the upper bound of the therapeutic window of the pharmaceutically active agent under analysis.

As used herein, the terms "therapeutic window" and "pharmaceutical window" are interchangeable and refer to the range of pharmacodynamic effects conferred by a range of dosages of a particular pharmaceutically active agent, wherein the pharmacodynamic effects range from the lowest level of an effective treatment of a medical condition (therapeutic effect) to a highest level of tolerable adverse effects. Hence, a therapeutic window can be correlated, via a pharmacokinetic profile, to the range of amounts of a particular pharmaceutically active agent between the amount that confers a desired therapeutic effect (a therapeutically effective amount or dose), and the amount that causes more adverse effects than desired effects, the former amount being the lower bound of the therapeutic window, and the latter amount being the upper bound of the therapeutic window.

Figure 17:
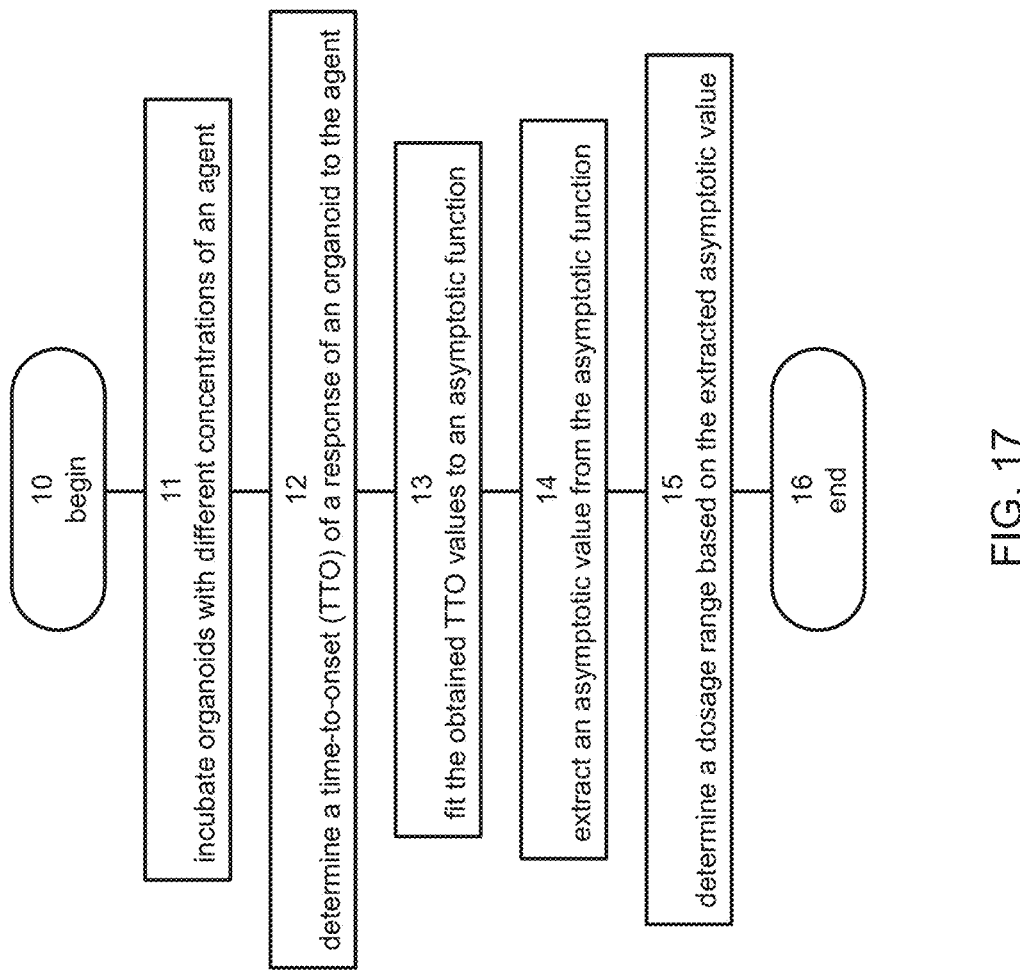
FIG. 17 is a flowchart diagram of a method suitable for determining a dose range of a pharmaceutically active agent to be administered for treating a disease or condition, according to various exemplary embodiments of the present invention.

FIG. 17 is a flowchart diagram of a method suitable for determining a dose range of a pharmaceutically active agent to be administered for treating a disease or condition, according to various exemplary embodiments of the present invention. It is to be understood that, unless otherwise defined, the operations described hereinbelow can be executed either contemporaneously or sequentially in many combinations or orders of execution. Specifically, the ordering of the flowchart diagrams is not to be considered as limiting. For example, two or more operations, appearing in the following description or in the flowchart diagrams in a particular order, can be executed in a different order (e.g., a reverse order) or substantially contemporaneously. Additionally, several operations described below are optional and may not be executed.

The method begins at 10 and optionally and preferably continues to 11 at which a plurality of organoids with a respective plurality of different concentrations of the agent are incubated. According to some embodiments of the invention, the incubation is simultaneous for all organoids. For example, the organoids can be incubated in a plurality of wells arranged as an array, wherein at least two of the wells contain one or more organoids with a different concentration of the agent. Typically, the wells are wells of a multi-well plate, such as, but not limited to, a microwell plate. In experiments performed by the present Inventors, a 384 well plate was used for the incubation 11. In some embodiments of the present invention the incubation is within bioreactors under condition of a steady flow of the agent to the organoids.

The method can then proceed to 12 at which the function of the organoids is monitored over a time period to determine, for each of at least a portion of the organoids, a TTO of a response of the organoid to the agent. The time period can be at least 30 hours, or at least 35 hours, or at least 40 hours, or at least 45 hours, or at least 50 hours, or at least 55 hours, or at least 60 hours, or at least 70 hours, or at least 80 hours, or at least 90 hours, or at least 100 hours. Preferably, the time period is at least 10 hours, more preferably at least 24 hours. In various exemplary embodiments of the invention the monitoring is in the absence of flow of the agent to and from the organoids. In various exemplary embodiments of the invention the culture medium in the wells is not replaced during the time period of the monitoring.

The function of the organoids that is monitored can be, for example, the organoid viability (e.g., respiration of oxygen), the organoid metabolic function, and the like. For example, the function can be monitored by monitoring oxygen levels, which are indicative of the viability of the organoids. Monitoring of oxygen levels can be done, by embedding the organoids with oxygen sensors as further detailed herein, and monitoring signals emitted by the oxygen sensors.

The TTO can be defined as a change in the time-dependence of the respective organoid's function (e.g., as indicated by the oxygen level) that is chartered by a slope which above a predetermined threshold. As a representative example, when the level of oxygen raises by more than p % per hour, the method can determine that a response onset has occurred, and define the time at which such response onset occurred as the TTO. A representative example for the value of the threshold p is from about 5 to about 50, but other thresholds can be defined, in accordance with some embodiments of the present invention.

According to some embodiments of the invention, the oxygen levels are indicative of the metabolic function. For example, utilization of oxygen to produce ATP, in addition to or instead of other pathways; utilization of oxygen in the citric cycle to produce metabolites; respiratory capacity as a function of cellular development and/or maturation; oxygen consumption as a measure of disease state (e.g., liver cells with HCV infection).

Operation 12 produces a plurality of TTO values, one for each of at least a portion of the different concentrations of the agent. The method continues to 13 at which the TTO values produced at 12 are fitted to an asymptotic function. Preferably, the asymptotic function is an asymptotically decaying function. Representative examples of asymptotic functions suitable for the present embodiments including, without limitation, an exponential function, a non-exponential function, e.g., a Lorenzian function, a modified Bessel function, a power-decaying function and the like. The fit of the TTO values to the asymptotic function produces one or more parameters describing the function.

For example, when the function is of the form $A/(1-\exp(t/\tau))$, where t represents the TTO values, the fit produces fitted values for the parameters A and $\tau$. When the function is of the form $A+x^{-\alpha t}$, where t represents the TTO values, the fit produces fitted values for the parameters A and $\alpha$. The skilled person, provided with the details described herein, would know how to produce parameters by fitting the TTO values to other function forms.

The method continues to 13 at which an asymptotic value is extracted from the asymptotic function. The asymptotic value is the value of the asymptotic function, when its argument t approaches infinity. For example, in the above examples of $A/(1-\exp(t/\tau))$ and $A+x^{-\alpha t}$, the asymptotic value is the value of the parameter A since when t approaches infinity both these functions approach A. It is stressed that it is not necessary to have a TTO value that approaches infinity. Once the TTO values are fitted to the function, its asymptotic value can be obtained mathematically by taking the appropriate limit of its argument t.

The method proceeds to 15 at which a range of a dose amount is determined based on the extracted asymptotic value. Typically, once the asymptotic value of the function is known, it is used to determine the value of the function at a steady state and the range of dose amount can be determined based on the steady state value. According to some embodiments of the invention, the dose range is determined by selecting a dose range such that a peak plasma concentration of the agent in a blood sample of a test subject administered with the agent is less than the asymptotic value. A representative example of a procedure for determining the dose range is described in the Examples section that follows.

The present embodiments also contemplate determining an exposure time to the agent based on a received value describing a dose amount. In these embodiments, exposure time is determined using the asymptotic function. For example, the exposure time can be a TTO of a response of an organoid to the agent, had the organoid been incubated with a concentrations of the agent that correspond to the dose amount. In these embodiments, the value of the asymptotic function can be compared to the received value describing the dose amount, and the value of the argument t of the function can be calculated or estimated. The calculated or estimated value of the argument is then defined as the exposure time.

The method ends at 16.

Figure 18:
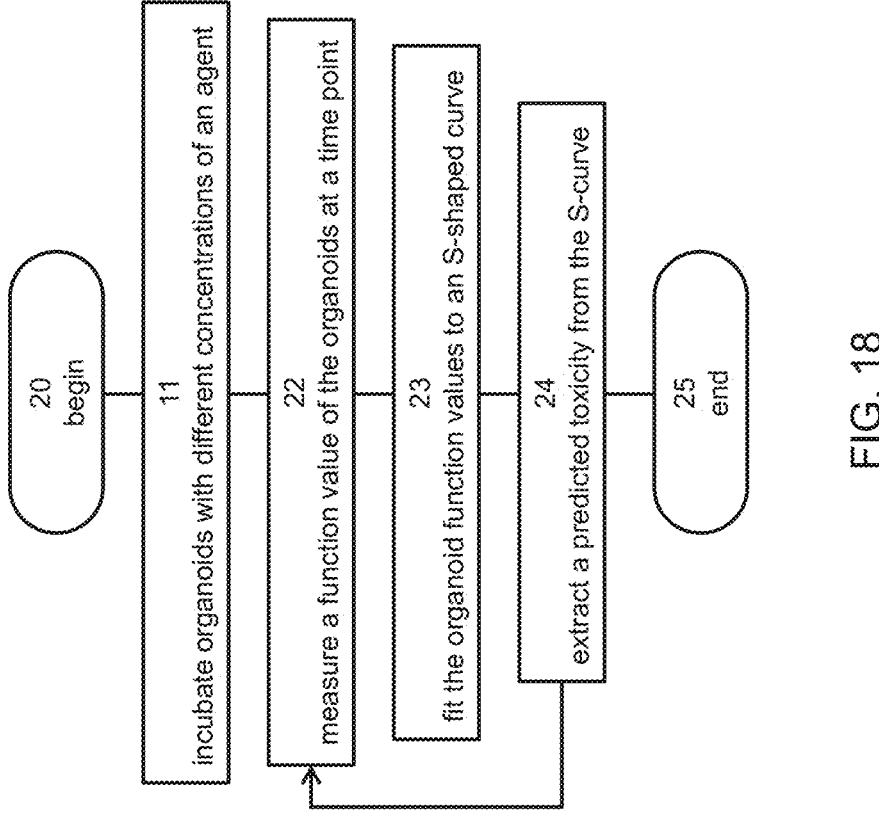
FIG. 18 is a flowchart diagram of a method suitable for determining a toxicity of a pharmaceutically active agent to be administered for treating a disease or condition.

FIG. 18 is a flowchart diagram of a method suitable for determining a toxicity of a pharmaceutically active agent to be administered for treating a disease or condition. The method begins at 20 and continues to 11 at which a plurality of organoids are incubated with a respective plurality of different concentrations of the agent, as further detailed hereinabove. The incubation is optionally and preferably simultaneous for all organoids.

According to some embodiments of the invention, incubating is within bioreactors under condition of a steady flow of said agent to said organoids.

The method continues to 22 at which a function of the organoids is measured at a time point. The function can be any of the aforementioned monitored organoid's functions such as, but not limited to, viability, metabolic function, and the like. The function is preferably measured for each of at least a few of the incubated organoids, so that operation 22 produces a plurality of organoid-function values, one for each of the respective concentrations. Preferably, a time-period from the beginning of the incubation to the time point at which the measurement 22 is executed corresponds to a pre-selected exposure time of the subject to the agent.

According to some embodiments of the invention, the measuring 22 is in the absence of flow of the agent to and from the organoids.

The method proceeds to 23 at which the produced organoid-function values are fitted to an S-shaped curve, and to 24 at which a predicted toxicity value of the agent for the pre-selected exposure time is extracted from the S-shaped curve. In some embodiments of the present invention the predicted toxicity is the median toxic concentration, but other percentiles for expressing the toxicity are also contemplated.

The S-shaped curve can be described by any mathematical function f(c) whose shape resembles an S-shape, where c represents the different concentrations. Representative examples including, without limitation, a sigmoid function, an arctangent function, a hyperbolic tangent function, and an inverse square root unit function.

The predicted toxicity value is optionally and preferably extracted by setting the predicted toxicity value to be one of the parameters of the fit executed at 23, preferably the parameters the scales the concentration. A parameter is said to "scale the concentration" when it divides the variable of the function that represents the S-curve. For example, when the S-curve is represented by an arctangent function, f(c) can be set to $a_1 + a_2 \cdot \arctan(c/a_3)$, and when the S-curve is represented by hyperbolic tangent function f(c) can be set to $a_1 + a_2 \cdot \tan h(c/a_3)$, where c represents the different concentrations and $a_3$ scales the concentration.

According to a preferred embodiment of the invention, the S-shaped curve is a sigmoid. For example, the sigmoid can be of the form $a_1 + a_2/[1 + (c/a_3)^h]$, where $a_1$, $a_2$, $a_3$ and h are sigmoid parameters, c represents the different concentrations. In these embodiments, $a_3$ optionally and preferably represents the toxicity of the agent. In some embodiments of the present invention the fitting 23 comprises applying a four-parameter fit to provide a value for the sigmoid parameters. In some embodiments of the present invention one of $a_1$ and $a_2$ is predetermined and the fitting 23 comprises applying a three-parameter fit to provide a value for the remaining three sigmoid parameters. In some embodiments of the present invention $a_1$ and $a_2$ are predetermined wherein the fitting 23 comprises applying a two-parameter fit to provide a value for the parameters $a_3$ and h.

As a representative example $a_1$ can be set to 0. Alternatively or additionally, $a_2$ can be set to 1. Other values for the parameters are also contemplated.

According to some embodiments of the invention, the method loops back from 24 to 22 so as to repeat the measuring 22, the fitting 23, and the extraction 24 at a different time point corresponding to a different pre-selected exposure time. Each loopback provides a predicted toxicity value, one for each pre-selected exposure time. Thus, the present embodiments contemplate providing a set of predicted toxicity values for a respective set of exposure times. In various exemplary embodiments of the invention the set of predicted toxicity values is analyzed as a function of the exposure time. Such analysis can provide predicted toxicity values also for exposure times for which there was no measurement or not fit. The analysis can include interpolation or extrapolation. When analysis comprises extrapolation the method optionally and preferably firstly identifies a plateau over the predicted toxicity values, as a function of the exposure time, and then extrapolates the plateau to determine a predicted toxicity value for an exposure time that is longer than each of the pre-selected exposure times.

The method ends at 25.

According to an aspect of some embodiments of the invention there is provided a method of determining a dose range of a pharmaceutically active agent to be administered for treating a disease or condition, the method comprising:

incubating a plurality of organoids with a respective plurality of different concentrations of said agent;

monitoring function of said organoids over a time period to determine, for each organoid, a time-to-onset (TTO) of a response of said organoid to said agent, thereby providing a plurality of TTO values, one for each of said concentrations;

fitting said plurality of TTO values to an asymptotic function;

extracting an asymptotic value from said asymptotic function; and determining a range of a dose amount based on said extracted asymptotic value.

The phrase "lowest exposure level" (LEL) can be defined as range of values that match the horizontal asymptote of a concentration versus time to onset (TTO) or any other onset indicative term. LEL is in-fact the concentration for which onset of damage is at, or predicted to be at infinite time.

According to some embodiments of the invention, monitoring is in the absence of flow of said agent to and from said organoids.

According to some embodiments of the invention, incubating is simultaneous for all organoids.

According to some embodiments of the invention, incubating is within bioreactors under condition of a steady flow of said agent to said organoids.

The function of the organoids can be the organoid viability (e.g., respiration of oxygen) and/or the organoid metabolic function.

According to some embodiments of the invention, monitoring said function, comprises monitoring oxygen levels.

According to some embodiments of the invention, monitoring said viability, comprises monitoring oxygen levels.

According to some embodiments of the invention, the oxygen levels are indicative of the metabolic function. For example, utilization of oxygen to produce ATP, in addition to or instead of other pathways; utilization of oxygen in the citric cycle to produce metabolites; respiratory capacity as a function of cellular development and/or maturation; oxygen consumption as a measure of disease state (e.g., liver cells with HCV infection).

According to some embodiments of the invention, the organoids are embedded with oxygen sensors, and wherein said monitoring said oxygen levels comprises monitoring signals emitted by said oxygen sensors.

According to some embodiments of the invention, the time period is at least 10 hours.

According to some embodiments of the invention, the time period is at least 24 hours.

According to some embodiments of the invention, the time period is at least 30 hours, at least 30 hours, at least 35 hours, at least 40 hours, at least 45 hours, at least 50 hours, at least 55 hours, at least 60 hours, at least 70 hours, at least 80 hours, at least 90 hours, at least 100 hours at least 100 hours.

According to some embodiments of the invention, the time period is at least 10 hours without replacing the culture medium (medium change).

According to some embodiments of the invention, the time period is at least 24 hours without replacing the culture medium (medium change).

According to some embodiments of the invention, the time period is at least 30 hours, at least 30 hours, at least 35 hours, at least 40 hours, at least 45 hours, at least 50 hours, at least 55 hours, at least 60 hours, at least 70 hours, at least 80 hours, at least 90 hours, at least 100 hours at least 100 hours without replacing the culture medium (medium change).

It should be noted that the time period can be extended for more than a month given routine medium changes.

According to some embodiments of the invention, the asymptotic function, is an asymptotically decaying function.

According to some embodiments of the invention, the asymptotic function, is an exponential function.

According to some embodiments of the invention, the asymptotic function, is a non-exponential function.

According to some embodiments of the invention, determining the dose range comprises selecting a dose range such that a peak plasma concentration of said agent in a blood sample of a test subject administered with said agent is less than said asymptotic value.

According to some embodiments of the invention, incubating said organoids is executed in a multi-well plate.

According to some embodiments of the invention, the method comprising receiving a value describing a dose amount, and using said asymptotic function for determining an exposure time to said agent, said exposure time being a TTO of a response of an organoid to said agent, had said organoid been incubated with a concentrations of said agent that correspond to said dose amount.

According to an aspect of some embodiments of the invention there is provided a method of determining a toxicity of a pharmaceutically active agent to be administered for treating a disease or condition, the method comprising:

incubating a plurality of organoids with a respective plurality of different concentrations of said agent;

measuring function of said organoids at a time point, thereby providing a plurality of organoid-function values, one for each of said concentrations, wherein a time-period from a beginning of said incubation to said time point corresponds to a pre-selected exposure time of a subject to the agent;

fitting said plurality of organoid-function values to an S-shaped curve; and extracting from said S-shaped curve a predicted toxicity value of the agent for said pre-selected exposure time.

According to some embodiments of the invention, the method comprising repeating said measuring, said fitting, and said extracting at least once, at a different time point corresponding to a different pre-selected exposure time, thereby providing a plurality of predicted toxicity values, one for each pre-selected exposure time.

According to some embodiments of the invention, the method comprising identifying a plateau over said predicted toxicity values, as a function of time, and extrapolating said plateau to determine a predicted toxicity value for an exposure time that is longer than each of said pre-selected exposure times.

According to some embodiments of the invention, measuring is in the absence of flow of said agent to and from said organoids.

According to some embodiments of the invention, the incubation is simultaneous for all organoids.

According to some embodiments of the invention, incubating is within bioreactors under condition of a steady flow of said agent to said organoids.

According to some embodiments of the invention, the measuring said function comprises measuring oxygen levels.

According to some embodiments of the invention, the organoids are embedded with oxygen sensors, and wherein said measuring said oxygen levels comprises measuring signals emitted by said oxygen sensors.

According to some embodiments of the invention, the time period is at least 10 hours.

According to some embodiments of the invention, the time period is at least 24 hours.

According to some embodiments of the invention, the asymptotic function, is an asymptotically decaying function.

According to some embodiments of the invention, the S-shaped curve is a sigmoid.

According to some embodiments of the invention, the sigmoid is $a_1 + a_2/[1+(c/a_3)^h]$, where $a_1$, $a_2$, $a_3$ and $h$ are sigmoid parameters, and c represents said different concentrations, and wherein $a_3$ represents the toxicity of the agent.

According to some embodiments of the invention, $a_1$ and $a_2$ are predetermined and wherein said fitting comprises applying a two-parameter fit to provide a value for said $a_3$ and said h.

According to some embodiments of the invention, $a_1=0$.

According to some embodiments of the invention, $a_2=1$.

According to some embodiments of the invention, the toxicity is $TC_{50}$.

According to some embodiments of the invention, incubating said organoids is executed in a multi-well plate.

Analysis and Discussion

In this work the present inventors have established a robust microphysiological analysis platform with streamlined real time analysis of tissue viability. The tissue embedded sensors permit unparalleled measurements at a rate ranging from 1 per 25 seconds to a rate of one per one hour for a period of 3-4 days without medium change, allowing to discover rapid changes in cellular viability. Non-alcoholic fatty liver disease is a growing epidemic affecting over 25% of the global population. Driven by life style choices and prescription drug use, the disease can range from steatosis to steatohepatitis, cirrhosis, and hepatocellular carcinoma. Interestingly, in spite of fundamental differences between human and rodent in the regulation of lipid metabolism, rodents are still predominantly being used to study the disease. Importantly, while in human metabolism glucose serves as the predominant precursor for lipogenesis, rodents utilize acetic acid in de novo lipogenesis, circumventing mitochondrial pathways. In fact, most drug candidates identified in rodent models of fatty liver injury have not proven effective in clinical studies. This suggests the development of a robust microphysiological model of human fatty liver disease could prove useful in drug development and safety assessment.

In current understanding, Valproate-induced steatosis is caused by β-oxidation impairment, due to the formation of valproyl-CoA conjugate in the mouse liver. Interestingly, valproyl-CoA is virtually undetectable in Valproate treated patients serum or urine sample and in a sub-toxic concentration its formation should be negligible. However, in mouse models exposed to high doses of Valproate, valproyl-CoA leads to mitochondrial CoA depletion, coupled with CPT1 inhibition, blocks β-oxidation and impairs ATP production. In rat hepatocytes, toxic concentration of valproate induces mitochondrial swelling, increase ROS production and led to cytochrome C release, suggesting direct mitochondrial damage and apoptosis. These findings, however, do no correlate to development of Valproate-induced liver injury in the clinical settings. Valproate induces only a mild elevation of liver enzymes in patients suggesting minimal cellular damage, developing damage only month to years following initial exposure.

Thus, this study demonstrates the real-time measurement of oxygen in a liver organoid.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

It is understood that any Sequence Identification Number (SEQ ID NO) disclosed in the instant application can refer to either a DNA sequence or a RNA sequence, depending on the context where that SEQ ID NO is mentioned, even if that SEQ ID NO is expressed only in a DNA sequence format or a RNA sequence format. For example, a sequence expressed in a DNA sequence format (e.g., reciting T for thymine) can refer to either a DNA sequence or the RNA sequence of an RNA molecule nucleic acid sequence. Similarly, though some sequences are expressed in a RNA sequence format (e.g., reciting U for uracil), depending on the actual type of molecule being described, it can refer to either the sequence of a RNA molecule comprising a dsRNA, or the sequence of a DNA molecule that corresponds to the RNA sequence shown. In any event, both DNA and RNA molecules having the sequences disclosed with any substitutes are envisioned.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839, 153; 3,850,752; 3,850,578; 3,853,987; 3,867,517; 3,879, 262; 3,901,654; 3,935,074; 3,984,533; 3,996,345; 4,034, 074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, CA (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Robust High Content Formation of Organoids and Spheroids (Microtissues) in Multi Well Plates Formation of micro-tissues (microtissues) in multi well plates was carried out using the BioMek i5 automated liquid handling workstation.

A polystyrene non-treated 384 well plate manufactured by Greiner Bio-One (Austria) was used in the experiments due to its surface having a contact angle $\theta > 80°$. Plate's dimensions were programmed into an automated liquid handler with at least 0.1-100 µl working volume range (e.g. Biomek i5 Automated Workstation, Beckman Coulter, CA, USA) using tips with an opening of 10 to 900 µm in diameter.

Cells were suspended in polymer mixtures, composed of either natural polymers such as Collagen I or Matrigel, or synthetic polymers such as polylactic acids (PLA) at a density of $1 \times 10^5$ to $1 \times 10^9$ cells/mL in a 1:3 to 1000:1 polyer:medium (v/v) ratio to create suitable microenvironment for the micro-tissues. For example, four parts Matrigel to one-part glioblastoma cell suspension was used to create tumor organoids. Then, the mixture was mixed with 0.5-4 mg of tissue-embedded sensors for each 1 mL of cell/matrix mixture (e.g. 2 mg of CPOx beads Ø50 µm, sensor dye Ru-Phenanthrolin (orange), in 1 mL of patient-derived glioblastoma/Matrigel® mixture).

In order to create geometrically even microtissues, the automated liquid handler dispenses 0.2 to 5 µl of mixture at the center of the well, 0.4 to 5 mm above the surface of the well at a rate of 1 to 100 µl/s, then moves to $$\left(2 * \sqrt[3]{\frac{3V}{4\pi}} - 0.18\right) \text{mm}$$

above the bottom of the well for a drop touch, where V is the volume of the droplet in microliter. The above equation calculates the height to which the tip head moves to above the surface of the well as measured in millimeters (mm).

For example, 1.1 µl of cell mixture is dispensed 3 mm above the bottom of the well at a rate of 100 µl/s to create a hanging droplet 1.28 mm in diameter. The pipette tip then moves to 1.10 mm above the surface of the well to carefully place the droplet on the plastic.

The height of the pipette tip can be adapted to create geometrically uneven microtissues. For example, ring-like microtissue can be generated by dispensing 1.1 µl of mixture at center of the well, 0.05 mm above the bottom of the well causing the gel to spread in a doughnut pattern around the tip.

After 10-60 minutes of polymerization (or gelation) in 37° C. the culture medium is added. Time varies based on humidification, matrix type and Matrix:Medium (v/v) ratio (e.g. 4:1 Matrix:Medium of Matrigel® for patient-derived glioblastoma microtissue is given 30 minutes of gelatation in a humidified 37° C.). The organoids are left to form and stabilize for 8-168 hours (e.g., patient-derived glioblastoma microtissues are left 48 hours to form and stabilize). This process creates organoids with <10% variability.

TABLE 4

Various multi-well plates and contact angles for organoid formation

| Product Name | Company | Product # | Contact Angle | Organoid Formation |
|---|---|---|---|---|
| Microplate 384w, Polystyrene, Clear, Sterile | Greiner Bio-One | 60-781186 | 84.1° | +++ |
| Microplate 384w, Polystyrene, TC-treated, Clear, Sterile | Greiner Bio-One | 60-781182 | 47.8° | – |

TABLE 4-continued

| Various multi-well plates and contact angles for organoid formation | | | | |
| --- | --- | --- | --- | --- |
| Product Name | Company | Product # | Contact Angle | Organoid Formation |
| Corning ® 384-well Clear Polystyrene Corning Microplates, Standard, Non treated | | 3680 | 78.3° | + |
| Corning ® 384-well Clear Polystyrene Corning Microplates, Standard, TC-treated | | 3701 | 56.2° | – |
| No. 1 square cover glass | Corning | 2845-18 | 75.5° | + |

Example 2

A Method to Drug-Screen Tumors in 3D Spheroids Using 384 Well Plate Format

Currently, most in vitro drug screening studies are still performed under conventional two-dimensional (2D) cell culture systems, which are often far from the physiological environment of the tumor. Such drug screenings methods may therefore not produce accurate or realistic readouts. Although in vivo experiments are mimicking the real tumor physiological environment, it is time consuming and very expensive to use for high-throughput drug screening, besides that in in vivo experiments it is hard to use for patient-specific tumor response in high-throughput assays. Thus, 3D in vitro models of human tumors are needed to emulate the tumor physiology and can be used for personalized drug screening assays.

Here the present inventors provide a novel way to monitor and measure in a real-time resolution the anti-proliferative effect of drugs and anti-cancer agents on patient-derived tumor cells and tumor models cultured in physiological environment using automated 384-well plate assays. The chemotherapeutic drug candidates include, without limitation, NIH plate assays of FDA-approved anti-cancer drugs, kinase inhibitors, and other small molecule drugs.

As mentioned in the background section above, the present inventors focus herein on glioblastoma, but the screening platform is readily extendible to other types of cancer that can be similarly modeled.

Cell Culture

In general, cells were kept under standard conditions in a humidified incubator at 37° C., under 5% $CO_2$. U87-MG cells (obtained from the American Type Culture Collection (ATCC)) were cultured in Eagle's Minimum Essential Medium (EMEM) (ATCC® 30-2003™) supplemented with 15% (volume/volume) fetal bovine serum (FCS), 100 U/mL penicillin, and 100 µg/mL streptomycin (Sigma-Aldrich). Medium was changed every 2 days and cells were split every 5 days. Patient's specific glioblastoma derived cells (obtained from Cleveland clinic) were cultured in Neurobasal™ Medium (Trademark Serial number: 77137832) minus phenol red (Thermo-Fischer Scientific) supplemented with 1× (volume/volume) B27 minus Vitamin A (Thermo-Fischer Scientific), 10 ng/ml basic fibroblast growth factor (bFGF) 10 ng/ml EGF (epidermal growth factor) (PEPROTECH), 100 U/mL penicillin, 100 µg/mL streptomycin (Sigma-Aldrich) and L-Alanyl-L-Glutamine (Biological Industries). Medium was changed every 3 days and cells were split every 2-3 weeks. Rat retinal capillary endothelial cells (RCECs) were cultured in EGM™-2 Endothelial Cell Growth Medium-2 BulletKit™ (Lonza). Medium was changed every 3 days and cells were split every 6 days.

Tumor Organoid Formation

For tumor organoid formation, cancer cells were cultured to reach the adequate number needed for a 384 well plate. Cells were trypsinized, counted, and centrifuged at 300 g for 5 minutes at 4° C. The pellet was then mixed with 5 mg CPOx-50-RuP oxygen-sensing beads (Colibri Photonics) and resuspended in 800 µl of ice-cold solution of collagen type I (BD Biosciences) or Matrigel® Basement Membrane Matrix, Growth Factor Reduced (GFR) (Corning) for a final seeding density of 25-50×10^6 cells/mL. In some cases, endothelial cells (RCECs) are used in the assembly of the tumor spheroids by mixing them with same or double the number of tumor cells (i.e. 1:1 or 1:2 ratios) before centrifugation. The 800 µl mix was then equally distributed into a PCR strip (100 µl/tube) and passed to a Biomek i5 liquid handling workstation (Beckman Coulter) for the formation of uniformly-sized organoid in 384-well plate. The plate was then incubated for 30 minutes at 37° C., and the medium was replaced using the liquid handing workstation. Medium was changed every two days for 4 days before adding the drugs (5 µM of NIH chemotherapeutic drugs in triplicates per drug).

Measurements

On the day of measurement, medium was changed 2-12 hours before drug induction, based on the oxygen consumption of the microtissue (e.g., U87-MG spheroids are given 6 hours after media change before drugs are induced).

After applying the drugs, the plate was placed on the DynamiX bioanalyzer (Tissue Dynamics). Organoids positions were detected optically. Oxygen content was monitored at a predetermined rate of 1 to 10 seconds of measurement at each location (e.g. Matrigel®/U87-MG spheroids treated with a set of FDA-approved anticancer drugs to enable cancer research was measured via phosphorescence for 4 seconds/well). Each cycle takes between 10-120 minutes, dependent on sampling rate and well number (e.g., Matrigel®/U87-MG spheroids 384 well at a sampling rate of 4 measurements/well take about 60 minutes for each cycle). After 24-168 hours the experiment is stopped, and end point measurements are taken: supernatant is collected automatically for further metabolic analysis; further endpoint analysis on the tissue, including RNA extraction, florescent e.g., Live/Dead, AOP) or immunofluorescent assays.

For Primary Assays (Single Dose, Multiple Treatments)

The $O_2$ measurements data were analyzed, and hits were assigned to drugs that showed >20% decrease in oxygen consumption in most technical repeats, compared to controls. Further validation was usually done by multiple independent repeats (e.g. Matrigel®/U87-MG spheroids treated with a set of FDA-approved anticancer drugs to enable cancer research [AOD IX] were assessed in 3 independent experiments).

False positive hits (hits that were only found in 1 experiment) were ignored.

Example 3

Method of Identifying Time to Onset and Lower Exposure Limit (LEL) of a Drug Cell Culture All cells were cultured under standard conditions in a humidified incubator at 37° C., under 5% $CO_2$. $E6/E7^{LOW}$ human hepatocyte were expanded and differentiated as previously described (G. Levy, et al., 2015. Nature Biotechnology, 33: 1264-1271). Differentiation and maintenance medium is composed of William's E basal medium supplemented with dexamethasone (Sigma-Aldrich, USA), Bovine serum albumin (Fraction V, MP, USA), Insulin, transferrin and selenium (ITS, Gibco, USA), L-Alanyl-L-Glutamine (BI, Israel), 100 U $ml^{-1}$ penicillin, and 100 μg $ml^{-1}$ streptomycin (BI, Israel).

HepG2/C3A cells were obtained from the American Type Culture Collection (ATCC, USA). Cells were cultured in Dulbecco's Modified Eagle Medium basal medium (DMEM) supplemented with fetal bovine serum (BI, Israel), Eagle-MEM non-essential amino acids (BI, Israel), L-Alanyl-L-Glutamine (BI, Israel) or L-Glutamine (BI, Israel), 100 U $ml^{-1}$ penicillin, and 100 μg $ml^{-1}$ streptomycin (BI, Israel).

Microvascular cardiac endothelial cells (VEC Technologies, USA) were cultured in PeproGrow™ MicroV (Microvascular Endothelial Cell Media, Peprotech, USA) supplemented with 10% fetal bovine serum, 100 U $ml^{-1}$ penicillin, and 100 μg $ml^{-1}$ streptomycin (BI, Israel).

Organoid Seeding

A suspension of HepG2/C3A cells and CPOx-50-RuP beads (Colibri Photonics, Germany) were suspended in 2.5 mg/ml rat tail collagen type I (Corning, USA) at a cell density of $7\times10^5$ cells/μl. A volume of 1.1 μl of the gel-imbedded mixture was injected into each microwell and left to form spontaneously until their metabolic activity stabilized around day 4.

$E6/E7^{LOW}$ human hepatocyte and microvascular endothelial cells counted and mixed in a 1:1 ratio in 2.5 mg/ml rat tail collagen type I (Corning, USA) at a cell density of $4.6\times10^5$ cells/μl. Organoids were seeded in a similar manner as mentioned above.

$E6/E7^{LOW}$ Human Hepatocyte Viability Assessment $E6/E7^{LOW}$ human hepatocyte were cultured with different concentrations of compounds dissolved in culture medium for 24 hours. Cell viability was subsequently determined using LIVE/DEAD Cytotoxicity kit (Molecular Probes, USA) according to manufacturer directions. Briefly, cultures were incubated for 30 minutes with 2 μM calcein AM and 3 μM ethidium homodimer-1. Live cells were positive for green fluorescence due to hydrolysis of the acetoxymethyl ester group by intracellular esterases. Dead cells were positive for red fluorescence due to ethidium homodimer-1 binding intracellular DNA, possible in intact membranes. Cellular viability was expressed as live over dead ratio and normalized based on negative (DMSO/DDW/EtOH) and positive (0.1% Saponin) controls. Fluorescence micrographs were analyzed for total fluorescence using ImageJ for 12 repeats for each sample. $TC_{50}$ and $TC_{20}$ concentrations were calculated using MATLAB® Curve Fitting Tool. Results were fitted to a sigmoidal curve (Prentice, 1976; Wenner et al., 2011). Error bars indicate ±SE.

Adverse Outcome Pathway Analysis

Quantification of Apoptotic index was performed using DeadEnd™ fluorometric TUNEL System (Promega) according to manufacturer directions. Briefly, cells were treated with $TC_{20}$ concentrations of compounds dissolved in culture medium for 24 hours, and subsequently fixed in 4% Paraformaldehyde (PFA). Cells were then permeabilized and exposed to fluorescein-12-dUTP and terminal deoxynucleotidyl transferase (TdT). The reaction was subsequently stopped and the cells counterstained with 1 μg/mL Hoechst 33258. Apoptotic cells were positive for green fluorescence in the nucleus. Percentage apoptosis was defined as the number of TUNEL positive nuclei normalized to Hoechst 33258 positive nuclei. Quantification of Steatosis was performed using HCS LipidTOX™ Phospholipidosis and Steatosis Detection Kit (ThermoFisher). Briefly, differentiated cells were incubated with different concentrations of compounds dissolved in culture medium and 1× Phospholipidosis Detection Reagent for 48 hours, subsequently fixed in 4% PFA. Cells were then stained with 1× LipidTOX™ for 20 minutes and counterstained with 1 μg/mL Hoechst 33258. Staining intensity was normalized to number of Hoechst 33258 positive nuclei. Quantification of Bile Secretion was performed using 5(6)-carboxy-2',7'-dichlorofluorescein diacetate (CDFDA) staining. Briefly, differentiated cells were incubated with different concentrations of compounds dissolved in culture medium for 24 hours. Cells were then treated with 10 μg/mL CDFDA and 1 μg/mL Hoechst 33342 for 30 minutes. Incubation medium was removed and cultures washed with ice-cold PBS containing calcium and magnesium. Staining intensity was normalized to number of Hoechst 33342 positive nuclei. Analysis excluded Intracellular CDFDA staining based on intensity and phase images. All quantifications were made in comparison to cells treated with melatonin as negative control.

Multiple Concentration Assays

For secondary assays (multiple doses of selected treatments), a series of serial dilutions of 1:10 to 3:4 from various drugs were automatically prepared, then tissues were then exposed in multiple biological repeats to a wide range concentrations of several drugs within a single experiment. For example, Matrigel®/U87-MG spheroids treated with a set of 8 FDA-approved anticancer drugs [AOD IX] were examined in a single experiment over a range of 12 concentrations, in a series of 1:2 dilution for each drug. Each condition was tested with 4 biological replicates. The $O_2$ measurements data were analyzed, and $TC_{50}$, Time-To-Onset (TTO) and lower exposure level (LEL) were calculated from the dose-dependent kinetic respiratory behavior in response to each drug.

Toxicity of Hits on Other Human Tissue Models

In parallel, the present inventors have conducted a secondary assay on other human microtissues for checking toxicity and toxicity-related parameters ($TC_{50}$, TTO, and LEL) on these human physiological models.

These microtissues include human micro-livers generated from human induced pluripotent stem cells (hu-iPS) or human hepatocytes derived liver microtissue, hu-iPS derived heart microtissue, human kidney derived kidney microtissue, and hu-iPS derived brain microtissue.

Real-Time Oxygen Measurement

Real-time oxygen measurements were performed optically using tissue embedded lifetime-based luminescence quenching (LBLQ) (oxygen sensor) (Schmalzlin E., et al., 2005. Biophysical journal, 89: 1339-1345; Papkovsky, D. B. et al., 2004. Methods in enzymology, 381, 715-735; Ast, C., et al., 2012, 12: 7015-7032).

Fifty-micrometer-diameter polystyrene microbeads were loaded with ruthenium-phenanthroline-based phosphorescence dye (CPOx-50-RuP). RuP phosphorescence signal shows a characteristic delay given by the lifetime of its excited triplet state. Oxygen acts as a quencher, leading to a decrease in decay time and signal intensity with increasing concentration. The present inventors chose to measure decay time, rather than signal intensity, as it is not sensitive to changes in probe concentration or excitation intensity over the course of the experiment. The signal was measured using the OPAL system (Colibri Photonics, Germany) that comprises of a control module, 532 nm LED excitation source, and a photomultiplier (PMT) detector mounted on the ocular of an IX81 Olympus microscope (Olympus, Japan). A filter cube with 531/40 (Ex), 555, 607/70 (Em) was inserted in the optical light path during measurements. To accurately measure decay time, the present inventors chose phase modulation in which sinusoidal amplitude-modulated light is shifted in phase due to oxygen quenching. To overcome the superposition of in-phase background fluorescence that alters the phase of the detected signal, the present inventors used a novel 53.5 and 31.3 kHz two-frequency phase modulation that allowed to screen out the interference [Schmalzlin E., et al., 2005. Biophysical journal, 89: 1339-1345; Papkovsky, D. B. et al., 2004. Methods in enzymology, 381, 715-735; Ast, C., et al., 2012. Sensors (Basel), 12: 7015-7032; Engelhard, S., et al., 2006. Analytical and bioanalytical chemistry, 384: 1107-1112; Prill, D. et al., 2016, Archives of toxicology, 90: 1181-1191]. Measurements were carried out by averaging five consecutive 4-s exposures. Measurements were taken every 15 minutes. Under similar conditions, 28 days of measurement of organoids was done with no apparent phototoxicity, signal drift, or relevant loss of signal intensity (Schmalzlin E., et al., 2005. Biophysical journal, 89: 1339-1345).

Assessment of Cellular Toxicity and Time to Onset

Organoids were exposed to different concentrations of compounds dissolved in culture medium. Cell viability was determined by oxygen uptake following 24 hours of exposure unless otherwise noted. $TC_{50}$ concentrations were determined using MATLAB by sigmoidal curve fitting (Wenner, M. M. et al., 2011, J Appl Physiol (1985), 111: 1703-1709; Prentice, R. L. et al., 1976, Biometrics, 32: 761-768). Time to onset was analyzed by MATLAB based on LPF and trend assessment.

Assessment of a Lowest Exposure Level

To find the asymptotic concentration for which damage occurs only at infinite exposure time, the present inventors used a previously developed model for accumulative drug exposure (El-Kareh et al., 2000. Neoplasia, 2: 325-338; Currie, G. M. 2018. J Nucl Med Technol, DOI: 10.2967/jnmt.117.199588). The model is based on the steady-state dynamics of flux accumulation, using a linear first-order approximation of the cell membrane. The flux behavior is described by $$J(C) = \left(J_{min} / 1 - e^{\frac{t}{\tau}}\right)$$

where J(C) is the concentration dependent flux, $J_{min}$ is the minimal flux that will cause an effect, t is time of exposure and $\tau$ is a drug-cell specific constant accounting reaction dynamics (Gowrishankar et al., 2003. Proceedings of the National Academy of Sciences of the United States of America, 100: 3203-3208; Kotnik T. et al., 2000. IEEE Trans Biomed Eng, 47: 1074-1081). In the present case, t is the Time to Onset (TTO) of damage creating a bi-asymptotic behavior. This adapted model is used to describe lowest exposure level (LEL) under first order, steady state assumptions, as $$TTO^* = TTO_{measured} - t_{const}$$

$$[C_{drug}] = \left(LEL / 1 - e^{\frac{TTO^*}{\tau}}\right)$$

Statistical Analysis

Experiments were repeated 2 or 3 times with triplicate samples for each experimental condition, unless stated otherwise. Data from representative experiments are presented, and similar trends were seen in multiple trials. A parametric two-tailed Student's t-test was used for calculating significant differences between groups. All error bars represent ±standard error, unless otherwise noted. $TC_{50}$ and LEL error indicate the standard error calculated based on the 95% confidence bound calculated by the curve-fitting tool.

Example 4

Microphysiological Platform Unravels the Dynamics of Drug Induced Steatosis

Materials and Experimental Methods

Cell Culture

All cells were cultured under standard conditions in a humidified incubator at 37° C., under 5% $CO_2$. E6/E7$^{LOW}$ human hepatocyte were expanded and differentiated as previously described (Levy et al., 2015). Differentiation and maintenance medium is composed of William's E basal medium supplemented with dexamethasone (Sigma-Aldrich, USA), Bovine serum albumin (Fraction V, MP, USA), Insulin, transferrin and selenium (ITS, Gibco, USA), L-Alanyl-L-Glutamine (Biological Industries, Israel), 100 U ml$^{-1}$ penicillin, and 100 μg ml$^{-1}$ streptomycin (Biological Industries, Israel).

HepG2/C3A cells were obtained from the American Type Culture Collection (ATCC, USA). Cells were cultured in Dulbecco's Modified Eagle Medium basal medium (DMEM) supplemented with fetal bovine serum (Biological Industries, Israel), Eagle-MEM non-essential amino acids (Biological Industries, Israel), L-Alanyl-L-Glutamine (BI, Israel) or L-Glutamine (Biological Industries, Israel), 100 U ml$^{-1}$ penicillin, and 100 μg ml$^{-1}$ streptomycin (Biological Industries, Israel).

Microvascular cardiac endothelial cells (VEC Technologies, USA) were cultured in PeproGrow™ MicroV (Microvascular Endothelial Cell Media, Peprotech, USA) supplemented with 10% fetal bovine serum, 100 U ml$^{-1}$ penicillin, and 100 μg ml$^{-1}$ streptomycin (Biological Industries, Israel).

Organoid Seeding

A suspension of HepG2/C3A cells and CPOx-50-RuP beads (Colibri Photonics, Germany) were suspended in 2.5 mg/ml rat tail collagen type I (Corning, USA) at a cell density of 7×10$^5$ cells/μl. A volume of 1.1 μl of the gel-imbedded mixture was injected into each microwell and left to form spontaneously until their metabolic activity stabilized around day 4.

E6/E7$^{LOW}$ human hepatocyte and microvascular endothelial cells counted and mixed in a 1:1 ratio in 2.5 mg/ml rat tail collagen type I (Corning, USA) at a cell density of 4.6×10$^5$ cells/μl. Organoids were seeded in a similar manner as mentioned above.

E6/E7$^{LOW}$ Human Hepatocyte Viability Assessment

E6/E7$^{LOW}$ human hepatocyte were cultured with different concentrations of compounds dissolved in culture medium for 24 hours. Cell viability was subsequently determined using LIVE/DEAD Cytotoxicity kit (Molecular Probes, USA) according to manufacturer directions. Briefly, cultures were incubated for 30 minutes with 2 μM calcein AM and 3 μM ethidium homodimer-1. Live cells were positive for green fluorescence due to hydrolysis of the acetoxymethyl ester group by intracellular esterases. Dead cells were positive for red fluorescence due to ethidium homodimer-1 binding intracellular DNA, possible in intact membranes. Cellular viability was expressed as live over dead ratio and normalized based on negative (DMSO/DDW/EtOH) and positive (0.1% Saponin) controls. Fluorescence micrographs were analyzed for total fluorescence using ImageJ for 12 repeats for each sample. $TC_{50}$ and $TC_{20}$ concentrations were calculated using MATLAB® Curve Fitting Tool. Results were fitted to a sigmoidal curve (Prentice, 1976; Wenner et al., 2011). Error bars indicate ±SE.

Adverse Outcome Pathway Analysis

Quantification of Apoptotic index was performed using DeadEnd™ fluorometric TUNEL System (Promega) according to manufacturer directions. Briefly, cells were treated with $TC_{20}$ concentrations of compounds dissolved in culture medium for 24 hours, and subsequently fixed in 4% Paraformaldehyde (PFA). Cell were then permeabilized and exposed to fluorescein-12-dUTP and terminal deoxynucleotidyl transferase (TdT). The reaction was subsequently stopped and the cells counterstained with 1 μg/mL Hoechst 33258. Apoptotic cells were positive for green fluorescence in the nucleus. Percentage apoptosis was defined as the number of TUNEL positive nuclei normalized to Hoechst 33258 positive nuclei. Quantification of Steatosis was performed using HCS LipidTOX™ Phospholipidosis and Steatosis Detection Kit (ThermoFisher). Briefly, differentiated cells were incubated with different concentrations of compounds dissolved in culture medium and 1× Phospholipidosis Detection Reagent for 48 hours, subsequently fixed in 4% PFA. Cells were then stained with 1× LipidTOX™ for 20 minutes and counterstained with 1 μg/mL Hoechst 33258. Staining intensity was normalized to number of Hoechst 33258 positive nuclei. Quantification of Bile Secretion was performed using 5(6)-carboxy-2',7'-dichlorofluorescein diacetate (CDFDA) staining. Briefly, differentiated cells were incubated with different concentrations of compounds dissolved in culture medium for 24 hours. Cells were then treated with 10 μg/mL CDFDA and 1 μg/mL Hoechst 33342 for 30 minutes. Incubation medium was removed, and cultures washed with ice-cold PBS containing calcium and magnesium. Staining intensity was normalized to number of Hoechst 33342 positive nuclei. Analysis excluded intracellular CDFDA staining based on intensity and phase images. All quantifications were made in comparison to cells treated with melatonin as negative control.

Real-Time Oxygen Measurement

Real-time oxygen measurements were performed optically using on-chip lifetime-based luminescence quenching (LBLQ). Fifty-micrometer-diameter polystyrene microbeads were loaded with ruthenium-phenanthroline-based phosphorescence dye (CPOx-50-RuP). RuP phosphorescence signal shows a characteristic delay given by the lifetime of its excited triplet state (data not shown). Oxygen acts as a quencher, leading to a decrease in decay time and signal intensity with increasing concentration. The present inventors chose to measure decay time, rather than signal intensity, as it is not sensitive to changes in probe concentration or excitation intensity over the course of the experiment. The signal was measured using the OPAL system (Colibri Photonics, Germany) that comprises of a control module, 532 nm LED excitation source, and a photomultiplier (PMT) detector mounted on the ocular of an IX81

Olympus microscope (Olympus, Japan). A filter cube with 531/40 (Ex), 555, 607/70 (Em) was inserted in the optical light path during measurements (data not shown). To accurately measure decay time, the present inventors chose phase modulation in which sinusoidal amplitude-modulated light is shifted in phase due to oxygen quenching (data not shown). To overcome the superposition of in-phase background fluorescence that alters the phase of the detected signal, the present inventors used a novel 53.5 and 31.3 kHz two-frequency phase modulation that allowed to screen out the interference. Measurements were carried out by averaging five consecutive 4-seconds exposures. Measurements were taken every 15 minutes. Under similar conditions, 28 days of measurement of organoids was done with no apparent phototoxicity, signal drift, or relevant loss of signal intensity.

Assessment of Cellular Toxicity and Time to Onset

Bioreactors were perfused with different concentrations of compounds dissolved in culture medium. Cell viability was determined by oxygen uptake following 24 hours of exposure unless otherwise noted. $TC_{50}$ concentrations were determined using MATLAB by sigmoidal curve fitting. Time to onset was analyzed by MATLAB based on LPF and trend assessment.

Assessment of a Lowest Exposure Level

To find the asymptotic concentration for which damage occurs only at infinite exposure time, the present inventors used a previously developed model for accumulative drug exposure. The model is based on the steady-state dynamics of flux accumulation, using a linear first-order approximation of the cell membrane. The flux behavior is described by $$J(C) = \left( J_{min} / 1 - e^{\frac{t}{\tau}} \right)$$

where J(C) is the concentration dependent flux, $J_{min}$ is the minimal flux that will cause an effect, t is time of exposure and τ is a drug-cell specific constant accounting reaction dynamic. In this case, t is the Time to Onset (TTO) of damage creating a bi-asymptotic behavior. This adapted model is used to describe lowest exposure level (LEL) under first order, steady state assumptions, as $$[C_{drug}] = \left( LEL / 1 - e^{\frac{TTO^*}{\tau}} \right)$$

where TTO* is obtained by subtracting a parameter $t_{const}$ from the measured value $TTO_{measured}$ of the time to onset:

$$TTO^* = TTO_{measured} - t_{const}.$$

The value of $t_{const}$ is basically a vertical asymptote of the function $LEL/(1-e^{TTO^*/\tau})$. In practice, $t_{const}$ can obtained by fitting the dependence of the concentration on $TTO_{measured}$ to the function concentration $= a//(1-e^{(TTO-b)/c})$ where a is the lowest exposure level, and c is the value of $t_{const}$.

Statistical Analysis

Experiments were repeated 2 or 3 times with triplicate samples for each experimental condition, unless stated otherwise. Data from representative experiments are presented, and similar trends were seen in multiple trials. A parametric two-tailed Student's t-test was used for calculating significant differences between groups. All error bars represent ±standard error, unless otherwise noted. TC50 and LEL error indicate the standard error calculated based on the 95% confidence bound calculated by the curve-fitting tool.

Experimental Results

Valproate and Stavudine Induced Steatosis

The broad-spectrum antiepileptic drug Valproate and anti-retroviral drugs such as Stavudine (d4T) are known to induce hepatic steatosis in patients and animal models. The present inventors have therefore assessed their effect on differentiated, polarized cultures of E6/E7$^{LOW}$ human hepatocytes (Data not shown). Recently published E6/E7$^{LOW}$ hepatocytes show equivalent toxicity profile to primary human hepatocytes (Levy et al., 2015), but less batch-to-batch variability (FIG. 14B). Analysis of Valproate and Stavudine toxicity showed TC$_{50}$ of 2.5±0.4 and 0.8±0.06 mM (Data not shown), 5-times and 100-times higher than reported C$_{max}$, respectively. Adverse outcome analysis showed no evidence of apoptosis following 24 hours exposure (Data not shown), and only mild inhibition of bile secretion for Stavudine (p<0.05, n=4). However, both compounds show strong and significant increase in neutral lipids (p<0.001, n=4). Evidence of phospholipidosis was seen following Valproate but not Stavudine exposure.

Figures 13D, 13E, 13F:
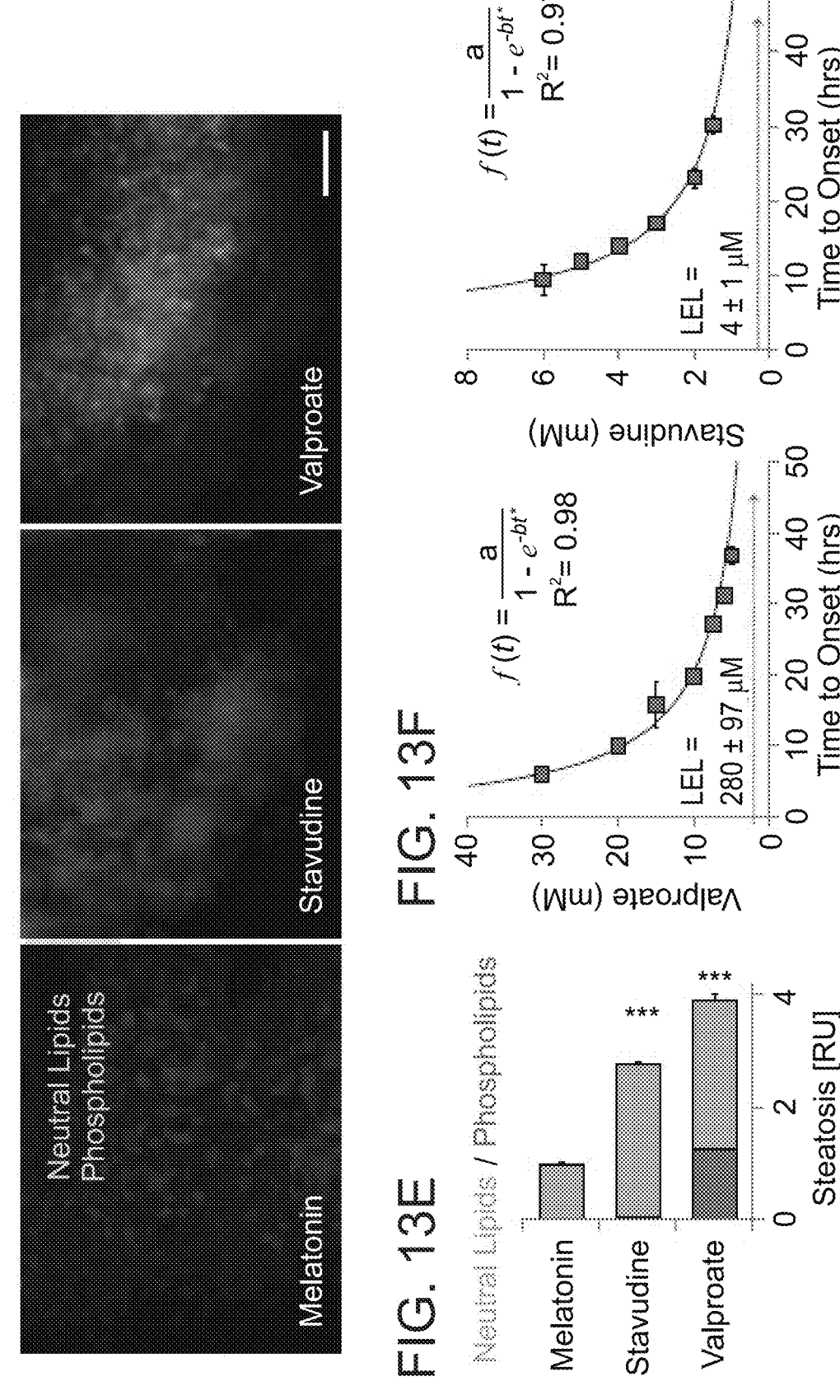

Real Time Analysis of Respiratory Dynamics Suggests Slow Accumulative Damage Induced by Valproate and Stavudine The present inventors have recently shown that time resolved information can offer insight into mechanism of action as direct damage (e.g. rotenone) occurs in minutes while indirect accumulative damage progresses over hours (e.g. amiodarone) (Bavli et al., 2016; Prill et al., 2016). To study the respiratory dynamics of Valproate and Stavudine the present inventors exposed differentiated HepG2/C3A organoids on chip to the drugs tracking effects for 46 hours (FIG. 13A). Both drugs showed progressive accumulation of damage, reaching TC$_{50}$ of 14±2 mM for Valproate and 1.7±0.4 mM for Stavudine at 42 hours (FIG. 13B). Differences in TC$_{50}$ between E6/E7$^{LOW}$ hepatocytes (data not shown) and HepG2/C3A cells suggest metabolic activation is required for toxicity. Time to onset of damage (TTO) was dose dependent, ranging from 6-36 hours for Valproate to 10-29 hours for Stavudine (FIG. 13C). These results suggest a clear secondary mechanism of damage, possibly due to excess lipid accumulation. To confirm drug-induced steatosis on the chip of some embodiments of the invention, the present inventors stained the cells for neutral lipids and phospholipids (FIG. 13D). HepG2/C3A organoids showed strong 4-fold and 3-fold increase (p<0.001, n=9) in the amount of intracellular lipids for Valproate and Stavudine, respectively (FIG. 13D-E).

Interestingly, this data describes a relationship between drug concentration and the time it takes for damage to develop upon chronic exposure. Thus, the present inventors can fit the behavior on a flux accumulation model and extract the asymptotic concentration for which damage would occur only at infinite exposure time (FIG. 13F). This analysis suggests that the lowest exposure levels (LEL) for Valproate and Stavudine are 280±97 and 4±1 µM, respectively. Alarmingly these calculated LEL levels fall within the observed C$_{max}$ in patients (Klotz and Antonin, 1977; Rezk et al., 2003; Sussman and McLain, 1979; Verweij-van Wissen et al., 2005) suggesting that the clinically observed steatosis for both drugs might be due to improper safety margins and should be revaluated.

Analysis and Discussion

Non-alcoholic fatty liver disease is a growing epidemic affecting over 25% of the global population (Bedogni et al., 2005; Browning et al., 2004; Lazo et al., 2013). Driven by lifestyle choices and prescription drug use, the disease can range from steatosis to steatohepatitis, cirrhosis, and hepatocellular carcinoma. Interestingly, in spite of fundamental differences between human and rodent in the regulation of lipid metabolism (Bergen and Mersmann, 2005; Chandrasekera and Pippin, 2014; Di Girolamo and Rudman, 1966; Eizirik et al., 1994), rodents are still predominantly being used to study the disease. Importantly, while in human metabolism glucose serves as the predominant precursor for lipogenesis, rodents utilize acetic acid in de novo lipogenesis, circumventing mitochondrial pathways. In fact, most drug candidates identified in rodent models of fatty liver injury have not proven effective in clinical studies (Cole et al., 2018; Hansen et al., 2017). This suggests the development of a robust microphysiological model of human fatty liver disease could prove useful in drug development and safety assessment.

Figure 15:
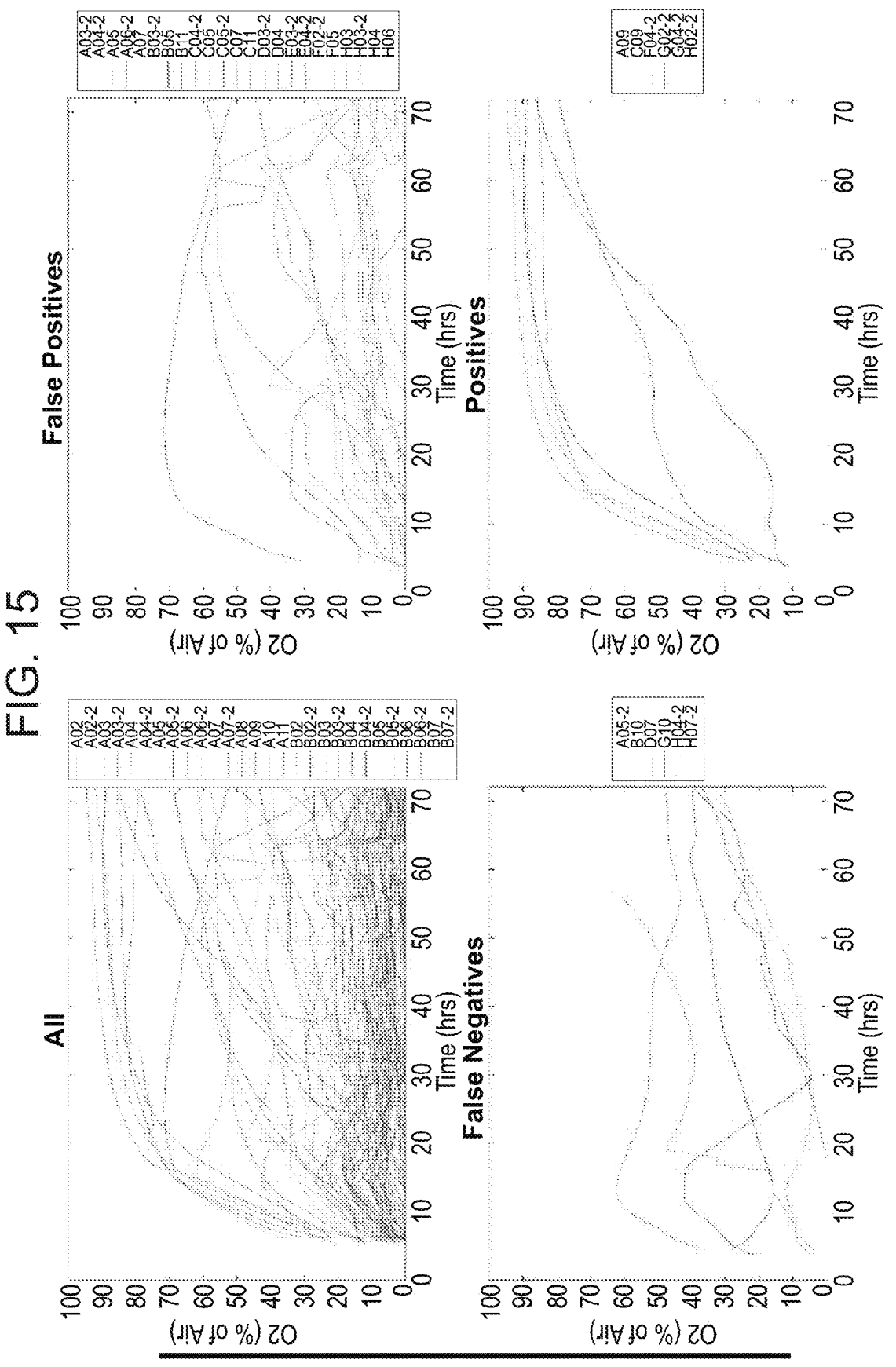
Figure 15:
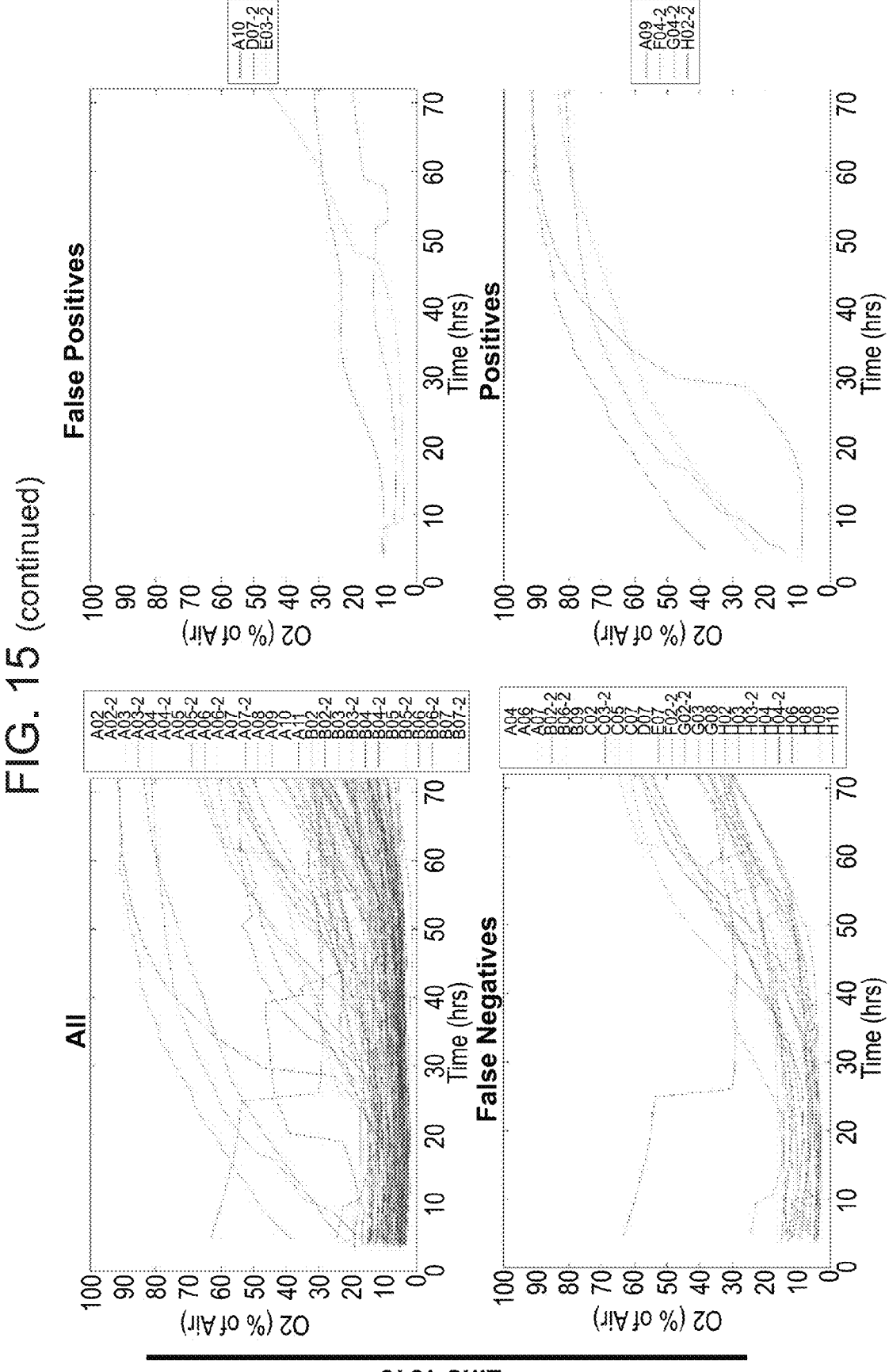
Figure 16A:
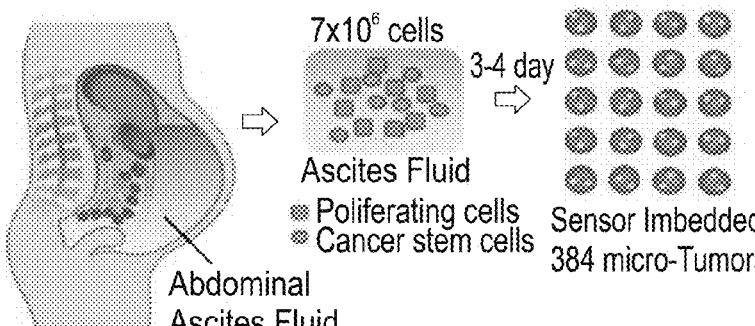
Figure 16B:
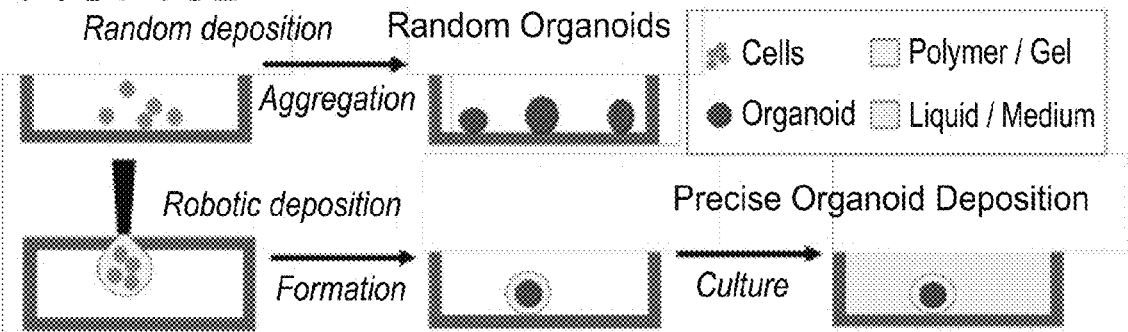
Figures 16C, 16D, 16E:
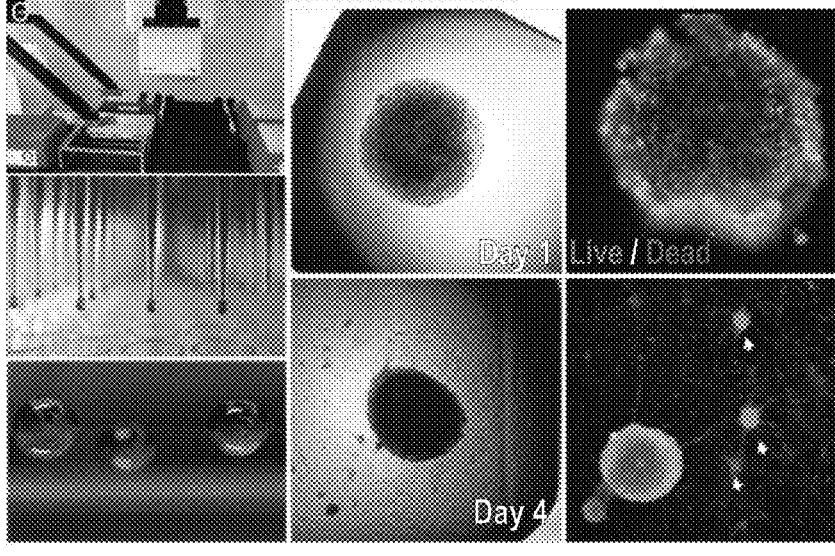

In current understanding, Valproate-induced steatosis is caused by β-oxidation impairment (Silva et al., 2008), due to the formation of valproyl-CoA conjugate in the mouse liver. Interestingly, valproyl-CoA is virtually undetectable in Valproate treated patients serum or urine sample (Ghodke-Puranik et al., 2013; McLaughlin et al., 2000) and in a sub-toxic concentration its formation should be negligible (Aires et al., 2007; Silva et al., 2008). However, in mouse models exposed to high doses of Valproate, valproyl-CoA leads to mitochondrial CoA depletion, coupled with CPT1 inhibition, blocks β-oxidation and impairs ATP production (Aires et al., 2010; Silva et al., 2001). In rat hepatocytes, toxic concentration of valproate induces mitochondrial swelling, increase ROS production and led to cytochrome C release, suggesting direct mitochondrial damage and apoptosis (Jafarian et al., 2013; Tong et al., 2005). These findings, however, do no correlate to development of Valproate-induced liver injury in the clinical settings, nor with the findings described herein (FIGS. 15-16A-J). Valproate induces only a mild elevation of liver enzymes in patients suggesting minimal cellular damage (Powell-Jackson et al., 1984), developing damage only month to years following initial exposure (Scheffner et al., 1988; Silva et al., 2008; Zimmerman and Ishak, 1982).

These findings demonstrate that sub-toxic levels of Valproate show no indication of direct mitochondrial damage in human hepatocytes (FIGS. 13A-F) and there was no evidence of apoptosis (FIG. 14D). Surprisingly, β-oxidation impairment does not appear to play a major role in Valproate induced steatosis in human hepatocytes (FIG. 16F), at least not in sub-toxic concentration. Importantly, recent studies exposing mice and rats to sub-toxic levels of Valproate similarly showed no indication of β-oxidation impairment confirming our findings (Punapart et al., 2014; Seckin et al., 1999). These results demonstrate that mechanism of acute toxicity differ from chronic exposure to sub-toxic concentrations of the drug, and that dynamic assessment of metabolic stress could accurately replicate clinically observed manifestations of damage in human patients.

Stavudine (d4T) related hepatotoxicity is suggested to occur by inhibition of DNA polymerase γ, the enzyme responsible for the replication of mitochondrial DNA (Akhtar et al., 2008; Sundar et al., 1997). Early studies showed that toxic concentration of Stavudine led to mitochondrial dysfunctional, ROS production, and apoptosis (Stankov et al., 2012). Recently, it has also been suggested that intracellular lipid accumulation may be the result of interactions with nuclear receptors and subsequent transcriptional changes (da Cunha et al., 2015; Svard et al., 2014; Viengchareun et al., 2007; Yang et al., 2010).

The findings of the present study show that sub-toxic levels of Stavudine show no indication of direct mitochondrial damage, with ATP production remaining relatively unchanged throughout the exposure (Data not shown). Analysis of the metabolic fluxes following Stavudine exposure suggests that sub-toxic concentrations cause a transient increase in lipogenesis followed by global suppression of both glycolysis and lipogenesis at sub-toxic concentrations (Data not shown). Indeed, gene expression analysis suggest that in this case, it does seem that transcriptional suppression of β-oxidation leads to lipid accumulation in human hepatocytes (Data not shown). This data fits recent findings regarding the ability of Stavudine to bind LXR and ER, suppressing PPAR-induced β-oxidation. Transcriptional modulation seems like a prominent lead to understand and prevent steatosis caused by sub-toxic exposure to Stavudine and other antiretroviral drugs.

In conclusion, the results presented herein demonstrate the real-time measurement of glucose, lactate, and oxygen in a liver-on-chip bioreactor perfused under physiological conditions. The platform is uniquely able to monitor metabolic changes indicating metabolic shifts and phenomena occurring at drug concentrations previously regarded as safe, revealing mechanisms relevant to the clinical manifestations of chronic exposure to drug-induced liver injury.

Example 5

Automated Drug Screening of Patient-Derived Micro-Tumors

The inability to effectively treat GBMs is due in part to their cellular heterogeneity, including a proposed population of self-renewing, tumor-propagating GBM stem cells (GSCs). Although the role of GSCs remains controversial due to unresolved issues with enrichment markers and cellular origin, many groups have shown that GSCs are crucial for tumor propagation and maintain tumor growth by promoting active angiogenesis, cancer invasion, and resistance to therapies including radiation. GSCs are not uniformly distributed throughout tumors but rather are enriched within two specific microenvironments: The perivascular niche and peri-necrotic hypoxic niche, which each provide distinct molecular regulation of their cellular states. GSCs are not passive recipients of environmental cues but possess the ability to remodel their own microenvironments. The microenvironment of a GSC can promote maintenance of stem cell state or even cause non-stem GBM cells to de-differentiate in response to pressures such as nutrient scarcity, pH, and hypoxia, suggesting the importance of these conditions in a model system. Recapitulating the diverse cellular microenvironment within tumors is therefore critical to accurately identify effective therapies.

Three-dimensional organoid culture systems mimic organ development by allowing growth and self-organization of large tissue structures containing microenvironments that can be remodeled and filled by diverse, interacting cell populations. Tumor organoids have yielded insights into niche factor requirements, recapitulate the cellular and genetic diversity of the parental tumors, and can model neoplastic progression and predict protein changes in human tissues. Tumor organoids reflect the natural heterogeneous environment of growing tumors needed to better model tumor stem cell behavior.

The present inventors have developed patient-derived GBM organoids, a controlled ex-vivo system that contains both proliferative and hypoxic niches, and gradients of stem and non-stem cells similar to those observed in patient tumors. GBM organoids self-organize and allow 3-dimensional cellular interactions, unveiling great cellular diversity and spatially defined cell phenotypes not seen in typical spheroid culture.

Experimental Results

Development of an Automated High Content Screening Assay on Glioblastoma Micro-Tumors Tumor xenograft and micro-slices preserve in-vivo architecture and immune components but are limited to handful of screened conditions (up to 10-20 compounds). As untargeted screens require hundreds of micro-tumors, the present inventors have developed a vascularized organoid model that self-assembles rapidly, mimicking physiological organization (Nahmias et al. 2006). Biopsies are routinely discarded but contains $5\text{-}10\times10^6$ tumor and immune cells (Tsai et al. 2018), capable forming between 250 to 500 micro-tumors allowing us to screen most known FDA-approve anti-cancer drugs against patient-specific micro-tumors. Cell pellets are resuspended and mixed with microvascular endothelial cells and 50 μm CPOx oxygen sensors in basement membrane gel (e.g. Matrigel). Cell suspension is then loaded on a HEPA-filtered BioMek 1-5 liquid handling workstation which will generate 384 well plates, placing one micro-tumor containing 50-75,000 cells in each well. Micro-tumors form into a solid organoids within 12-24 hours, forming a complex microvascular network and metabolically stabilizing within 72 to 96 hours (FIGS. 16A-E).

Figure 16F:
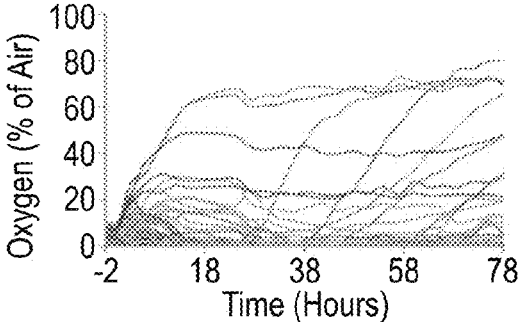

While current methods rely on end-point assays to assess drug efficacy missing late acting agents that affect tumors ability to expand, incorrectly detecting early acting drugs that permit recurrence. The tumor-embedded microsensors permit the kinetic assessment of tumor survival and growth, detecting these events in real time. Importantly, the present inventors have developed an automatic analytical method to derive a Lower Exposure Limit (LEL) which is the minimal concentration below which the patient will not see an effect and time to onset (TTO) for each potential drug from the kinetics of oxygen % values (FIG. 16F). The micro-tumors were screened against a 126-compound library of FDA-approved anti-cancer drugs (NIH) at 5 μM concentration identifying hits through time to onset analysis (FIG. 16G).

This method was tested on GBM cell line U87, yielding metastasizing tumors within 4 days of seeding. These micro-tumors were maintained several days under physiological conditions, while tracking metabolic function in real time using tumor-embedded microsensors (FIGS. 16D-G). This assay uncovered that this platform is uniquely capable of distinguishing between drugs that damage tumor cells but permit recurrence (False Positive) and slow working drugs that are missed in most screens (False Negative) but could specifically damage the root cause of the cancer (e.g. CSCs) with minimal effect to neighboring tissues (FIGS. 16H-J).

Patient-Derived Micro-Tumors Show Similar Characteristics to Micro-tumors and Patient Tumor—The present inventors currently use these "micro-tumors" to find and test drugs on patient derived samples that represent differing types of glioblastoma tumors. Solid tumor biopsies from patients, surgical specimen are minced to 1 mm³ fragments and digested at 37° C. to single cell suspensions. Samples are taken for FACS analysis to define tumor heterogeneity including CSCs and immune cell populations. These cells are then expended in non-adherent plates, preserving the in vivo like behavior, as was previously shown in micro-tumors. These cultures are then digested to single cells and resuspended and mixed with microvascular endothelial cells and 50 μm CPOx oxygen sensors in Matrigel basement membrane gel. A robotic liquid handling workstation which generates 384 well plates, placing one micro-tumor containing 50-75,000 cells in each well. Patient-derived Micro-tumor form an organoid within 24 hours, forming a micro-vascular network and metabolically stabilizing and differentiating into a heterogeneous tissue within 72 to 96 hours (FIGS. 14A-D). Micro-tumors preserve, in a similar way to the micro-tumors characterized by the Hubert/Rich labs, a phenotype and behavior that recapitulates the original tumor (FIGS. 14B-G).

Characterization of False Negative and False Positive Drugs

The early screen of patient specimens have screened out drugs that damage tumor cells but permit recurrence (False Positive) and highlighted new possible therapies (Positive) and uniquely uncovered slow working drugs that are missed in most screens (False Negative), but could specifically damage the root cause of the cancer (e.g. CSCs) with minimal effect to neighboring tissues (FIG. 15). This work is critical to identify therapies that more successfully treat each of the individual human patients.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

REFERENCES

Additional References Cited in Text

Aires, C. C., Ijlst, L., Stet, F., Prip-Buus, C., de Almeida, I. T., Duran, M., Wanders, R. J., and Silva, M. F. (2010). Inhibition of hepatic carnitine palmitoyl-transferase I (CPT IA) by valproyl-CoA as a possible mechanism of valproate-induced steatosis. Biochem Pharmacol 79, 792-799.

Aires, C. C., Ruiter, J. P., Luis, P. B., ten Brink, H. J., Ijlst, L., de Almeida, I. T., Duran, M., Wanders, R. J., and Silva, M. F. (2007). Studies on the extra-mitochondrial CoA-ester formation of valproic and Delta4-valproic acids. Biochim Biophys Acta 1771, 533-543.

Akhtar, M. A., Mathieson, K., Arey, B., Post, J., Prevette, R., Hillier, A., Patel, P., Ram, L. J., Van Thiel, D. H., and Nadir, A. (2008). Hepatic histopathology and clinical characteristics associated with antiretroviral therapy in HIV patients without viral hepatitis. Eur J Gastroenterol Hepatol 20, 1194-1204.

Andrade, R. J., Lucena, M. I., Fernandez, M. C., Pelaez, G., Pachkoria, K., Garcia-Ruiz, E., Garcia-Munoz, B., Gon-zalez-Grande, R., Pizarro, A., Duran, J. A., et al. (2005). Drug-induced liver injury: an analysis of 461 incidences submitted to the Spanish registry over a 10-year period. Gastroenterology 129, 512-521.

Bavli, D., Prill, S., Ezra, E., Levy, G., Cohen, M., Vinken, M., Vanfleteren, J., Jaeger, M., and Nahmias, Y. (2016). Real-time monitoring of metabolic function in liver-on-chip microdevices tracks the dynamics of mitochondrial dysfunction. Proceedings of the National Academy of Sciences of the United States of America 113, E2231-2240.

Bedogni, G., Miglioli, L., Masutti, F., Tiribelli, C., Marchesini, G., and Bellentani, S. (2005). Prevalence of and risk factors for nonalcoholic fatty liver disease: the Dionysos nutrition and liver study. Hepatology 42, 44-52.

Benedict, M., and Zhang, X. (2017). Non-alcoholic fatty liver disease: An expanded review. World journal of hepatology 9, 715-732.

Bergen, W. G., and Mersmann, H. J. (2005). Comparative aspects of lipid metabolism: impact on contemporary research and use of animal models. J Nutr 135, 2499-2502.

Bournat, J. C., and Brown, C. W. (2010). Mitochondrial dysfunction in obesity. Curr Opin Endocrinol Diabetes Obes 17, 446-452.

Browning, J. D., Szczepaniak, L. S., Dobbins, R., Nurem-berg, P., Horton, J. D., Cohen, J. C., Grundy, S. M., and Hobbs, H. H. (2004). Prevalence of hepatic steatosis in an urban population in the United States: impact of ethnicity. Hepatology 40, 1387-1395.

Chandrasekera, P. C., and Pippin, J. J. (2014). Of rodents and men: species-specific glucose regulation and type 2 dia-betes research. ALTEX 31, 157-176.

Cole, B. K., Feaver, R. E., Wamhoff, B. R., and Dash, A. (2018). Non-alcoholic fatty liver disease (NAFLD) mod-els in drug discovery. Expert Opin Drug Discov 13, 193-205.

da Cunha, J., Maselli, L. M., Stern, A. C., Spada, C., and Bydlowski, S. P. (2015). Impact of antiretroviral therapy on lipid metabolism of human immunodeficiency virus-infected patients: Old and new drugs. World J Virol 4, 56-77.

Di Girolamo, M., and Rudman, D. (1966). Species differ-ences in glucose metabolism and insulin responsiveness of adipose tissue. The American journal of physiology 210, 721-727.

Eizirik, D. L., Pipeleers, D. G., Ling, Z., Welsh, N., Hell-erstrom, C., and Andersson, A. (1994). Major species differences between humans and rodents in the suscepti-bility to pancreatic beta-cell injury. Proceedings of the National Academy of Sciences of the United States of America 91, 9253-9256.

Freneaux, E., Fromenty, B., Berson, A., Labbe, G., Degott, C., Letteron, P., Larrey, D., and Pessayre, D. (1990). Stereoselective and nonstereoselective effects of ibupro-fen enantiomers on mitochondrial beta-oxidation of fatty acids. The Journal of pharmacology and experimental therapeutics 255, 529-535.

Freneaux, E., Labbe, G., Letteron, P., The Le, D., Degott, C., Geneve, J., Larrey, D., and Pessayre, D. (1988). Inhibition of the mitochondrial oxidation of fatty acids by tetracy-cline in mice and in man: possible role in microvesicular steatosis induced by this antibiotic. Hepatology 8, 1056-1062.

Ghodke-Puranik, Y., Thorn, C. F., Lamba, J. K., Leeder, J. S., Song, W., Birnbaum, A. K., Altman, R. B., and Klein, T. E. (2013). Valproic acid pathway: pharmacokinetics and pharmacodynamics. Pharmacogenet Genomics 23, 236-241.

Hansen, H. H., Feigh, M., Veidal, S. S., Rigbolt, K. T., Vrang, N., and Fosgerau, K. (2017). Mouse models of nonalcoholic steatohepatitis in preclinical drug development. Drug Discov Today 22, 1707-1718.

Hautekeete, M. L., Degott, C., and Benhamou, J. P. (1990). Microvesicular steatosis of the liver. Acta clinica Belgica 45, 311-326.

Jafarian, I., Eskandari, M. R., Mashayekhi, V., Ahadpour, M., and Hosseini, M. J. (2013). Toxicity of valproic acid in isolated rat liver mitochondria. Toxicol Mech Methods 23, 617-623.

Kimura, S., Kobayashi, T., Tanaka, Y., and Sasaki, Y. (1991). Liver histopathology in clinical Reye syndrome. Brain & development 13, 95-100.

Kleiner, D. E., Chalasani, N. P., Lee, W. M., Fontana, R. J., Bonkovsky, H. L., Watkins, P. B., Hayashi, P. H., Davern, T. J., Navarro, V., Reddy, R., et al. (2014). Hepatic histological findings in suspected drug-induced liver injury: systematic evaluation and clinical associations. Hepatology 59, 661-670.

Klotz, U., and Antonin, K. H. (1977). Pharmacokinetics and bioavailability of sodium valproate. Clin Pharmacol Ther 21, 736-743.

Lazo, M., Hernaez, R., Eberhardt, M. S., Bonekamp, S., Kamel, I., Guallar, E., Koteish, A., Brancati, F. L., and Clark, J. M. (2013). Prevalence of nonalcoholic fatty liver disease in the United States: the Third National Health and Nutrition Examination Survey, 1988-1994. American journal of epidemiology 178, 38-45.

Letteron, P., Brahimi-Bourouina, N., Robin, M. A., Moreau, A., Feldmann, G., and Pessayre, D. (1997). Glucocorticoids inhibit mitochondrial matrix acyl-CoA dehydrogenases and fatty acid beta-oxidation. The American journal of physiology 272, G1141-1150.

Levy, G., Bomze, D., Heinz, S., Ramachandran, S. D., Noerenberg, A., Cohen, M., Shibolet, O., Sklan, E., Braspenning, J., and Nahmias, Y. (2015). Long-term culture and expansion of primary human hepatocytes. Nature biotechnology 33, 1264-1271.

Levy, G., Habib, N., Guzzardi, M. A., Kitsberg, D., Bomze, D., Ezra, E., Uygun, B. E., Uygun, K., Trippler, M., Schlaak, J. F., et al. (2016). Nuclear receptors control pro-viral and antiviral metabolic responses to hepatitis C virus infection. Nat Chem Biol 12, 1037-1045.

Massart, J., Begriche, K., Moreau, C., and Fromenty, B. (2017). Role of nonalcoholic fatty liver disease as risk factor for drug-induced hepatotoxicity. Journal of clinical and translational research 3, 212-232.

McLaughlin, D. B., Andrews, J. A., Hooper, W. D., Cannell, G. R., Eadie, M. J., and Dickinson, R. G. (2000). Apparent autoinduction of valproate beta-oxidation in humans. Br J Clin Pharmacol 49, 409-415.

Ouattara, D. A., Prot, J. M., Bunescu, A., Dumas, M. E., Elena-Herrmann, B., Leclerc, E., and Brochot, C. (2012). Metabolomics-on-a-chip and metabolic flux analysis for label-free modeling of the internal metabolism of HepG2/C3A cells. Mol Biosyst 8, 1908-1920.

Powell-Jackson, P. R., Tredger, J. M., and Williams, R. (1984). Hepatotoxicity to sodium valproate: a review. Gut 25, 673-681.

Prentice, R. L. (1976). A generalization of the probit and logit methods for dose response curves. Biometrics 32, 761-768.

Prill, S., Bavli, D., Levy, G., Ezra, E., Schmalzlin, E., Jaeger, M. S., Schwarz, M., Duschl, C., Cohen, M., and Nahmias, Y. (2016). Real-time monitoring of oxygen uptake in hepatic bioreactor shows CYP450-independent mitochondrial toxicity of acetaminophen and amiodarone. Archives of toxicology 90, 1181-1191.

Punapart, M., Eltermaa, M., Oflijan, J., Sutt, S., Must, A., Koks, S., Schalkwyk, L. C., Fernandes, C., Vasar, E., Soomets, U., et al. (2014). Effect of chronic valproic Acid treatment on hepatic gene expression profile in wfs1 knockout mouse. PPAR Res 2014, 349525.

Rezk, N. L., Tidwell, R. R., and Kashuba, A. D. (2003). Simultaneous determination of six HIV nucleoside analogue reverse transcriptase inhibitors and nevirapine by liquid chromatography with ultraviolet absorbance detection. J Chromatogr B Analyt Technol Biomed Life Sci 791, 137-147.

Scheffner, D., Konig, S., Rauterberg-Ruland, I., Kochen, W., Hofmann, W. J., and Unkelbach, S. (1988). Fatal liver failure in 16 children with valproate therapy. Epilepsia 29, 530-542.

Seckin, S., Basaran-Kucukgergin, C., and Uysal, M. (1999). Effect of acute and chronic administration of sodium valproate on lipid peroxidation and antioxidant system in rat liver. Pharmacol Toxicol 85, 294-298.

Silva, M. F., Aires, C. C., Luis, P. B., Ruiter, J. P., L, U., Duran, M., Wanders, R. J., and Tavares de Almeida, I. (2008). Valproic acid metabolism and its effects on mitochondrial fatty acid oxidation: a review. J Inherit Metab Dis 31, 205-216.

Silva, M. F., Ruiter, J. P., L, U., Allers, P., ten Brink, H. J., Jakobs, C., Duran, M., Tavares de Almeida, I., and Wanders, R. J. (2001). Synthesis and intramitochondrial levels of valproyl-coenzyme A metabolites. Anal Biochem 290, 60-67.

Stankov, M. V., Panayotova-Dimitrova, D., Leverkus, M., Vondran, F. W., Bauerfeind, R., Binz, A., and Behrens, G. M. (2012). Autophagy inhibition due to thymidine analogues as novel mechanism leading to hepatocyte dysfunction and lipid accumulation. AIDS 26, 1995-2006.

Sundar, K., Suarez, M., Banogon, P. E., and Shapiro, J. M. (1997). Zidovudine-induced fatal lactic acidosis and hepatic failure in patients with acquired immunodeficiency syndrome: report of two patients and review of the literature. Crit Care Med 25, 1425-1430.

Sussman, N. M., and McLain, L. W., Jr. (1979). A direct hepatotoxic effect of valproic acid. JAMA 242, 1173-1174.

Svard, J., Blanco, F., Nevin, D., Fayne, D., Mulcahy, F., Hennessy, M., and Spiers, J. P. (2014). Differential interactions of antiretroviral agents with LXR, ER and GR nuclear receptors: potential contributing factors to adverse events. Br J Pharmacol 171, 480-497.

Tandra, S., Yeh, M. M., Brunt, E. M., Vuppalanchi, R., Cummings, O. W., Unalp-Arida, A., Wilson, L. A., and Chalasani, N. (2011). Presence and significance of microvesicular steatosis in nonalcoholic fatty liver disease. Journal of hepatology 55, 654-659.

Tong, V., Teng, X. W., Chang, T. K., and Abbott, F. S. (2005). Valproic acid II: effects on oxidative stress, mitochondrial membrane potential, and cytotoxicity in glutathione-depleted rat hepatocytes. Toxicol Sci 86, 436-443.

Vernon, G., Baranova, A., and Younossi, Z. M. (2011). Systematic review: the epidemiology and natural history of non-alcoholic fatty liver disease and non-alcoholic steatohepatitis in adults. Alimentary pharmacology & therapeutics 34, 274-285.

Verweij-van Wissen, C. P., Aarnoutse, R. E., and Burger, D. M. (2005). Simultaneous determination of the HIV nucleoside analogue reverse transcriptase inhibitors lamivudine, didanosine, stavudine, zidovudine and abacavir in human plasma by reversed phase high per-

81

82 formance liquid chromatography. J Chromatogr B Analyt Technol Biomed Life Sci 816, 121-129.

Viengchareun, S., Caron, M., Auclair, M., Kim, M. J., Frachon, P., Capeau, J., Lombes, M., and Lombes, A. (2007). Mitochondrial toxicity of indinavir, stavudine and zidovudine involves multiple cellular targets in white and brown adipocytes. Antivir Ther 12, 919-929.

Wanless, I. R., Dore, S., Gopinath, N., Tan, J., Cameron, R., Heathcote, E. J., Blendis, L. M., and Levy, G. (1990). Histopathology of cocaine hepatotoxicity. Report of four patients. Gastroenterology 98, 497-501.

Wenner, M. M., Wilson, T. E., Davis, S. L., and Stachenfeld, N. S. (2011). Pharmacological curve fitting to analyze cutaneous adrenergic responses. J Appl Physiol (1985) 111, 1703-1709.

Williams, C. D., Stengel, J., Asike, M. I., Torres, D. M., Shaw, J., Contreras, M., Landt, C. L., and Harrison, S. A. (2011). Prevalence of nonalcoholic fatty liver disease and nonalcoholic steatohepatitis among a largely middle-aged population utilizing ultrasound and liver biopsy: a prospective study. Gastroenterology 140, 124-131.

Yang, Z. X., Shen, W., and Sun, H. (2010). Effects of nuclear receptor FXR on the regulation of liver lipid metabolism in patients with non-alcoholic fatty liver disease. Hepatol Int 4, 741-748.

Zimmerman, H. J., and Ishak, K. G. (1982). Valproate-induced hepatic injury: analyses of 23 fatal cases. Hepatology 2, 591-597.

---

What is claimed is:

1. A method of determining a toxicity of a pharmaceutically active agent to be administered to a human subject for a pre-selected exposure time for treating a disease or condition, the method comprising:

incubating a plurality of human organoids in culture with a respective plurality of different concentrations of said agent, wherein said plurality of human organoids comprise less than 20% variability in size, number of cells or both;

measuring function of said organoids at a time point, thereby providing a plurality of organoid-function values, one for each of said concentrations, wherein a time-period from a beginning of said incubation to said time point corresponds to said pre-selected exposure time of said subject to the agent;

fitting said plurality of organoid-function values to an S-shaped curve; and extracting from said S-shaped curve a predicted toxicity value of the agent for said pre-selected exposure time.

2. The method of claim 1, comprising repeating said measuring, said fitting, and said extracting at least once, at a different time point corresponding to a different pre-selected exposure time, thereby providing a plurality of predicted toxicity values, one for each pre-selected exposure time.

3. The method of claim 2, comprising identifying a plateau over said predicted toxicity values, as a function of time, and extrapolating said plateau to determine a predicted toxicity value for an exposure time that is longer than each of said pre-selected exposure times.

4. The method according to claim 1, wherein said measuring is in the absence of flow of said agent to and from said organoids.

5. The method according to claim 1, wherein said incubating is within bioreactors under condition of a steady flow of said agent to said organoids.

6. The method according to claim 1, wherein said measuring said function comprises measuring oxygen levels.

7. The method according to claim 6, wherein said organoids are embedded with oxygen sensors, and wherein said measuring said oxygen levels comprises measuring signals emitted by said oxygen sensors.

8. The method according to claim 1, wherein said asymptotic function, is an asymptotically decaying function.

9. The method according to claim 1, wherein said S-shaped curve is a sigmoid represented by $a_1+a_2/[1+ (c/a_3)^h]$, where $a_1$, $a_2$, $a_3$ and h are sigmoid parameters, and c represents said different concentrations, and wherein $a_3$ represents the toxicity of the agent.

10. The method of claim 1, wherein said S-shaped curve is a sigmoid curve.

* * * * *